US010813977B2

(12) United States Patent
Kumar-Singh et al.

(10) Patent No.: US 10,813,977 B2
(45) Date of Patent: Oct. 27, 2020

(54) COMPOSITIONS, METHODS AND KITS FOR TREATING COMPLEMENT RELATED DISORDERS

(71) Applicant: Trustees of Tufts College, Medford, MA (US)

(72) Inventors: Rajendra Kumar-Singh, Boston, MA (US); Derek Leaderer, Boston, MA (US); Siobhan Cashman, Boston, MA (US)

(73) Assignee: Trustees of Tufts College, Medford, MA (US)

( * ) Notice: Subject to any disclaimer, the term of this patent is extended or adjusted under 35 U.S.C. 154(b) by 374 days.

(21) Appl. No.: 15/444,500

(22) Filed: Feb. 28, 2017

(65) Prior Publication Data

US 2017/0209535 A1 Jul. 27, 2017

Related U.S. Application Data

(63) Continuation of application No. PCT/US2015/047405, filed on Aug. 28, 2015.
(Continued)

(51) Int. Cl.
*A61K 39/00* (2006.01)
*A61K 38/17* (2006.01)
(Continued)

(52) U.S. Cl.
CPC ............ *A61K 38/177* (2013.01); *A47K 7/026* (2013.01); *A61K 45/06* (2013.01); *A61P 37/00* (2018.01);
(Continued)

(58) Field of Classification Search
None
See application file for complete search history.

(56) References Cited

U.S. PATENT DOCUMENTS

| 4,405,712 A | 9/1983 | Vande Woude et al. |
| 4,650,764 A | 3/1987 | Temin et al. |

(Continued)

FOREIGN PATENT DOCUMENTS

| WO | 1985005629 A1 | 12/1985 |
| WO | 1989007150 A1 | 8/1989 |

(Continued)

OTHER PUBLICATIONS

Ruiz-Delgado et al., "Abnormalities in the expression of CD55 and CD59 surface molecules on peripheral blood cells are not specific to paroxysmal nocturnal hemoglobinuria," Hematology, vol. 14, No. 1: 33-37 (Year: 2009).*

(Continued)

*Primary Examiner* — M Franco G Salvoza
(74) *Attorney, Agent, or Firm* — Dana M. Gordon; Foley Hoag LLP

(57) ABSTRACT

Compositions, methods and kits are provided for treating complement related disorders in a subject with protein in combination having protein fusions of at least two of a CD46 protein, a CD55 protein and a CD59 protein or with a recombinant chimeric protein having at least two of a CD46 protein, a CD55 protein and a CD59 protein or with nucleic acids encoding these proteins. The composition negatively modulates classical and alternative complement pathways thereby treating complement related disorder such as macular degeneration, age-related macular degeneration, diabetic retinopathy, inflammatory bowel disease, thyroiditis, cryoglobulinaemia, fetal loss, organ graft rejection, cancer, etc.

11 Claims, 12 Drawing Sheets

Specification includes a Sequence Listing.

Related U.S. Application Data

(60) Provisional application No. 62/043,084, filed on Aug. 28, 2014.

(51) Int. Cl.

| | |
|---|---|
| *C07K 14/705* | (2006.01) |
| *A61P 37/00* | (2006.01) |
| *A47K 7/02* | (2006.01) |
| *B08B 7/02* | (2006.01) |
| *B25G 1/04* | (2006.01) |
| *B25G 1/06* | (2006.01) |
| *A61K 45/06* | (2006.01) |
| *G01N 33/68* | (2006.01) |

(52) U.S. Cl.
CPC ............... *B08B 7/02* (2013.01); *B25G 1/04* (2013.01); *B25G 1/06* (2013.01); *C07K 14/70596* (2013.01); *G01N 33/6893* (2013.01); *G01N 2333/4716* (2013.01)

(56) References Cited

U.S. PATENT DOCUMENTS

| | | | |
|---|---|---|---|
| 4,797,368 | A | 1/1989 | Carter et al. |
| 4,861,719 | A | 8/1989 | Miller |
| 4,980,289 | A | 12/1990 | Temin et al. |
| 5,112,767 | A | 5/1992 | Roy-Burman et al. |
| 5,122,767 | A | 6/1992 | Cameron et al. |
| 5,124,263 | A | 6/1992 | Temin et al. |
| 5,139,941 | A | 8/1992 | Muzyczka et al. |
| 5,624,837 | A | 4/1997 | Fodor et al. |
| 5,998,208 | A | 12/1999 | Fraefel et al. |
| 7,235,391 | B2 | 6/2007 | Wu et al. |
| 8,877,896 | B2 | 11/2014 | Kumar-Singh et al. |
| 2013/0149373 | A1 | 6/2013 | Kumar-Singh et al. |

FOREIGN PATENT DOCUMENTS

| | | |
|---|---|---|
| WO | 1990002797 A1 | 3/1990 |
| WO | 1990002806 A1 | 3/1990 |
| WO | 1990013641 A1 | 11/1990 |
| WO | 1992005266 A2 | 4/1992 |
| WO | 1992007943 A1 | 5/1992 |
| WO | 1992014829 A1 | 9/1992 |
| WO | 1993014188 A1 | 7/1993 |
| WO | 2012016162 A2 | 2/2012 |

OTHER PUBLICATIONS

Kuehn, MH et al. Disruption of the complement cascade delays retinal ganglion cell death following retinal ischemia-reperfusion. 2008, Exp Eye Res 87:89-95.

Laface, O et al. Gene transfer into hematopoietic progenitor cells mediated by an adeno-associated virus vector. 1988 Virology, 162(2):483-486.

Laughlin, CA et al. Latent Infection of KB Cells with Adeno-Associated Virus Type 2. 1986, J. Virol., 60(2):515-524.

Lebkowski, JS et al. Adeno-Associated Virus: a Vector System for Efficient Introduction and Integration of DNA into a Variety of Mammalian Cell Types. 1988, Mol. Cell. Biol., 8(10):3988-3996.

Levrero, M et al. Defective and nondefective adenovirus vectors for expressing foreign genes in vitro and in vivo. 1991, Gene, 101:195-202.

Makrides, SC. Therapeutic inhibition of the complement system. 1998, Pharmacol Rev 50: 59-87.

Maller, JB et al. Variation in complement factor 3 is associated with risk of age-related macular degeneration. 2007 Nat Genet 39: 1200-1201.

Markiewski, MM et al. The role of complement in inflammatory diseases from behind the scenes into the spotlight. 2007, Am J Pathol 171: 715-727.

Markowitz, D et al. A Safe Packaging Line for Gene Transfer: Separating Viral Genes on Two Different Plasmids. 1988, J. Virol. 62:1120-1124.

Mayilyan, KR. Complement genetics, deficiencies, and disease associations. 2012, Protein Cell 3: 487-496.

McLaughlin, SK et al., Adeno-Associated Virus General Transduction Vectors: Analysis of Proviral Structures. 1988, J. Virol., 62(6):1963 1973.

Miller, AD et al. Improved Retroviral Vectors for Gene Transfer and Expression. 1989, Biotechniques. 7:980-990.

Miller, AD et al. Redesign of Retrovirus Packaging Cell Lines to Avoid Recombination Leading to Helper Virus Production. 1986, Mol. Cell Biol. 6:2895-2902.

Mizuno, M et al. Membrane complement regulators protect against the development of type II collagen-induced arthritis in rats. 2001, Arthritis Rheum 44: 2425-2434.

Montes, T et al. Functional basis of protection against age-related macular degeneration conferred by a common polymorphism in complement factor B, 2009, Proc Natl Acad Sci USA 106: 4366-4371.

Morgenstern, B et al. Dialign: finding local similarities by multiple sequence alignment. 1998 Bioinformatics 14:290-294.

Morgenstern, JP et al. Advanced mammalian gene transfer: high titre retroviral vectors with multiple drug selection markers and a complementary helper-free packaging cell line. 1990 Nucleic Acids Res. 18:3587-3596.

Mullins, RF et al. Drusen associated with aging and age-related macular degeneration contain proteins common to extracellular deposits associated with atherosclerosis, elastosis, amyloidosis, and dense deposit disease. 2000 FASEB J 14: 835-846.

MULLINS, RF et al. Structure and composition of drusen associated with glomerulonephritis: implications for the role of complement activation in drusen biogenesis. 2001, Eye (Lond) 15: 390-395.

Mullins, RF et al. Elevated membrane attack complex in human choroid with high risk complement factor H genotypes. 2011 Exp Eye Res 93: 565-567.

Muzyczka, N. Use of adeno-associated virus as a general transduction vector for mammalian cells. 1992, Curr Top Microbiol Immunol, 158:97-129.

Myers, JD et al. An estimation of the hepatic blood flow nad splanchnic oxygen consumption in heart failure. 1948 J Clin Invest 27: 620-627.

Naldini, L et al. In Vivo Gene Delivery and Stable Transduction of Nondividing Cells by a Lentiviral Vector. 1996 Science 272: 263-267.

Laevo, Y et al. CD59 deficiency is associated with chronic hemolysis and childhood relapsing immune-mediated polyneuropathy. 2013, Blood 121: 129-135.

Nishiguchi, KM et al. C9-R95X polymorphism in patients with neovascular age-related macular degeneration2012 Invest Ophthalmol Vis Sci 53: 508-512.

Nose, M et al. Tissue distribution of HRF20, a novel factor preventing the membrane attack of homologous complement, and its predominant expression on endothelial cells in vivo. 1990 Immunology 70(2): 145-149.

Notredame, C et al. SAGA: sequence alignment by genetic algorithm 1996 Nuc. Acids Research 24:1515-24.

Nozaki, M et al. Drusen complement components C3a and C5a promote choroidal neovascularization. 2006, Proc Natl Acad Sci USA 103: 2328-2333.

O'Connor, M, et al. Construction of Large DNA Segments in *Escherichia coli*. 1989, Science 244:1307-1313.

Ohi, S. et al. Construction and replication of an adeno-associated virus expression vector that contains human beta-globin CDna. 1990, Gene, 89(2):279 282.

Orlean, P et al. GPI anchoring of protein in yeast and mammalian cells, or: how we learned to stop worrying and love glycophospholipids. 2007, JLR 48:993-1011.

Paneda, A et al. Effect of adeno-associated virus serotype and genomic structure on liver transduction and biodistribution in mice of both genders. 2009 Hum Gene Ther 20: 908-917.

(56) References Cited

OTHER PUBLICATIONS

Petranka, JG et al. Structure of the CD59-encoding gene: further evidence of a relationship to murine lymphocyte antigen Ly-6 protein. 1992, Proc. Nat. Acad. Sci. 89:7876-7879.
Piccoli, AK et al. Expression of complement regulatory proteins CD55, CD59, CD35, and CD46 in rheumatoid arthritis. 2011, Rev Bras Reumatol 51: 497-510.
Qin, X et al. The complement system in liver diseases. 2006, Cell Mol Immunol 3: 333-340.
Reynolds, R et al. Plasma Complement Components and Activation Fragments: Associations with Age-Related Macular Degeneration Genotypes and Phenotypes2009 Invest Ophthalmol Vis Sci 50: 5818-5827.
Richaud-Patin, Y et al. Deficiency of red cell bound CD55 and CD59 in patients with systemic lupus erythematosus. 2003 Immunol Lett 88: 95-99.
Ricklin, D et al. Complement in immune and inflammatory disorders: therapeutic intervention. 2013, J Immunol 190: 3839-3847.
Riley-Vargas, RC et al. CD46: expanding beyond complement regulation. 2004, Immunol 25: 496-503.
Ripoche, J et al. Isolation of two molecular populations of human complement factor H by hydrophobic affinity ahromatography. 1984, Biochem J 221: 89-96.
Rohrer, B et al. Eliminating complement factor D reduces photoreceptor susceptibility to light-induced damage. 2007 Invest Ophthalmol Vis Sci 48: 5282-5289.
Rollins, SA et al. The complement-inhibitory activity of CD59 resides in its capacity to block incorporation of C9 into membrane C5b-9. 1990, J Immunol. 144 (9):3478-83.
Sakoda, T et al., A High-Titer Lentiviral Production System Mediates Efficient Transduction of Differentiated Cells Including Beating Cardiac Myocytes. 1999, J. Mol. Cell. Cardiol., 31: 2037-2047.
Samulski, Rj et al. Targeted integration of adeno-associated virus (AAV) into human chromosome 19. 1991, Embo J. 10:3941-3950.
Samulski, RJ et al. Helper-Free Stocks of Recombinant Adeno-Associated Viruses: Normal Integration Does Not Require Viral Gene Expression. 1989, J. Virol, 63:3822-3828.
Satoh, S. Humoral injury in porcine livers perfused with human whole blood. 1997 Transplantation 64: 1117-1123.
Sawada, R et al. Complementary DNA sequence and deduced peptide sequence for CD59/MEM-43 antigen, the human homologue of murine lymphocyte antigen Ly-6C. 1989 Nucleic Acids Res 17(16) 6728.
Sekine, H et al. The benefit of targeted and selective inhibition of the alternative complement pathway for modulating autoimmunity and renal disease in MRL/lpr mice. 2011, Arthritis Rheum 63: 1076-1085.
Seya, T et al. Purification and characterization of a membrane protein (gp45-70) that is a cofactor for cleavage of C3b and C4b. 1986, J Exp Med. 163(4):837-55.
Shelling, AN et al. Targeted integration of transfected and infected adeno-associated virus vectors containing the neomycin resistance gene. 1994, Gene Therapy, 1: 165-169.
Shima, C et al. Complications in patients after intravitreal injection of bevacizumab. 2008 Acta Ophthalmol 86: 372-376.
Song, H et al. Complement receptor 2-mediated targeting of complement inhibitors to sites of complement activation. 2003, J Clin Invest 111: 1875-1885.
Stasi, K et al. Complement component 1Q (C1Q) upregulation in retina of murine, primate, and human glaucomatous eyes. 2006, Invest Ophthalmol Vis Sci 47: 1024-1029.
Sweigard, JH et al. Adenovirus-mediated delivery of CD46 attenuates the alternative complement pathway on RPE: Implications for age-related macular degeneration2011 Gene Ther 18: 613-621.
Tatusova, TA et al. Blast 2 Sequences, a new tool for comparing protein and nucleotide sequences. 1999 FEMS Microbiol. Lett. 174:247-50.
Tezel, G et al. Glaucomatous Tissue Stress and the Regulation of Immune Response through Glial Toll-like Receptor Signaling2010 Invest Ophthalmol Vis Sci 51(11): 5697-707.
Thompson, JD et al. CLUSTAL W: improving the sensitivity of progressive multiple sequence alignment through sequence weighting, position-specific gap penalties and weight matrix choice. 1994 Nuc. Acids Research 22:4673-80.
Thurman, JM et al. Dynamic control of the complement system by modulated expression of regulatory proteins. 2011 Lab Invest 91:4-11.
Tomkinson, B et al. Epstein-Barr Virus Recombinants from Overlapping Cosmid Fragments. 1993, J. Virol. 67, 1298-7306.
Tratschin, J et al. A Human Parvovirus, Adeno-Associated Virus, as a Eucaryotic Vector: Transient Expression and Encapsidation of the Procaryotic Gene for Chloramphenicol Acetyltransferase, 1984. Mol. Cell. Biol., 4:2072-2081.
Tratschin, J et al. Adeno-Associated Virus Vector for High-Frequency Integration, Expression, and Rescue of Genes in Mammalian Cells. 1985, Mol. Cell. Biol., 5:3258-3260.
Trouw, LA et al. Role of complement and complement regulators in the removal of apoptotic cells. 2008, Mol Immunol 45: 1199-1207.
Van Leeuwen, R et al. Epidemiology of age-related maculopathy: a review. 2003, European Journal of Epidemiology 18: 845-854.
Van Zijl, M. et al. Regeneration of Herpesviruses from Molecularly Cloned Subgenomic Fragments. 1988, J. Virol. 62,2191-95.
Vedeler, C et al. The expression of CD59 in normal human nervous tissue. 1994, Immunology 82(4): 542-547.
Von Leithner, PL et al. Complement Factor H Is Critical in the Maintenance of Retinal Perfusion. 2009, Am J Pathol 175: 412-421.
Walport, MJ. Complement. First of two parts. 2001, N Engl J Med 344: 1058-1066.
Walsh, CE et al. Phenotypic correction of Fanconi anemia in human hematopoietic cells with a recombinant adeno-associated virus vector. 1994, J. Clin. Invest, 94:1440 1448.
Walsh, LA et al. Transfection of human CD59 complementary DNA into rat cells confers resistance to human complement. 1991, Eur J. Immunol 21(3): 847-850.
Weeks, C et al.Decay-accelerating factor attenuates remote ischemia-reperfusion-initiated organ damage, 2007 Clin Immunol 124: 311-327.
Wei, JF et al. Expression of the human glucocerebrosidase and arylsulfatase A genes in murine and patient primary Fibroblasts transduced by an adeno-associated virus vector. 1994, Gene Therapy, 1:261-268.
Wu, L et al. Twelve-month safety of intravitreal injections of bevacizumab (Avastin): results of the Pan-American Collaborative Retina Study Group (PACORES). 2008 Graefes Arch Clin Exp Ophthalmol 246: 81-87.
Yates, JR et al. Complement C3 variant and the risk of age-related macular degeneration. 2007, N Engl J Med 357: 553-561.
Yoon, SH et al. Characterization of a soluble form of the C3b/C4b receptor (CR1) in human plasma. 1985, J Immunol 134: 3332-3338.
Yu, J et al., Mapping the active site of CD59. 1997, Journal of Experimental Medicine, 185(4):745-753.
Zhang, H et al. Targeting of functional antibody-CD59 fusion proteins to a cell surface. 1999, J Clin Invest 103: 55-61.
Zhang, J et al. Early complement activation and decreased levels of glycosylphosphatidylinositol-anchored complement inhibitors in human and experimental diabetic retinopathy. 2002, Diabetes 51: 3499-3504.
Zhou, SZ et al. Adeno-associated virus 2-mediated gene transfer in murine hematopoietic progenitor cells. 1993, Exp Hematol, 21:928-933.
Zipfel, PF et al. Complement regulators and inhibitory proteins. 2009, Nat Rev Immunol 9: 729-740.
Zufferey, R et al. Multiply attenuated lentiviral vector achieves efficient gene delivery in vivo. 1997, Nature Biotechnol., 15: 871-875.
International Search Report and Written Opinion of the International Search Authority in PCT/US15/47405 dated Jan. 29, 2016 (11 pgs.).
Anderson, DH et al. The pivotal role of the complement system in aging and age-related macular degeneration: hypothesis re-visited. 2010, Prog Retin Eye Res 29: 95-112.

(56) References Cited

OTHER PUBLICATIONS

Baudouin, C et al. Immunohistologic study of epiretinal membranes in proliferative vitreoretinopathy. 1990, Am J Ophthalmol 110: 593-598.
Bora, NS et al. Recombinant membrane-targeted form of CD59 inhibits the growth of choroidal neovascular complex in mice. 2010, J Biol Chem 285: 33826-33833.
Bora, NS et al. Role of Complement and Complement Membrane Attack Complex in Laser-Induced Choroidal Neovascularization. 2005 J Immunol 174: 491-497.
Bora, NS et al. Complement activation via alternative pathway is critical in the development of laser-induced choroidal neovascularization: role of factor B and factor H. 2006, J Immunol 177: 1872-1878.
Bora, NS et al. CD59, a complement regulatory protein, controls choroidal neovascularization in a mouse model of wet-type age-related macular degeneration. 2007 J Immunol 178: 1783-1790.
Cashman, SM et al. A Non Membrane-Targeted Human Soluble CD59 Attenuates Choroidal Neovascularization in a Model of Age Related Macular Degeneration. 2011 PLoS One 6: e19078.
Ballard, LL et al. Biochemical characterization of membrane cofactor protein of the complement system. 1988 J Immunol 141: 3923-3929.
Coffey, PJ et al. Complement factor H deficiency in aged mice causes retinal abnormalities and visual dysfunction. 2007 Proc Natl Acad Sci USA 104: 16651-16656.
Cohen, JI et al. Generation of varicella-zoster virus (VZV) and viral mutants from cosmid DNAs: VZV thymidylate synthetase is not essential for replication in vitro. 1993, Proc. Nat'l Acad. Sci. U.S.A. 90, 7376.
Colella, P et al. Ocular gene therapy: current progress and future prospects. 2009, Trends Mol Med 15: 23-31.
Cosset, F et al., A new avian leukosis virus-based packaging cell line that uses two separate transcomplementing helper genomes. 1990, J. Virol. 64:1070-1078.
Coyene, KE et al. Mapping of epitopes, glycosylation sites, and complement regulatory domains in human decay accelerating factor. 1992, J Immunol 149: 2906-2913.
Cunningham, C et al. A cosmid-based system for constructing mutants of herpes simplex virus type 1. 1993, Virology 197, 116-124.
Dull, T et al. A third-generation lentivirus vector with a conditional packaging system. 1998, J. Virol. 72: 8463-8471.
Ebrahimi, KB et al. Decreased membrane complement regulators in the retinal pigmented epithelium contributes to age-related macular degeneration. 2013, J Pathol 229: 729-742.
Edwards, AO et al. Complement factor H polymorphism and age-related macular degeneration. 2005, Science 308: 421-424.
Eglitis, MA et al. Retroviral vectors for introduction of genes into mammalian cells. 1988 Biotechniques 6:608-14.
Evans, GA et al. High efficiency vectors for cosmid microcloning and genomic analysis. 1989, Gene 79, 9-20, 1989.
Flotte, TR et al. Gene expression from adeno-associated virus vectors in airway epithelial cells. 1992, Am. J. Respir. Cell Mol. Biol., 7(3):349 356.
Fodor, WL et al. A novel bifunctional chimeric complement inhibitor that regulates C3 convertase and formation of be membrane attack complex. 1995 J Immunol 155: 4135-4138.
Gandhi, J et al. Soluble CD59 expressed from an adenovirus in vivo is a potent inhibitor of complement deposition on murine liver vascular endothelium. 2011 PLoS One 6: e21621.
Gerl, VB et al. Extensive deposits of complement C3d and C5b-9 in the choriocapillaris of eyes of patients with liabetic retinopathy. 2002 Invest Ophthalmol Vis Sci 43: 1104-1108.
Ginn, SL et al. Gene therapy clinical trials worldwide to 2012—an update. 2013 J Gene Med 15: 65-77.
Sold, B et al. Variation in factor B (BF) and complement component 2 (C2) genes is associated with age-related macular degeneration. 2006 Nat Genet 38: 458-462.
Graham, FL et al., Characteristics of a human cell line transformed by DNA from human adenovirus type 5. 1977 J. Gen. Virol., 36:59-72.
Graham, FL et al., Manipulation of adenovirus vectors. Methods in Molecular Biology: Gene Transfer and Expression Protocols 7, 1991, Humana Press, Clifton, NJ, 109-128, 1991.
Hageman, GS et al. A common haplotype in the complement regulatory gene factor H (HFI/CFH) predisposes individuals to age-related macular degeneration. 2005, Proc Natl Acad Sci USA 102: 7227-7232.
Haines, JL et al. Complement factor H variant increases the risk of age-related macular degeneration. 2005 Science 308: 419-421.
Hidestima, T. et al. Expression of HRF20, a regulatory molecule of complement activation, on peripheral blood mononuclear cells. 1990 Immunology 69(3): 396:401.
Holers, VM The spectrum of complement alternative pathway-mediated diseases. 2008, Immunol Rev 223: 300-316).
Iwamoto, N et al. Markedly high population of affected reticulocytes negative for decay-accelerating factor and CD59 in paroxysmal nocturnal hemoglobinuria. 1995 Blood 85: 2228-2232.
Jiang, H. et al. Evidence of multiyear factor IX expression by AAV-mediated gene transfer to skeletal muscle in an individual with severe hemophilia B. 2006 Mol Ther 14: 452-455.
Johnson, LV et al. A potential role for immune complex pathogenesis in drusen formation2000 Exp Eye Res 70: 141-449.
Johnson, LV et al. Complement activation and inflammatory processes in Drusen formation and age related macular degeneration. 2001, Exp Eye Res 73: 887-896.
Johnson, JB et al. The paramyxoviruses simian virus 5 and mumps virus recruit host cell CD46 to evade complement-mediated neutralization. 2009, J Virol 83: 7602-7611.
Kafri, T et al. Sustained expression of genes delivered directly into liver and muscle by lentiviral vectors. 1997. Nature Genet, 17: 314-317.
Kaplitt, MG et al. Long-term gene expression and phenotypic correction using adeno-associated virus vectors in the mammalian brain. 1994, Nat Genet., 8(2):148 54.
Karp, DR. Complement and systemic lupus erythematosus. 2005 Curr Opin Rheumatol 17: 538-542.
Kavanagh, D et al. Complement regulatory genes and hemolytic uremic syndromes. 2008 Annu Rev Med 59: 293-309.
Keane, PA et al. Development of Anti-VEGF Therapies for Intraocular Use: A Guide for Clinicians. 2012 J Ophthalmol 2012: 483034 (13 pgs.).
Kemp, PA et al. Immunohistochemical determination of complement activation in joint tissues of patients with rheumatoid arthritis and osteoarthritis using neoantigen-specific monoclonal antibodies. 1992, J Clin Lab Immunol 37: 147-162.
Kieffer, B et al. Three-dimensional solution structure of the extracellular region of the complement regulatory protein CD59, a new cell-surface protein domain related to snake venom neurotoxins. 1994, Biochem. 33:4471-82.
Kim, DD et al. Membrane complement regulatory proteins. 2006, Clin Immunol 118: 127-136.
Klein, M et al. Retinal Precursors and the Development of Geographic Atrophy in Age-Related Macular Degeneration. 2008, Ophthalmology 115: 1026-1031.
Klein, RJ et al. Fifteen-year cumulative incidence of age-related macular degeneration: the Beaver Dam Eye StudyOphthalmology. 2007, 114:253-262.
Klein, RJ, et al. Complement factor H polymorphism in age-related macular degeneration. 2005 Science 308: 385-389.
Konttinen, YT et al. Complement in acute and chronic arthritides: assessment of C3c, C9, and protectin (CD59) in synovial membrane. 1996, Ann Rheum Dis 55: 888-894.
Korman, AJ et al., Expression of human class II major histocompatibility complex antigens using retrovirus vectors. 1987, Proc. Natl. Acad. Sol. USA. 84:2150-2154.
Kroshus, TJ et al. A recombinant soluble chimeric complement inhibitor composed of human CD46 and CD55 reduces acute cardiac tissue injury in models of pig-to-human heart transplantation. 2000, Transplantation 69: 2282-2289.

(56) References Cited

OTHER PUBLICATIONS

Clift, LE et al. CD55 and CD59 protein expression by Apodemus (field mice) sperm in the absence of CD46, J Reprod Immunol. Jul. 2009;81(1):62-73.
Leaderer, D et al. Adeno-associated virus mediated delivery of an engineered protein that combines the complement inhibitory properties of CD46, CD55 and CD59, J Gene Med. Jun.-Jul. 2015;17(6-7):101-15.
Supplementary European Search Report received in related European application No. 158368803, dated Mar. 16, 2018 (10 pages)

* cited by examiner

Figure 1A
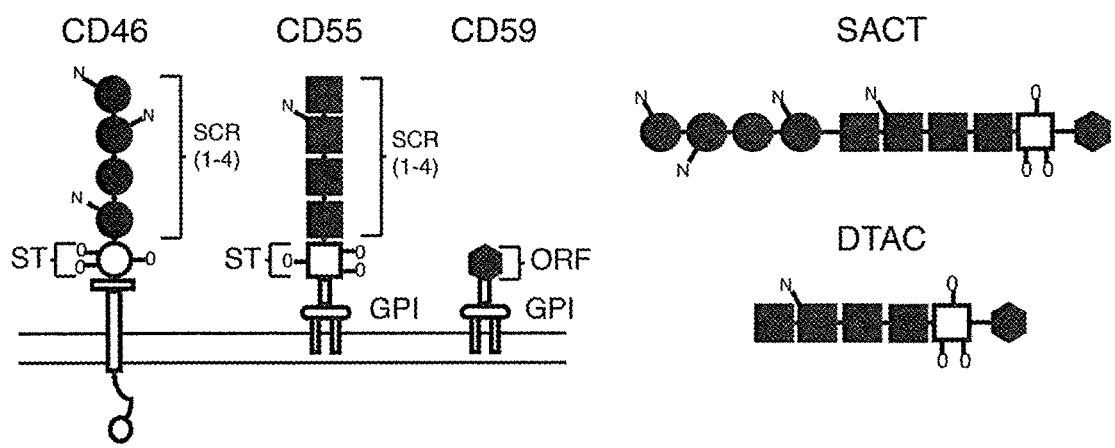
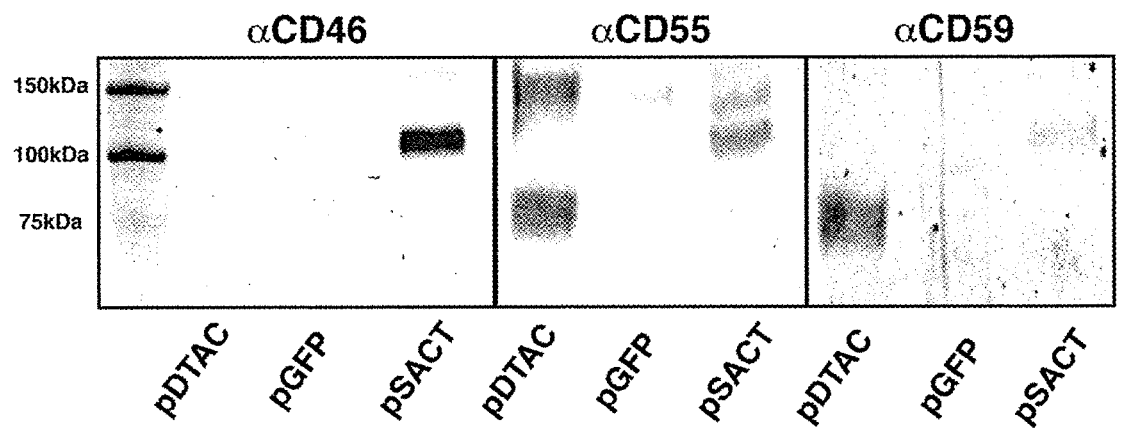
Figure 1B

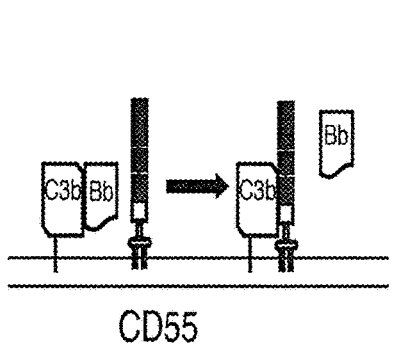
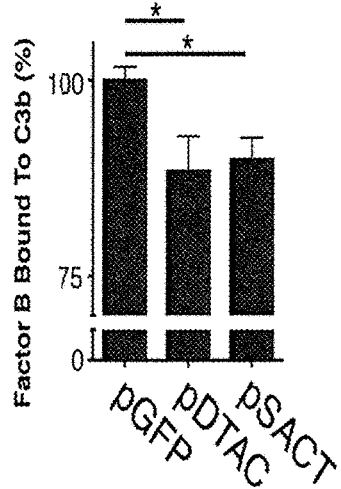
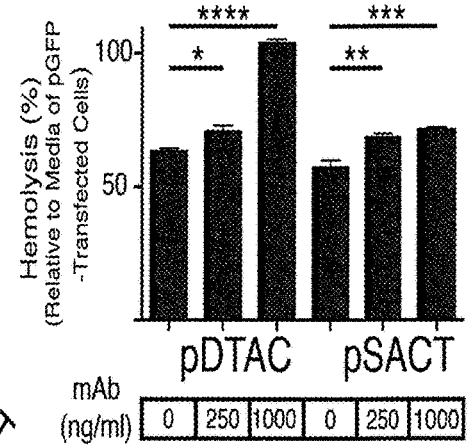
Figure 3A
Figure 3B
Figure 3C

Figure 7A
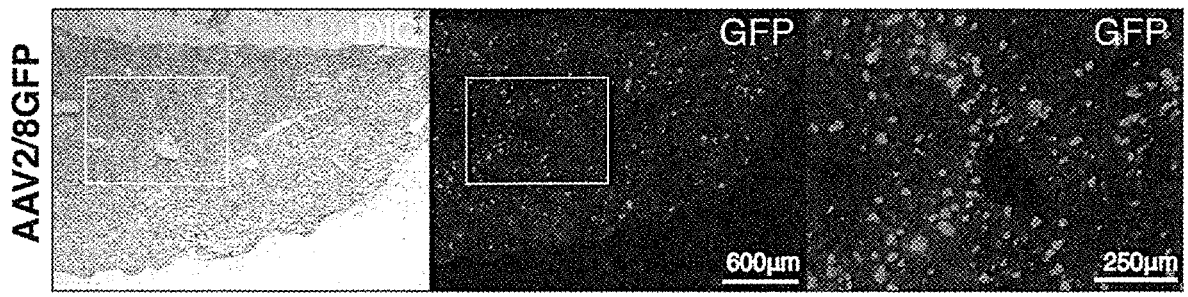
Figure 7B
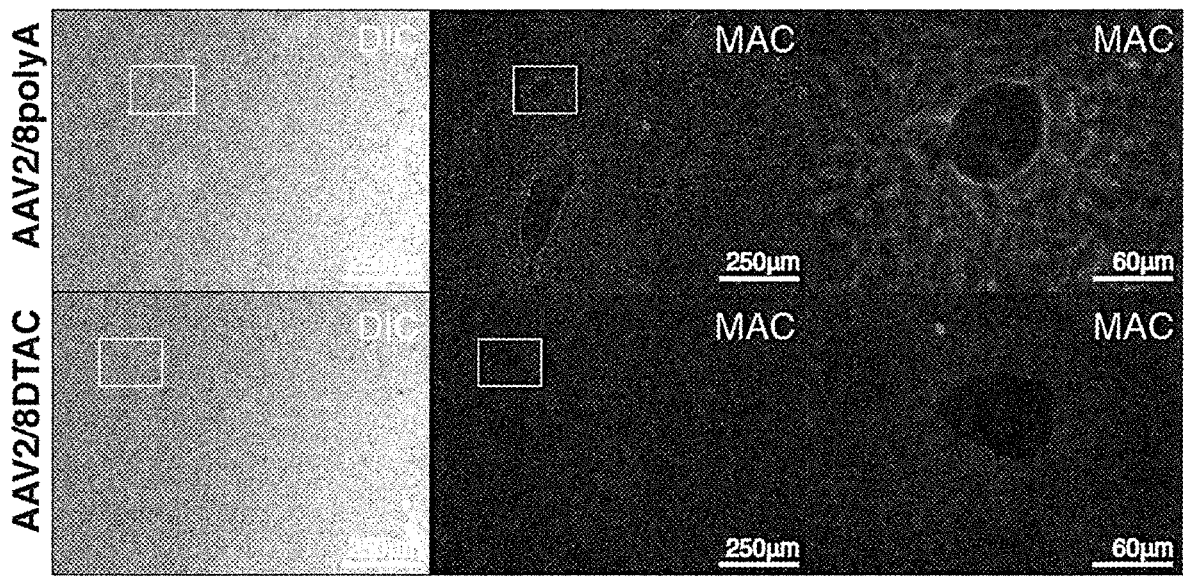
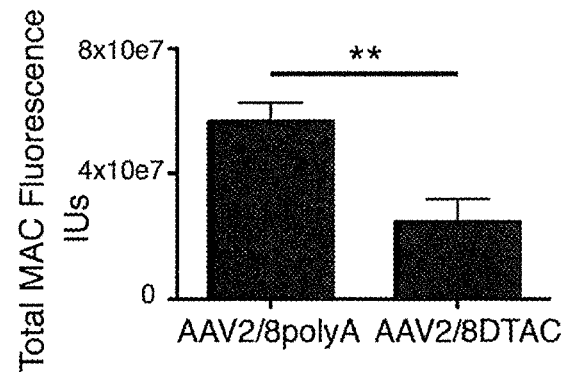
Figure 7C
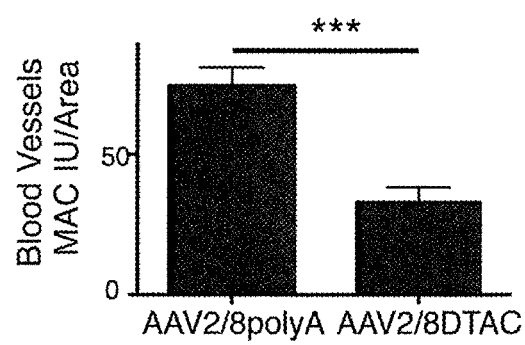
Figure 7D Figure 8A
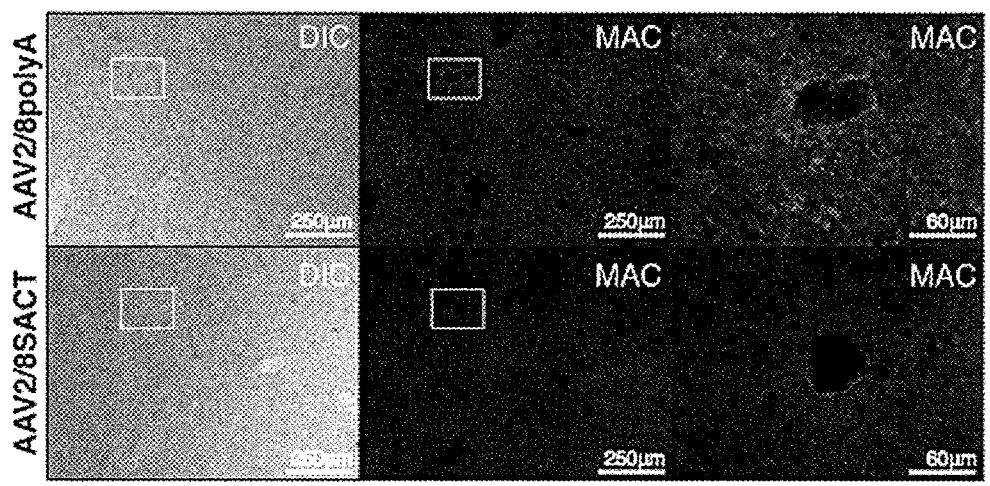
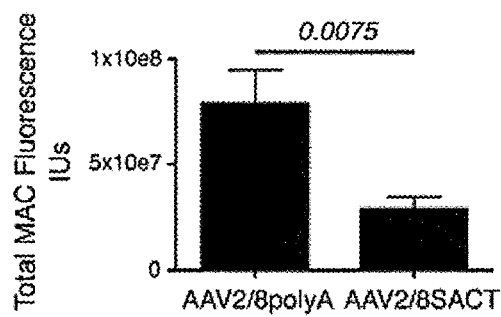
Figure 8B
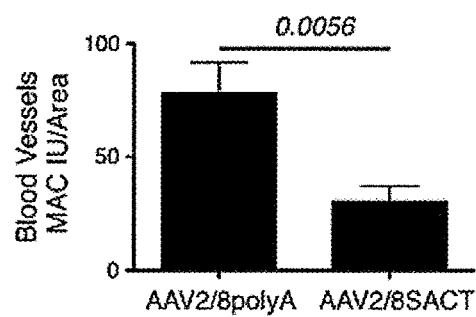
Figure 8C

SEQUENCE LISTING

```
<160> NUMBER OF SEQ ID NOS: 5

<210> SEQ ID NO 1
<211> LENGTH: 2067
<212> TYPE: DNA
<213> ORGANISM: Artificial Sequence
<220> FEATURE:
<223> OTHER INFORMATION: The nucleotide sequence was designed and
      synthesized

<400> SEQUENCE: 1
atgggaatcc aaggagggtc tgtcctgttc gggctgctgc tcgtcctggc tgtcttctgc      60
cattcaggtc atagcggatg tgaggagcca ccaacatttg aagctatgga gctcattggt     120
aaaccaaaac cctactatga gattggtgaa cgagtagatt ataagtgtaa aaaaggatac     180
ttctatatac ctcctcttgc cacccatact atttgtgatc ggaatcatac atggctacct     240
gtctcagatg acgcctgtta tagagaaaca tgtccatata tacgggatcc tttaaatggc     300
caagcagtcc ctgcaaatgg gacttacgag tttggttatc agatgcactt tatttgtaat     360
gagggttatt acttaattgg tgaagaaatt ctatattgtg aacttaaagg atcagtagca     420
atttggagcg gtaagccccc aatatgtgaa aaggttttgt gtacaccacc tccaaaaata     480
aaaaatggaa aacacacctt tagtgaagta gaagtatttg agtatcttga tgcagtaact     540
tatagttgtg atcctgcacc tggaccagat ccattttcac ttattggaga gagcacgatt     600
tattgtggtg acaattcagt gtggagtcgt gctgctccag agtgtaaagt ggtcaaatgt     660
cgatttccag tagtcgaaaa tggaaaacag atatcaggat ttggaaaaaa attttactac     720
aaagcaacag ttatgtttga atgcgataag ggtttttacc tcgatggcag cgacacaatt     780
gtctgtgaca gtaacagtac ttgggatccc ccagttccaa agtgtcttaa agtgggaggc     840
ggaggtggag gtgactgtgg ccttccccca gatgtaccta atgcccagcc agctttggaa     900
ggccgtacaa gttttcccga ggatactgta ataacgtaca aatgtgaaga aagctttgtg     960
aaaattcctg gcgagaagga ctcagtgatc tgccttaagg gcagtcaatg gtcagatatt    1020
gaagagttct gcaatcgtag ctgcgaggtg ccaacaaggc taaattctgc atccctcaaa    1080
cagccttata tcactcagaa ttattttcca gtcggtactg ttgtggaata tgagtgccgt    1140
ccaggttaca gaagagaacc ttctctatca ccaaaactaa cttgccttca gaatttaaaa    1200
tggtccacag cagtcgaatt ttgtaaaaag aaatcatgcc ctaatccggg agaaatacga    1260
aatggtcaga ttgatgtacc aggtggcata ttatttggtg caaccatctc cttctcatgt    1320
aacacagggt acaaattatt tggctcgact tctagttttt gtcttatttc aggcagctct    1380
gtccagtgga gtgacccgtt gccagagtgc agagaaattt attgtccagc accaccacaa    1440
```

```
attgacaatg gaataattca aggggaacgt gaccattatg gatatagaca gtctgtaacg    1500
tatgcatgta ataaaggatt caccatgatt ggagagcact ctatttattg tactgtgaat    1560
aatgatgaag gagagtggag tggcccacca cctgaatgca gaggaaaatc tctaacttcc    1620
aaggtcccac caacagttca gaaacctacc acagtaaatg ttccaactac agaagtctca    1680
ccaacttctc agaaaaccac cacaaaaacc accacaccaa atgctcaagc aacacggagt    1740
acacctgttt ccaggacaac caagcatttt catgaaacaa ccccaaataa ggaagtggaa    1800
accacttcag gtactaccgg cggaggtgga ggtctgcagt gctacaactg tcctaaccca    1860
actgctgact gcaaaacagc cgtcaattgt tcatctgatt ttgatgcgtg tctcattacc    1920
aaagctgggt acaagtgtaa taacaagtgt tggaagtttg agcattgcaa tttcaacgac    1980
gtcacaaccc gcttgaggga aaatgagcta acgtactact gctgcaagaa ggacctgtgt    2040
aactttaacg aacagcttga atgatga                                        2067
```

<210> SEQ ID NO 2
<211> LENGTH: 687
<212> TYPE: PRT
<213> ORGANISM: Artificial Sequence
<220> FEATURE:
<223> OTHER INFORMATION: The amino acid sequence was designed and
      synthesized

<400> SEQUENCE: 2

```
Met Gly Ile Gln Gly Gly Ser Val Leu Phe Gly Leu Leu Leu Val Leu
1               5                   10                  15

Ala Val Phe Cys His Ser Gly His Ser Gly Cys Glu Glu Pro Pro Thr
            20                  25                  30

Phe Glu Ala Met Glu Leu Ile Gly Lys Pro Lys Pro Tyr Tyr Glu Ile
        35                  40                  45

Gly Glu Arg Val Asp Tyr Lys Cys Lys Lys Gly Tyr Phe Tyr Ile Pro
    50                  55                  60

Pro Leu Ala Thr His Thr Ile Cys Asp Arg Asn His Thr Trp Leu Pro
65                  70                  75                  80

Val Ser Asp Asp Ala Cys Tyr Arg Glu Thr Cys Pro Tyr Ile Arg Asp
                85                  90                  95

Pro Leu Asn Gly Gln Ala Val Pro Ala Asn Gly Thr Tyr Glu Phe Gly
            100                 105                 110

Tyr Gln Met His Phe Ile Cys Asn Glu Gly Tyr Tyr Leu Ile Gly Glu
        115                 120                 125

Glu Ile Leu Tyr Cys Glu Leu Lys Gly Ser Val Ala Ile Trp Ser Gly
    130                 135                 140

Lys Pro Pro Ile Cys Glu Lys Val Leu Cys Thr Pro Pro Lys Ile
145                 150                 155                 160

Lys Asn Gly Lys His Thr Phe Ser Glu Val Glu Val Phe Glu Tyr Leu
                165                 170                 175

Asp Ala Val Thr Tyr Ser Cys Asp Pro Ala Pro Gly Pro Asp Pro Phe
            180                 185                 190

Ser Leu Ile Gly Glu Ser Thr Ile Tyr Cys Gly Asp Asn Ser Val Trp
        195                 200                 205

Ser Arg Ala Ala Pro Glu Cys Lys Val Val Lys Cys Arg Phe Pro Val
    210                 215                 220

Val Glu Asn Gly Lys Gln Ile Ser Gly Phe Gly Lys Lys Phe Tyr Tyr
225                 230                 235                 240

Lys Ala Thr Val Met Phe Glu Cys Asp Lys Gly Phe Tyr Leu Asp Gly
```

-continued

```
                245                 250                 255
Ser Asp Thr Ile Val Cys Asp Ser Asn Ser Thr Trp Asp Pro Pro Val
            260                 265                 270
Pro Lys Cys Leu Lys Val Gly Gly Gly Gly Gly Asp Cys Gly Leu
        275                 280                 285
Pro Pro Asp Val Pro Asn Ala Gln Pro Ala Leu Glu Gly Arg Thr Ser
        290                 295                 300
Phe Pro Glu Asp Thr Val Ile Thr Tyr Lys Cys Glu Glu Ser Phe Val
305                 310                 315                 320
Lys Ile Pro Gly Glu Lys Asp Ser Val Ile Cys Leu Lys Gly Ser Gln
                325                 330                 335
Trp Ser Asp Ile Glu Glu Phe Cys Asn Arg Ser Cys Glu Val Pro Thr
                340                 345                 350
Arg Leu Asn Ser Ala Ser Leu Lys Gln Pro Tyr Ile Thr Gln Asn Tyr
            355                 360                 365
Phe Pro Val Gly Thr Val Val Glu Tyr Glu Cys Arg Pro Gly Tyr Arg
        370                 375                 380
Arg Glu Pro Ser Leu Ser Pro Lys Leu Thr Cys Leu Gln Asn Leu Lys
385                 390                 395                 400
Trp Ser Thr Ala Val Glu Phe Cys Lys Lys Ser Cys Pro Asn Pro
                405                 410                 415
Gly Glu Ile Arg Asn Gly Gln Ile Asp Val Pro Gly Gly Ile Leu Phe
                420                 425                 430
Gly Ala Thr Ile Ser Phe Ser Cys Asn Thr Gly Tyr Lys Leu Phe Gly
            435                 440                 445
Ser Thr Ser Ser Phe Cys Leu Ile Ser Gly Ser Ser Val Gln Trp Ser
        450                 455                 460
Asp Pro Leu Pro Glu Cys Arg Glu Ile Tyr Cys Pro Ala Pro Pro Gln
465                 470                 475                 480
Ile Asp Asn Gly Ile Ile Gln Gly Glu Arg Asp His Tyr Gly Tyr Arg
                485                 490                 495
Gln Ser Val Thr Tyr Ala Cys Asn Lys Gly Phe Thr Met Ile Gly Glu
                500                 505                 510
His Ser Ile Tyr Cys Thr Val Asn Asn Asp Glu Gly Glu Trp Ser Gly
            515                 520                 525
Pro Pro Pro Glu Cys Arg Gly Lys Ser Leu Thr Ser Lys Val Pro Pro
        530                 535                 540
Thr Val Gln Lys Pro Thr Thr Val Asn Val Pro Thr Thr Glu Val Ser
545                 550                 555                 560
Pro Thr Ser Gln Lys Thr Thr Thr Lys Thr Thr Thr Pro Asn Ala Gln
                565                 570                 575
Ala Thr Arg Ser Thr Pro Val Ser Arg Thr Thr Lys His Phe His Glu
            580                 585                 590
Thr Thr Pro Asn Lys Gly Ser Gly Thr Thr Ser Gly Thr Thr Gly Gly
        595                 600                 605
Gly Gly Gly Leu Gln Cys Tyr Asn Cys Pro Asn Pro Thr Ala Asp Cys
        610                 615                 620
Lys Thr Ala Val Asn Cys Ser Ser Asp Phe Asp Ala Cys Leu Ile Thr
625                 630                 635                 640
Lys Ala Gly Leu Gln Val Tyr Asn Lys Cys Trp Lys Phe Glu His Cys
                645                 650                 655
Asn Phe Asn Asp Val Thr Thr Arg Leu Arg Glu Asn Glu Leu Thr Tyr
                660                 665                 670
```

Tyr Cys Cys Lys Lys Asp Leu Cys Asn Phe Asn Glu Gln Leu Glu
        675                 680                 685

<210> SEQ ID NO 3
<211> LENGTH: 1296
<212> TYPE: DNA
<213> ORGANISM: Artificial Sequence
<220> FEATURE:
<223> OTHER INFORMATION: The nucleotide sequence was designed and
      synthesized

<400> SEQUENCE: 3

```
atgggaatcc aaggagggtc tgtcctgttc gggctgctgc tcgtcctggc tgtcttctgc     60
cattcaggtc atagcggagg tgactgtggc cttcccccag atgtacctaa tgcccagcca    120
gctttggaag gccgtacaag ttttcccgag atactgtaa taacgtacaa atgtgaagaa    180
agctttgtga aaattcctgg cgagaaggac tcagtgatct gccttaaggg cagtcaatgg    240
tcagatattg aagagttctg caatcgtagc tgcgaggtgc caacaaggct aaattctgca    300
tccctcaaac agccttatat cactcagaat tattttccag tcggtactgt tgtggaatat    360
gagtgccgtc aggttacag aagagaacct tctctatcac caaaactaac ttgccttcag    420
aatttaaaat ggtccacagc agtcgaattt tgtaaaaaga atcatgccc taatccggga    480
gaaatacgaa atggtcagat tgatgtacca ggtggcatat atttggtgc aaccatctcc    540
ttctcatgta acacagggta caattattt ggctcgactt ctagtttttg tcttatttca    600
ggcagctctg tccagtggag tgacccgttg ccagagtgca gagaaattta ttgtccagca    660
ccaccacaaa ttgacaatgg aataattcaa ggggaacgtg accattatgg atatagacag    720
tctgtaacgt atgcatgtaa taaggattc accatgattg agagcactc tatttattgt    780
actgtgaata tgatgaagg agagtggagt ggcccaccac ctgaatgcag aggaaaatct    840
ctaacttcca aggtcccacc aacagttcag aaacctacca cagtaaatgt tccaactaca    900
gaagtctcac caacttctca gaaaaccacc acaaaaacca ccacaccaaa tgctcaagca    960
acacggagta cacctgtttc caggacaacc aagcattttc atgaaacaac cccaaataaa   1020
ggaagtggaa ccacttcagg tactaccggc ggaggtggag gtctgcagtg ctacaactgt   1080
cctaacccaa ctgctgactg caaaacagcc gtcaattgtt catctgattt tgatgcgtgt   1140
ctcattacca agctgggtt acaagtgtat aacaagtgtt ggaagtttga gcattgcaat   1200
ttcaacgacg tcacaacccg cttgagggaa aatgagctaa cgtactactg ctgcaagaag   1260
gacctgtgta actttaacga acagcttgaa tgatga                             1296
```

<210> SEQ ID NO 4
<211> LENGTH: 430
<212> TYPE: PRT
<213> ORGANISM: Artificial Sequence
<220> FEATURE:
<223> OTHER INFORMATION: The amino acid sequence was designed and
      synthesized

<400> SEQUENCE: 4

Met Gly Ile Gln Gly Gly Ser Val Leu Phe Gly Leu Leu Leu Val Leu
1               5                   10                  15

Ala Val Phe Cys His Ser Gly His Ser Gly Gly Asp Cys Gly Leu Pro
            20                  25                  30

Pro Asp Val Pro Asn Ala Gln Pro Ala Leu Glu Gly Arg Thr Ser Phe
        35                  40                  45

```
Pro Glu Asp Thr Val Ile Thr Tyr Lys Cys Glu Glu Ser Phe Val Lys
 50                  55                  60

Ile Pro Gly Glu Lys Asp Ser Val Ile Cys Leu Lys Gly Ser Gln Trp
 65                  70                  75                  80

Ser Asp Ile Glu Glu Phe Cys Asn Arg Ser Cys Glu Val Pro Thr Arg
                 85                  90                  95

Leu Asn Ser Ala Ser Leu Lys Gln Pro Tyr Ile Thr Gln Asn Tyr Phe
                100                 105                 110

Pro Val Gly Thr Val Val Glu Tyr Glu Cys Arg Pro Gly Tyr Arg Arg
                115                 120                 125

Glu Pro Ser Leu Ser Pro Lys Leu Thr Cys Leu Gln Asn Leu Lys Trp
130                 135                 140

Ser Thr Ala Val Glu Phe Cys Lys Lys Lys Ser Cys Pro Asn Pro Gly
145                 150                 155                 160

Glu Ile Arg Asn Gly Gln Ile Asp Val Pro Gly Gly Ile Leu Phe Gly
                165                 170                 175

Ala Thr Ile Ser Phe Ser Cys Asn Thr Gly Tyr Lys Leu Phe Gly Ser
                180                 185                 190

Thr Ser Ser Phe Cys Leu Ile Ser Gly Ser Ser Val Gln Trp Ser Asp
                195                 200                 205

Pro Leu Pro Glu Cys Arg Glu Ile Tyr Cys Pro Ala Pro Pro Gln Ile
210                 215                 220

Asp Asn Gly Ile Ile Gln Gly Glu Arg Asp His Tyr Gly Tyr Arg Gln
225                 230                 235                 240

Ser Val Thr Tyr Ala Cys Asn Lys Gly Phe Thr Met Ile Gly Glu His
                245                 250                 255

Ser Ile Tyr Cys Thr Val Asn Asn Asp Glu Gly Glu Trp Ser Gly Pro
                260                 265                 270

Pro Pro Glu Cys Arg Gly Lys Ser Leu Thr Ser Lys Val Pro Pro Thr
                275                 280                 285

Val Gln Lys Pro Thr Thr Val Asn Val Pro Thr Thr Glu Val Ser Pro
290                 295                 300

Thr Ser Gln Lys Thr Thr Thr Lys Thr Thr Thr Pro Asn Ala Gln Ala
305                 310                 315                 320

Thr Arg Ser Thr Pro Val Ser Arg Thr Thr Lys His Phe His Glu Thr
                325                 330                 335

Thr Pro Asn Lys Gly Ser Gly Thr Thr Ser Gly Thr Thr Gly Gly Gly
                340                 345                 350

Gly Gly Leu Gln Cys Tyr Asn Cys Pro Asn Pro Thr Ala Asp Cys Lys
                355                 360                 365

Thr Ala Val Asn Cys Ser Ser Asp Phe Asp Ala Cys Leu Ile Thr Lys
370                 375                 380

Ala Gly Leu Gln Val Tyr Asn Lys Cys Trp Lys Phe Glu His Cys Asn
385                 390                 395                 400

Phe Asn Asp Val Thr Thr Arg Leu Arg Glu Asn Glu Leu Thr Tyr Tyr
                405                 410                 415

Cys Cys Lys Lys Asp Leu Cys Asn Phe Asn Glu Gln Leu Glu
                420                 425                 430

<210> SEQ ID NO 5
<211> LENGTH: 686
<212> TYPE: PRT
<213> ORGANISM: Artificial Sequence
<220> FEATURE:
<223> OTHER INFORMATION: The amino acid sequence was designed and
``` synthesized

<400> SEQUENCE: 5

```
Met Gly Ile Gln Gly Gly Ser Val Leu Phe Gly Leu Leu Leu Val Leu
1               5                   10                  15

Ala Val Phe Cys His Ser Gly His Ser Leu Gln Cys Tyr Asn Cys Pro
            20                  25                  30

Asn Pro Thr Ala Asp Cys Lys Thr Ala Val Asn Cys Ser Ser Asp Phe
        35                  40                  45

Asp Ala Cys Leu Ile Thr Lys Ala Gly Leu Gln Val Tyr Asn Lys Cys
50                  55                  60

Trp Lys Phe Glu His Cys Asn Phe Asn Asp Val Thr Thr Arg Leu Arg
65                  70                  75                  80

Glu Asn Glu Leu Thr Tyr Tyr Cys Cys Lys Lys Asp Leu Cys Asn Phe
                85                  90                  95

Asn Glu Gln Leu Glu Gly Gly Gly Gly Cys Glu Glu Pro Pro Thr
            100                 105                 110

Phe Glu Ala Met Glu Leu Ile Gly Lys Pro Lys Pro Tyr Tyr Glu Ile
            115                 120                 125

Gly Glu Arg Val Asp Tyr Lys Cys Lys Lys Gly Tyr Phe Tyr Ile Pro
130                 135                 140

Pro Leu Ala Thr His Thr Ile Cys Asp Arg Asn His Thr Trp Leu Pro
145                 150                 155                 160

Val Ser Asp Asp Ala Cys Tyr Arg Glu Thr Cys Pro Tyr Ile Arg Asp
                165                 170                 175

Pro Leu Asn Gly Gln Ala Val Pro Ala Asn Gly Thr Tyr Glu Phe Gly
            180                 185                 190

Tyr Gln Met His Phe Ile Cys Asn Glu Gly Tyr Tyr Leu Ile Gly Glu
            195                 200                 205

Glu Ile Leu Tyr Cys Glu Leu Lys Gly Ser Val Ala Ile Trp Ser Gly
210                 215                 220

Lys Pro Pro Ile Cys Glu Lys Val Leu Cys Thr Pro Pro Pro Lys Ile
225                 230                 235                 240

Lys Asn Gly Lys His Thr Phe Ser Glu Val Glu Val Phe Glu Tyr Leu
                245                 250                 255

Asp Ala Val Thr Tyr Ser Cys Asp Pro Ala Pro Gly Pro Asp Pro Phe
            260                 265                 270

Ser Leu Ile Gly Glu Ser Thr Ile Tyr Cys Gly Asp Asn Ser Val Trp
            275                 280                 285

Ser Arg Ala Ala Pro Glu Cys Lys Val Val Lys Cys Arg Phe Pro Val
290                 295                 300

Val Glu Asn Gly Lys Gln Ile Ser Gly Phe Gly Lys Lys Phe Tyr Tyr
305                 310                 315                 320

Lys Ala Thr Val Met Phe Glu Cys Asp Lys Gly Phe Tyr Leu Asp Gly
                325                 330                 335

Ser Asp Thr Ile Val Cys Asp Ser Asn Ser Thr Trp Asp Pro Pro Val
            340                 345                 350

Pro Lys Cys Leu Lys Val Gly Gly Gly Gly Gly Asp Cys Gly Leu
            355                 360                 365

Pro Pro Asp Val Pro Asn Ala Gln Pro Ala Leu Glu Gly Arg Thr Ser
370                 375                 380

Phe Pro Glu Asp Thr Val Ile Thr Tyr Lys Cys Glu Glu Ser Phe Val
385                 390                 395                 400
```

-continued

```
Lys Ile Pro Gly Glu Lys Asp Ser Val Ile Cys Leu Lys Gly Ser Gln
            405                 410                 415
Trp Ser Asp Ile Glu Glu Phe Cys Asn Arg Ser Cys Glu Val Pro Thr
            420                 425                 430
Arg Leu Asn Ser Ala Ser Leu Lys Gln Pro Tyr Ile Thr Gln Asn Tyr
            435                 440                 445
Phe Pro Val Gly Thr Val Val Glu Tyr Glu Cys Arg Pro Gly Tyr Arg
    450                 455                 460
Arg Glu Pro Ser Leu Ser Pro Lys Leu Thr Cys Leu Gln Asn Leu Lys
465                 470                 475                 480
Trp Ser Thr Ala Val Glu Phe Cys Lys Lys Lys Ser Cys Pro Asn Pro
                485                 490                 495
Gly Glu Ile Arg Asn Gly Gln Ile Asp Val Pro Gly Gly Ile Leu Phe
                500                 505                 510
Gly Ala Thr Ile Ser Phe Ser Cys Asn Thr Gly Tyr Lys Leu Phe Gly
            515                 520                 525
Ser Thr Ser Ser Phe Cys Leu Ile Ser Gly Ser Ser Val Gln Trp Ser
        530                 535                 540
Asp Pro Leu Pro Glu Cys Arg Glu Ile Tyr Cys Pro Ala Pro Pro Gln
545                 550                 555                 560
Ile Asp Asn Gly Ile Ile Gln Gly Glu Arg Asp His Tyr Gly Tyr Arg
                565                 570                 575
Gln Ser Val Thr Tyr Ala Cys Asn Lys Gly Phe Thr Met Ile Gly Glu
            580                 585                 590
His Ser Ile Tyr Cys Thr Val Asn Asn Asp Glu Gly Glu Trp Ser Gly
            595                 600                 605
Pro Pro Pro Glu Cys Arg Gly Lys Ser Leu Thr Ser Lys Val Pro Pro
        610                 615                 620
Thr Val Gln Lys Pro Thr Thr Val Asn Val Pro Thr Thr Glu Val Ser
625                 630                 635                 640
Pro Thr Ser Gln Lys Thr Thr Thr Lys Thr Thr Thr Pro Asn Ala Gln
                645                 650                 655
Ala Thr Arg Ser Thr Pro Val Ser Arg Thr Thr Lys His Phe His Glu
            660                 665                 670
Thr Thr Pro Asn Lys Gly Ser Gly Thr Thr Ser Gly Thr Thr
        675                 680                 685
```

COMPOSITIONS, METHODS AND KITS FOR TREATING COMPLEMENT RELATED DISORDERS

RELATED APPLICATIONS

This application claims the benefit of international application serial number PCT/US2015/047405 filed Aug. 28, 2015, which claims the benefit of U.S. provisional application having Ser. No. 62/043,084 filed Aug. 28, 2014 entitled, "Compositions, methods and kits for treating complement related disorders" with inventors Rajendra Kumar-Singh, Derek Leaderer, and Siobhan Cashman, each of which is hereby incorporated herein by reference in its entirety.

GOVERNMENT SUPPORT

This invention was made with government support under grants EY021805 and EY013837 awarded by the National Institutes of Health. The government has certain rights in the invention.

TECHNICAL FIELD

The present invention generally relates to compositions and methods to treat complement related disorders.

BACKGROUND

Complement system is a humoral component of innate immune system, which is responsible for inactivating invading pathogens and maintaining tissue homeostasis. (Thurman, J. M., et al. 2011 Lab Invest 91: 4-11) The complement system is potent and hence is tightly regulated by a variety of soluble and membrane bound inhibitors of complement (Thurman, J. M., et al. 2011 Lab Invest 91: 4-11, Zipfel, P. F., et al. 2009 Nat Rev Immunol 9: 729-740). Inappropriate activation of complement has been associated with a wide variety of inherited and acquired diseases, including autoimmune, inflammatory, hematological, neurodegenerative, cancer, ischemia/reperfusion injuries, organ transplantation and sepsis (Zipfel, P. F., et al. 2009 Nat Rev Immunol 9: 729-740, Makrides, S. C. 1998 Pharmacol Rev 50: 59-87, Holers, V. M. 2008 Immunol Rev 223: 300-316). Foreign surfaces present in biomaterials such as medical implants, hemodialysis filters and gene delivery systems also trigger activation of complement (Makrides, S. C. 1998 Pharmacol Rev 50: 59-87).

Acute activation of complement occurs in diseases such as sepsis or transplant rejection. However, majority of disorders associated with activation of complement are chronic, e.g. age related macular degeneration (AMD), paroxysmal nocturnal hemoglobinuria or rheumatoid arthritis (Zipfel, P. F., et al. 2009 Nat Rev Immunol 9: 729-740). A portion of the chronic diseases involving complement are caused by deficiencies in regulators of complement (Zipfel, P. F., et al. 2009 Nat Rev Immunol 9: 729-740). The deficiencies in complement regulator are primarily of the alternative pathway and can involve the classical pathway, such as in hereditary angioedema or systemic lupus erythematosus (SLE) (Mayilyan, K. R. 2012 Protein Cell 3: 487-496).

Activation of complement leads to formation of membrane attack complex (MAC), a pore that disrupts the cell membrane and subsequently lyses the cell (Walport, M. J. 2001 N Engl J Med 344: 1058-1066). Elevated levels of MAC coupled with polymorphisms or mutations in complement regulators are found in patients with chronic diseases such as AMD, indicating that failure at a variety of check points in complement activation are associated with disease pathogenesis (Mullins, R. F., et al. 2011 Exp Eye Res 93: 565-567). In cases individuals with AMD, the individuals with a reduced ability to form MAC are partially protected from disease pathogenesis without significant complications, supporting the premise that long-term attenuation of complement activation for chronic disorders may be a viable approach for the treatment of AMD and other complement-associated disorders such as rheumatoid arthritis (Nishiguchi, K. M., et al. 2012 Invest Ophthalmol Vis Sci 53: 508-512, Piccoli, A. K., et al. 2011 Rev Bras Reumatol 51: 503-510).

At the time the present application is filed, there are only few FDA-approved inhibitors of complement available to patients (Ricklin, D., and Lambris, J. D. 2013 J Immunol 190: 3839-3847). In the context of chronic disorders such as AMD, some of these therapeutic agents would require repeated injections of the complement inhibitor into the eye, a mode of delivery associated with significant side effects (Wu, L., et al. 2008 Graefes Arch Clin Exp Ophthalmol 246: 81-87, Shima, C., et al. 2008 Acta Ophthalmol 86: 372-376).

There is a need for inhibitors of complement to treat complement diseases such as AMD and liver disorders.

SUMMARY

An aspect of the invention provides a pharmaceutical composition for treating a complement-related condition in a subject including a recombinant chimeric protein having amino acid sequences from at least two of a CD46 protein, a CD55 protein, and a CD59 protein, or a nucleotide sequence encoding the recombinant chimeric protein, such that the recombinant chimeric protein negatively modulates classical and alternative complement pathways. In an embodiment of the composition, the recombinant chimeric protein is a soluble active complement terminator. In an embodiment of the composition, the nucleotide sequence encoding the amino acid sequence of the CD59 protein includes at least one mutation conferring loss of function of a glycosyl phosphatidyl inositol (GPI) anchoring domain, such that the mutation is at least one of a substitution, a deletion, and an addition. In an embodiment of the composition, the nucleotide sequence encoding the amino acid sequence of the CD55 protein includes at least one mutation conferring loss of function of a glycosyl phosphatidyl inositol (GPI) anchoring domain, such that the mutation is at least one of a substitution, a deletion, and an addition. In an embodiment of the composition, the nucleotide sequence encoding the amino acid sequence of the CD46 protein includes at least one mutation conferring loss of function of membrane spanning domain, such that the mutation comprises at least one of a substitution, a deletion, and an addition. In some embodiments, the composition is formulated in a dose effective to treat the subject for the complement-related condition. In some embodiments, the amino acid sequence of the CD59 protein comprises a secretory signal peptide.

In some embodiments of the composition, the protein further includes a linker connecting at least one of: amino acid sequences of the CD59 protein and the CD46 protein; amino acid sequences of the CD46 protein and the CD55 protein; and amino acid sequences of the CD55 protein and the CD59 protein. In another embodiment of the composition, the nucleotide sequence further encodes a linker including at least one amino acid for example a glycine, a serine, or an alanine. In an embodiment of the composition, the amino acid sequences of the CD46, CD55 and CD59 proteins are encoded by nucleic acid encoding a protein fusion in the same reading frame as a transcription fusion in which expression of the proteins is operably linked and expression.

In an embodiment of the composition, the CD46 protein amino acid sequence includes at least one of: a short consensus repeat domain and a serine/threonine/proline rich domain, or such that nucleotide sequence encoding the CD46 protein amino acid sequence includes at least one mutation, for example a substitution, a deletion or an addition resulting in loss of membrane spanning domain, or such that nucleotide sequence encoding CD55 protein amino acid sequence includes at least one mutation resulting in loss of function of a glycosyl phosphatidyl inositol (GPI) anchoring domain of the CD55 protein, the mutation including a substitution, a deletion, or an addition, or such that the CD55 protein amino acid sequence includes at least one of: a short consensus repeat domain and a serine/threonine/proline rich domain.

In an embodiment of the composition, the nucleotide sequence encoding the recombinant chimeric protein comprises a plasmid. In some embodiments, the nucleotide sequence includes a viral vector. In an embodiment of the composition, the vector is at least one selected from the group of: an adenovirus, an adeno-associated virus, a herpesvirus, a poxvirus, and a lentivirus. In some embodiments, the nucleotide sequence includes a promoter from a gene selected from the group consisting of: a beta actin for example a chicken beta actin, a peripherin/RDS, cGMP phosphodiesterase, and a rhodopsin. Some embodiments of the composition further includes a delivery vehicle engineered to target a cell or a tissue, the delivery vehicle selected from the group of: a liposome, a lipid, a polycation, a peptide, a nanoparticle, a gold particle, and a polymer. An embodiment of the composition further includes at least one of: a pharmaceutically acceptable salt or emollient. An embodiment of the composition further includes an agent selected from the group consisting of: anti-tumor, anti-coagulant, anti-viral, antibacterial, anti-mycobacterial, anti-fungal, anti-proliferative and anti-apoptotic.

An aspect of the invention provides a method of treating a complement-related condition in a subject including: contacting a cell of the subject with a composition including a CD46 protein, a CD55 protein, and a CD59 protein or a recombinant chimeric protein operably linked to a promoter sequence causing expression of the recombinant chimeric protein in a cell, such that the nucleotide sequence encodes amino acid sequences of each of the CD59 protein, the CD46 protein, and the CD55 protein, or the composition includes a vector carrying a nucleotide sequence encoding the CD46 protein, the CD55 protein, the CD59 protein or the recombinant chimeric protein; measuring symptoms of the complement-related condition in the subject; comparing symptoms of the subject to symptoms prior to contacting; and measuring a decrease in symptoms of the complement-related condition in the subject, thereby treating the complement-related condition. In an embodiment of the method, the recombinant chimeric protein is a soluble active complement terminator.

In an embodiment of the method, measuring includes measuring at least one of: an amount of a protein of a complement pathway, and an amount of Membrane attack complex. In an embodiment, measuring Membrane attack complex includes analyzing an amount of membrane attack complex in a cell such that the cell is selected from: muscular, epithelial, endothelial, and vascular, or such that the cell is selected from a tissue in at least one of: eye, heart, kidney, thyroid, brain, stomach, lung, liver, pancreas, and vascular system. In embodiments of the methods, the condition is selected from the group of: macular degeneration, age-related macular degeneration, inflammatory bowel disease, thyroiditis, cryoglobulinaemia, fetal loss, organ graft rejection, sepsis, viral infection, fungal infection, bacterial infection, toxic shock syndrome (TSS), membranoproliferative glomerulonephritis, dense deposit disease, peroximal nocturnal hemoglobinurea, lupus nephritis, membranous nephritis, immunoglobulin A nephropathy, goodpasture syndrome, post-streptococcal glomerulonephritis, systemic lupus erythematosus, atypical hemolytic uremic syndrome, systemic lupus erythromatosis, lupus arthritis, rheumatoid arthritis, Sjögren's syndrome, Behçet's syndrome, systemic sclerosis, Alzheimer's disease, multiple sclerosis, myasthenia gravis, Guillain-Barré syndrome, cerebral lupus, stroke, adult respiratory distress syndrome, chronic obstructive pulmonary disease, cystic fibrosis, haemolytic anaemia, paroxysmal cold haemoglobinuria, paroxysmal nocturnal haemoglobinuria, vasculitis, pemphigus, bullous pemphigoid, phototoxic reactions, psoriasis, anaphylactic shock, allergy, asthma, myocardial infarction, diabetic retinopathy, microvasculopathy, dermatomyositis, B-cell lymphoproliferative disorders, demyelinating disease, acute kidney injury, COPD, Rh disease, immune hemolytic anemia, immune thrombocytopenic purpura, Complement associated glomerulopathies, and atherosclerosis.

In some embodiments of the method, the cell is contacted in vitro or ex vivo or in vivo or in situ. In some embodiments, prior to contacting the cell, the method further includes engineering the vector carrying the nucleotide encoding the recombinant chimeric protein. In some embodiments of the method, engineering includes mutating nucleic acid encoding the CD55 protein amino acid sequence such that at least one mutation results in loss of function of glycosyl phosphatidyl inositol (GPI) anchoring domain, or such that engineering includes mutating nucleic acid encoding the CD46 protein amino acid sequence such that at least one mutation results in removal of a membrane spanning domain, or such that engineering includes mutating nucleic acid sequence encoding CD59 protein amino acid sequence such that at least one mutation results in loss of function of glycosyl phosphatidyl inositol (GPI) anchoring domain, or such that engineering includes recombinantly joining nucleic acid encoding the CD46 protein C-terminus with nucleic acid encoding amino acids of CD55 protein N-terminus, and recombinantly joining nucleic acid sequence encoding the CD55 protein C-terminus with nucleic acid encoding the CD59 protein N-terminus. In some embodiments, the mutation includes at least one of: a substitution, a deletion, and an addition. In some embodiments of the method, contacting the cell includes administering the composition by at least one route selected from the group consisting of: intravenous, intramuscular, intraperitoneal, intradermal, mucosal, subcutaneous, sublingual, intranasal, oral, intra-ocular, intravitreal, topical, transdermal, vaginal, and infusion.

An aspect of the invention provides a kit for regulating or of treating a complement-related condition in a subject, the method including: a composition comprising a recombinant chimeric protein including amino acid sequences from each of a CD46 protein, a CD55 protein, and a CD59 protein, or a nucleotide sequence encoding the recombinant chimeric protein, such that the composition negatively modulates classical and alternative complement pathways and is formulated in a dose effective to treat the subject for the complement-related condition; instructions for treating the subject; and, a container.

An aspect of the invention provides a pharmaceutical composition for treating a complement-related condition in a subject including a recombinant chimeric protein having amino acid sequences from a CD55 protein, and a CD59 protein, or a nucleotide sequence expressing the recombinant chimeric protein, such that the recombinant chimeric protein negatively modulates classical and alternative complement pathways.

An aspect of the invention provides a pharmaceutical composition for treating a complement-related condition in a subject including amino acid sequences from at least two of a CD46 protein, a CD55 protein, and a CD59 protein, or a first recombinant chimeric protein including amino acid sequences from each of a CD46 protein, a CD55 protein, and a CD59 protein, or a second recombinant chimeric protein having amino acid sequences from a CD55 protein, and a CD59 protein, or a nucleotide sequence expressing the first recombinant chimeric protein, or a nucleotide sequence expressing the second recombinant chimeric protein, such that the first or the second protein negatively modulates classical and alternative complement pathways.

An aspect of the invention provides a pharmaceutical composition for treating a complement-related condition in a subject including a first recombinant chimeric protein comprising amino acid sequences from each of a CD46 protein, a CD55 protein, and a CD59 protein, and a second recombinant chimeric protein having amino acid sequences from a CD55 protein, and a CD59 protein, or a nucleotide sequence expressing the first recombinant chimeric protein and a nucleotide sequence expressing the second recombinant chimeric protein, such that the first and the second recombinant chimeric proteins negatively modulate classical and alternative complement pathways.

An aspect of the invention provides a method of treating a complement-related condition in a subject including: contacting a cell of the subject with a composition including a CD55 protein, and a CD59 protein or a recombinant chimeric protein operably linked to a promoter sequence causing expression of the recombinant chimeric protein in a cell, such that the nucleotide sequence encodes amino acid sequences of each of the CD59 protein, and the CD55 protein, or the composition includes a vector carrying a nucleotide sequence encoding the CD55 protein, the CD59 protein or the recombinant chimeric protein; and, observing symptoms of the complement-related condition in the subject; comparing symptoms of the subject to symptoms prior to contacting; and observing a decrease in symptoms of the complement-related condition in the subject, thereby treating the complement-related condition. In an embodiment of the method, recombinant chimeric protein is a dual terminator of Active Complement.

In an embodiment of the method, measuring includes measuring at least one of an amount of a protein of a complement pathway, and Membrane attack complex. In an embodiment of the method, measuring Membrane attack complex includes analyzing an amount of membrane attack complex in a cell; such that the cell is selected from: muscular, epithelial, endothelial, and vascular, or such that the cell is selected from a tissue in at least one of: eye, heart, kidney, thyroid, brain, stomach, lung, liver, pancreas, and vascular system. In embodiments of the methods, the condition is selected from the group of: macular degeneration, age-related macular degeneration, inflammatory bowel disease, thyroiditis, cryoglobulinaemia, fetal loss, organ graft rejection, sepsis, viral infection, fungal infection, bacterial infection, toxic shock syndrome (TSS), membranoproliferative glomerulonephritis, dense deposit disease, peroximal nocturnal hemoglobinurea, lupus nephritis, membranous nephritis, immunoglobulin A nephropathy, goodpasture syndrome, post-streptococcal glomerulonephritis, systemic lupus erythematosus, atypical hemolytic uremic syndrome, systemic lupus erythromatosis, lupus arthritis, rheumatoid arthritis, Sjögren's syndrome, Behçet's syndrome, systemic sclerosis, Alzheimer's disease, multiple sclerosis, myasthenia gravis, Guillain-Barré syndrome, cerebral lupus, stroke, adult respiratory distress syndrome, chronic obstructive pulmonary disease, cystic fibrosis, haemolytic anaemia, paroxysmal cold haemoglobinuria, paroxysmal nocturnal haemoglobinuria, vasculitis, pemphigus, bullous pemphigoid, phototoxic reactions, psoriasis, anaphylactic shock, allergy, asthma, myocardial infarction, diabetic retinopathy, microvasculopathy, dermatomyositis, B-cell lymphoproliferative disorders, demyelinating disease, acute kidney injury, COPD, Rh disease, immune hemolytic anemia, immune thrombocytopenic purpura, Complement associated glomerulopathies, and atherosclerosis.

In alternative embodiments of the method, the cell is contacted in vitro, ex vivo, or in vivo, and if in vivo, possibly also in situ. In some embodiments, prior to contacting the cell, the method further includes engineering the vector carrying the nucleotide encoding the recombinant chimeric protein. In some embodiments of the method, engineering includes mutating nucleic acid encoding the CD55 protein amino acid sequence such that at least one mutation results in loss of function of glycosyl phosphatidyl inositol (GPI) anchoring domain, or such that engineering includes mutating nucleic acid encoding the CD46 protein amino acid sequence such that at least one mutation results in removal of a membrane spanning domain, or such that engineering includes mutating nucleic acid sequence encoding CD59 protein amino acid sequence such that at least one mutation results in loss of function of glycosyl phosphatidyl inositol (GPI) anchoring domain, or such that engineering includes recombinantly joining nucleic acid encoding the CD46 protein C-terminus with nucleic acid encoding amino acids of CD55 protein N-terminus, and recombinantly joining nucleic acid sequence encoding the CD55 protein C-terminus with nucleic acid encoding the CD59 protein N-terminus. In some embodiments, the mutation includes at least one of: a substitution, a deletion, and an addition. In some embodiments of the method, contacting the cell includes administering the composition by at least one route selected from the group consisting of: intravenous, intramuscular, intraperitoneal, intradermal, mucosal, subcutaneous, sublingual, intranasal, oral, intra-ocular, intravitreal, topical, transdermal, vaginal, and infusion.

BRIEF DESCRIPTION OF FIGURES

FIG. 1A and FIG. 1B are a schematic drawing and a photograph showing structure and expression of SACT and DTAC.

FIG. 1A is a schematic drawing of the structure of the human membrane-associated complement regulators CD46, CD55 and CD59 and the soluble recombinant proteins SACT and DTAC. Both CD55 and CD46 each contain four short consensus repeat (SCR) domains and a serine/threonine (S/T) rich region. The SCR and S/T domains are sites of N- and O-linked glycosylation, respectively. CD46 inserts in the membrane via a hydrophobic domain, and CD55 and CD59 each attach to the membrane via a glycophosphatidylinositol (GPI) anchor. CD59 contains a short functional unit of 76 amino acids. Both SACT and DTAC contain the four SCR domains and the S/T-rich region of human CD55 separated by a poly glycine linker from the functional domain of human CD59. SACT additionally contains the four SCR domains of human CD46 at the N-terminus separated by a polyglycine linker from the SCRs of CD55. Both SACT and DTAC contain a secretory signal derived from human CD59. In engineering the recombinant proteins the membrane-spanning domain of CD46 and the signals for attachment of a GPI-anchor to each of CD55 and CD59 were not included.

FIG. 1B is a photograph of a western blot showing media from cells transfected with pDTAC, pGFP or pSACT probed with antibodies against CD46, CD55 and CD59.

FIG. 2A is a schematic drawing of Factor I cleavage of C3b. C3b consists of two polypeptide chains (α' and β), joined by a disulfide linkage. Factor I mediates cleavage of the 104 kDa α' chain into inactive fragments, iC3bH and iC3bL.

FIG. 2B is a schematic drawing showing CD46 binding of C3b deposited on the cell membrane to act as a co-factor for Factor I-mediated cleavage to inactive iC3b.

FIG. 2C is a photograph of a western blot of purified C3b incubated in media from cells transfected with either pSACT, pDTAC or pGFP in the presence or absence of Factor I and probed with an antibody specific for C3. The western blot shows increased cleavage of the α' chain in the presence of media from cells transfected with pSACT compared to cleavage occurred in the presence of either pGFP or pDTAC.

FIG. 2D is a bar graph of quantification of western blot data showing a 51.8±10.5% (p=0.007) and 46.2±4.8% (p=0.0007) reduction in the amount of the α' chain of C3b in media from pSACT-transfected cells containing C3b and Factor I compared to media from pGFP-transfected cells and pDTAC-transfected cells containing C3b and Factor I, respectively. The signal intensities for the α' chain were normalized to the signal intensity of the β chain.

FIG. 3A, FIG. 3B and FIG. 3C are a schematic drawing and bar graphs showing that SACT and DTAC accelerate degradation of C3 convertase.

FIG. 3A is a schematic drawing of dissociation of CD55 and factor B binding to C3b to accelerate degradation of the C3 convertase.

FIG. 3B is a bar graph of quantification of immunostaining of Factor B binding to agarose-bound C3b using an antibody for Factor B. The graph shows that media from pDTAC- or pSACT-transfected cells resulted in a 16.1±6.4% (p=0.0214, n=11) and 16.8±6.1% (p=0.0127, n=11) reduction in C3b-bound Factor B, respectively, compared to media from pGFP-transfected cells (n=10). The Factor B binding is presented as % staining relative to the average staining intensity of Factor B bound to C3b in the presence of media from pGFP-transfected cells.

FIG. 3C is a bar graph of quantification of human complement-mediated lysis of sheep erythrocytes that were incubated with media from cells transfected with either pDTAC or pSACT in the presence or absence of CD55 blocking antibody. A significant reduction in protection against cell lysis was observed for both DTAC and SACT in the presence of antibody.

FIG. 4A is a schematic drawing of CD59 function. CD59 binds to the membrane-associated C5b-8 protein complex, preventing incorporation of C9 and formation of the membrane attack complex (MAC). MAC forms a pore on the cell surface, reducing integrity of the membrane.

FIG. 4B is a bar graph of quantification of lysis of sheep erythrocytes by C9-depleted human serum incubated with C9 in the presence of media transfected with pGFP, pDTAC or pSACT. Media from pDTAC- and pSACT-transfected cells reduced human complement-mediated lysis of erythrocytes by 34.8±3.6% (p<0.0001) and 29.9±4.6% (p<0.0001), respectively, compared to erythrocytes incubated in the presence of media from pGFP-transfected cells.

FIG. 5A is a bar graph of quantification of lysis of sheep erythrocytes (hemolysis) by human serum in the presence of media from cells transfected with pGFP, pDTAC or pSACT shows a 47±2.9% (p<0.0001) and 21.5±2.8% (p<0.0001) reduction in lysis by DTAC and SACT, respectively, compared to media from the GFP-transfected cells.

FIG. 5B is a graph of quantification of propidium iodide (PI) uptake by murine hepatocytes incubated with normal human serum (NHS) in the presence of media from cells transfected with pGFP, pDTAC or pSACT. Control sample of hepatocytes incubated with heat-inactivated NHS (hiNHS) in the presence of media from pGFP-transfected cells is also shown. Hepatocytes incubated with media from pDTAC- or pSACT-transfected cells were observed to have 28.73%±10.21% (p=0.014, n=8) or 20.8±9.0% (p=0.037, n=8) reduction in PI uptake, respectively compared to hepatocytes incubated with media from pGFP-transfected cells (n=7).

FIG. 6A is a set of fluorescent micrographs of murine hepatocytes incubated with NHS in the presence of media from pGFP-, pDTAC- or pSACT-transfected cells. Cells were stained with an antibody for MAC or for DAPI.

FIG. 6B graphs the quantification of MAC staining intensity/area, and shows a 53.8±10.4% (p=0.0004, n=6) or 67.8±9.2% (p<0.0001, n=6) reduction in MAC deposition on murine hepatocytes incubated with media from cells transfected with pDTAC or pSACT, respectively, compared to hepatocytes incubated with media from pGFP-transfected cells (n=6). Control sample of hepatocytes incubated with hiNHS in the presence of media from pGFP-transfected cells is also shown. DAPI, 4',6-diamidino-2-phenylindole; MAC, membrane attack complex; hiNHS, heat-inactivated normal human serum.

FIG. 7A, FIG. 7B, FIG. 7C and FIG. 7D are micrographs and bar graphs showing that DTAC protects murine liver vasculature from human MAC deposition in vivo.

FIG. 7A is a set of fluorescent micrographs of cryosections showing AAV2/8GFP transduction of murine liver. Efficient transduction was observed throughout the tissue. Higher magnification of boxed region is also shown.

FIG. 7B is a set of fluorescent micrographs of liver cryosections stained with anti-MAC antibody harvested from mice injected in the intraperitoneal space with AAV2/

8pA or AAV2/8DTAC and perfused with mPECAM1 antibody and NHS. Higher magnification of boxed regions is also shown.

FIG. 7C is a set of bar graphs of quantification of MAC staining intensity (IU) of liver sections, showing a 56.7±16.4% (p=0.0061) reduction in human MAC deposition on the liver vasculature of AAV2/8DTAC-injected relative to AAV2/8polyA-injected mice.

FIG. 7D is a bar graph of quantification of MAC staining intensity per area of blood vessels which shows a 55.6±11.3% (p=0.0006) reduction in human MAC deposition in livers of AAV2/8DTAC-injected mice compared to AAV2/8polyA-injected. Staining intensity was averaged from 8 sections per mouse. n=6 for AAV2/8polyA- and n=6 for AAV2/8DTAC-injected mice. (DIC: differential interference contrast; IU: intensity unit)

FIG. 8A, FIG. 8B and FIG. 8C are micrographs and bar graphs showing that SACT protects murine liver vasculature from human MAC deposition in vivo.

FIG. 8A is a set of fluorescent micrographs of liver cryosections stained with anti-MAC antibody harvested from mice injected in the intraperitoneal space with AAV2/8pA or AAV2/8SACT and perfused with mPECAM1 antibody and NHS. Higher magnification of boxed regions is also shown.

FIG. 8B is a bar graph of quantification of MAC staining intensity (IU) of liver sections which shows a 63.2%±20.5% (p=0.0075) reduction in human MAC deposition on the liver vasculature of AAV2/8SACT-injected compared to AAV2/8polyA-injected mice.

FIG. 8C is a bar graph of quantification of MAC staining intensity per area of blood vessels which shows a 61.1±18.9% (p=0.0056) reduction in human MAC deposition on the blood vessels of AAV2/8SACT-injected relative to AAV2/8polyA-injected mice. Staining intensity was averaged from 8 sections per mouse. n=8 for AAV2/8polyA- and n=9 for AAV2/8SACT-injected mice.

Figure 9:
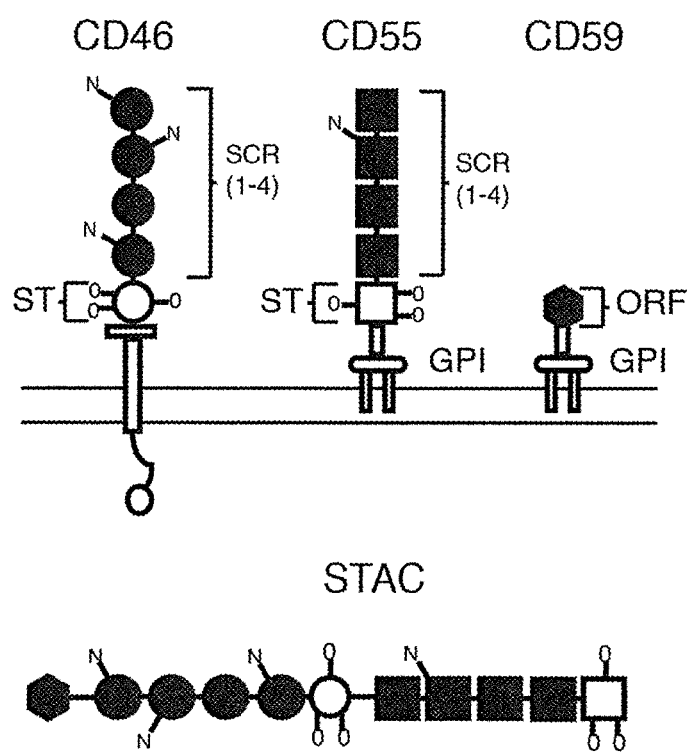

FIG. 9 is a schematic drawing of structures of soluble terminator of activated complement (STAC) showing the structure of the human membrane-associated complement regulators, CD46, CD55 and CD59 and the soluble recombinant protein STAC. STAC contains a secretory signal derived from human CD59. The four SCR domains and S/T-rich region of human CD46 were attached via a poly glycine linker to CD59. The four SCR domains and the S/T-rich region of human CD55 were engineered to be separated by a poly glycine linker from the functional domain of human CD46.

Figures 10A, 10B:
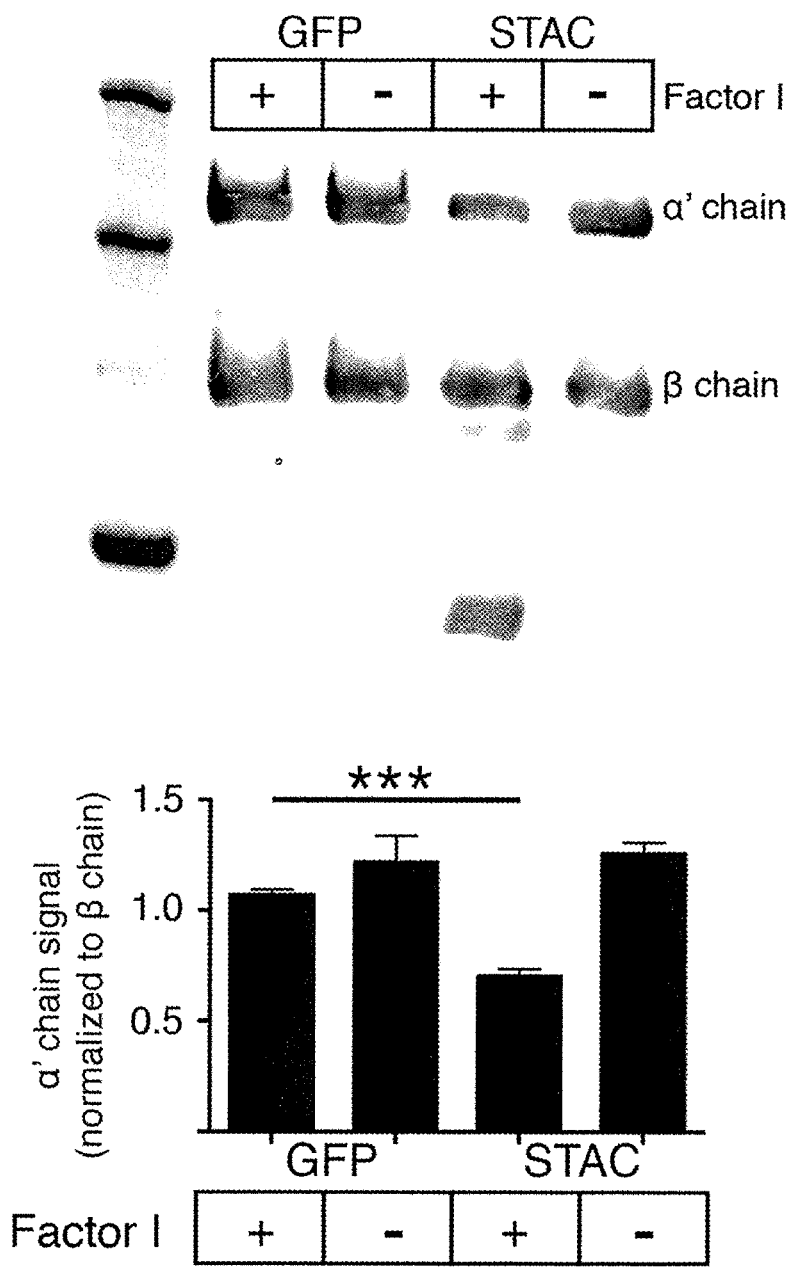

FIG. 10A and FIG. 10B are a photograph and a bar graph showing that STAC acts as a co-factor for Factor I mediated cleavage of C3b.

FIG. 10A is a photograph of a western blot of purified C3b incubated in media obtained from cells transfected with either pAdCAGGFP or with pAdCAGSTAC in the presence or absence of Factor I and probed with an antibody for C3. The data shows increased cleavage of α' chain in the presence of media from cells transfected with pAdCAG-STAC compared to cleavage that occurred in the presence of pAdCAGGFP.

FIG. 10B is a graph of quantification of western blot data which shows a 34.3%±3.9% (n=4; p=0.0001) reduction in the amount of the C3b α' chain in media from pAdCAG-STAC-transfected cells containing C3b and Factor I compared to media from pAdCAGGFP-transfected cells containing C3b and Factor I (n=4). The signal intensities for the α' chain were normalized to the signal intensity of the β chain.

Figure 11:
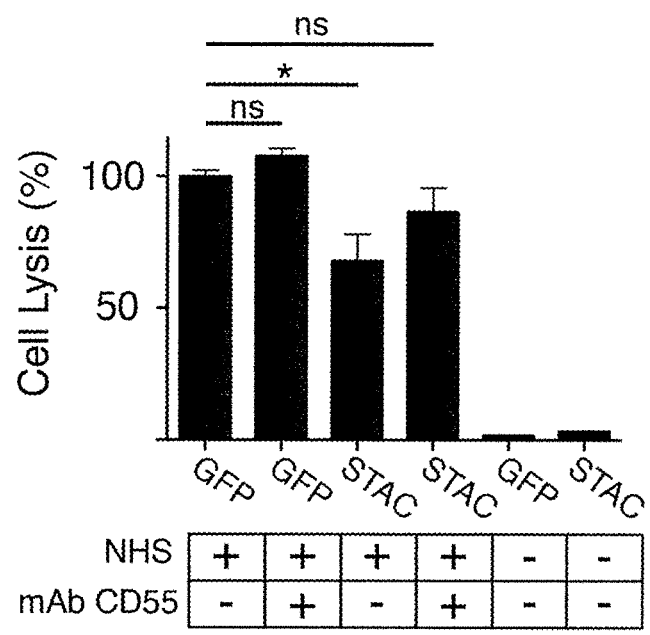

FIG. 11 is a bar graph showing that the CD55 portion of STAC retains functionality. The graph illustrates quantification of human complement-mediated lysis of sensitized sheep erythrocytes which were incubated with media from cells transfected with either pAdCAGGFP or pAdCAG-STAC in the presence or absence of CD55 blocking antibody. STAC treated samples in the absence of mAb blocking were observed to have a 32.1%±10.4% reduction in cell lysis (n=6, p=0.0115) compared to GFP treated samples (n=6) with no antibody blocking. Sheep erythrocytes suspended in media from pAdCAGSTAC transfected cells containing CD55 blocking antibody showed a non-statistically significant reduction of 13.4%±9.4% in cell lysis (n=6; p=0.1831). Cell lysis that occured in GFP media without blocking antibody was set to 100% cell lysis.

Figure 12:
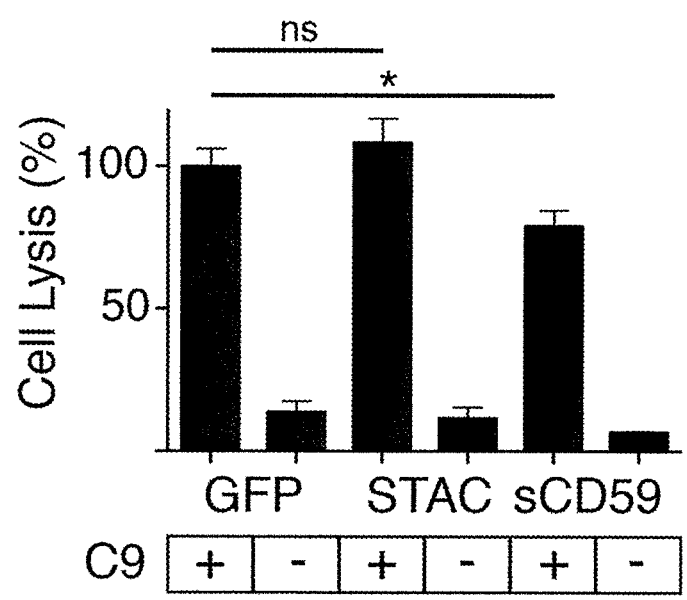

FIG. 12 is a bar graph showing that STAC was unable to prevent C9 incorporation into membrane attack complex. The graph is a quantification of lysis of sheep erythrocytes by C9-depleted human serum incubated with or without C9 in the presence of media transfected with pAdCAGGFP, pAdCAGSTAC or pAdCAGsCD59 (positive control). Erythrocytes treated with sCD59+C9 were observed to have a 21%±9.1% (n=8; p=0.033) reduction in cell lysis compared to GFP+C9 treated cells (n=14). Samples treated with STAC+C9 showed no decrease in cell lysis (n=14; p=0.428).

DETAILED DESCRIPTION

A variety of disorders are associated with the activation of complement. CD46, CD55 and CD59 are the major membrane associated regulators of complement on human cells. Independent expression of CD55, CD46 or CD59 through gene transfer protects murine tissues against human complement mediated attack. The example of the present application describe the potential of combining the complement regulatory properties of CD46, CD55 and CD59 into single gene products expressed from an adeno associated virus (AAV) vector in a soluble non-membrane anchored form.

Dysregulation of the complement system is one of the major factors contributing towards the etiology of AMD, one of the leading causes of blindness in the elderly (Gehrs et al. 2010 Arch Ophthalmol 128: 349-358). The most devastating form of the disease affects approximately 10% of patients (Klein 2008 Ophthalmology 115: 1026-1031), and involves the growth of attenuated blood vessels from the choroidal vasculature through Bruch's membrane and into the retina. The plasma released by these "ill-formed" vessels damages photoreceptors and other retinal cells, eventually leading to a severe loss of vision. The vast majority of AMD patients, however, present with extracellular deposits which occur between the retinal pigment epithelium (RPE) and Bruch's membrane called drusen and which eventually lead to atrophy of the RPE (geographic atrophy).

A potential role for complement in AMD was considered because complement proteins were identified in drusen of AMD eyes (Johnson et al. 2001 Exp Eye Res 73: 887-896; Johnson et al. 2000 Exp Eye Res 70: 441-449; Mullins et al. Eye (Lond) 15: 390-395; and Mullins et al. 2000 FASEB J 14: 835-846). Polymorphisms have been identified in a number of complement genes and were observed to be either strongly predictive of or protective against AMD. A single amino acid change, Y402H, in factor H accounts for as much as 40-50% of AMD in aging eyes (Edwards et al. 2005 Science 308: 421-424; Hageman et al. 2005 Proc Natl Acad Sci USA 102: 7227-7232; and Haines et al. 2005 Science 308: 419-421).

Haplotype variants in both Factor B and complement component 2 (C2) result in a significantly reduced risk of developing AMD (Gold et al. 2006 Nat Genet 38: 458-462), and an R80G substitution in complement component 3 (C3) increased the risk of having AMD to as much as 22% (Yates et al. 2007 N Engl J Med 357: 553-561). The factor B (32Q) variant has been shown to have a 4-fold lower binding affinity for C3b, with a reduced ability to form the convertase (Montes et al. 2009 Proc Natl Acad Sci USA 106: 4366-4371). In addition, polymorphisms in C2, C3, and factor B have been shown to be significantly linked with progression to both types of advanced AMD disease, choroidal neovascularization and geographic atrophy (Klein 2008 Ophthalmology 115: 1026-1031; Maller et al. 2007 Nat Genet 39: 1200-1201; and Reynolds et al. 2009 Invest Ophthalmol Vis Sci 50: 5818-5827).

Deposition of complement proteins has been observed in the choriocapillaris of patients with diabetic retinopathy (Gerl et al. 2002 Invest Ophthalmol Vis Sci 43: 1104-1108), and in retinal vessels of diabetic subjects (Zhang et al. 2002 Diabetes 51: 3499-3504). The retinal vessels exhibited a significant reduction in expression of complement regulatory proteins CD55 and CD59. Complement components have also been observed in the epiretinal membranes of patients suffering from proliferative vitreoretinopathy (PVR), and upregulation of the classical pathway initiator protein, C1q, and altered expression of other proteins of the cascade have been observed in glaucomatous eyes (Baudouin et al. 1990 Am J Ophthalmol 110: 593-598; Stasi et al. 2006 Invest Ophthalmol Vis Sci 47: 1024-1029; and Tezel et al. 2010 Invest Ophthalmol Vis Sci 51(11): 5697-707).

There are few animal models that are useful to directly investigate the role of complement in retinal function and pathology. Most of these models have been used to analyze the impact of different complement proteins in the development of laser-induced choroidal neovascularization (CNV) in the mouse retina. Other studies have demonstrated the dependence of retinal pathology on the alternative pathway, rather than classical or lectin pathway, and on the formation of the membrane attack complex (Bora et al. 2007 J Immunol 178: 1783-1790; Bora et al. 2006 J Immunol 177: 1872-1878; and Bora et al. 2005 J Immunol 174: 491-497). Previous studies have demonstrated a significant role played by the anaphylatoxins, C3a and C5a, in the development of CNV (Nozaki et al. 2006 Proc Natl Acad Sci USA 103: 2328-2333). Aged mice with deficiency of factor H exhibited altered architecture in Bruch's membrane, RPE and photoreceptors, and reduced ERGs (Coffey et al. 2007 Proc Natl Acad Sci USA 104: 16651-16656), and manifested a loss of integrity of retinal vessels (Lundh von Leithner et al. 2009 Am J Pathol 175: 412-421). The alternative complement pathway has been implicated also as a major factor in light-induced retinal degeneration which has been shown to be significantly reduced in a mouse deficient in Factor D (Rohrer et al. 2007 Invest Ophthalmol Vis Sci 48: 5282-5289). Ganglion cells of C3-deleted mice exhibited transient, but significant, protection from degeneration due to retinal ischemia reperfusion (Kuehn et al. 2008 Exp Eye Res 87:89-95).

One of three distinct complement pathways (classical, lectin or alternative) initiates the complement cascade (Markiewski et al. 2007 Am J Pathol 171: 715-727) and these pathways converge at the point in the pathway of the breakdown of C3 into C3a and C3b. The breakdown of C3 initiates the final part of the pathway that culminates in the formation of the membrane attack complex (MAC), a pore-like structure that inserts in the membranes of self- or non-self cells causing their lysis. In addition to the potential for cell lysis by the production of the opsonin C3b, activation of C3 generates the anaphylatoxins, C3a and C5a, both of which are powerful and pleiotropic effectors of inflammation. Unlike the classical or lectin pathways, the alternative pathway is constitutively active with small amounts of C3 hydrolysis and conversion to the convertase occurring in the serum.

An approach for delivery of inhibitors of complement for chronic diseases such as AMD or rheumatoid arthritis is the use of somatic gene therapy. Gene therapy is efficacious in humans for treatment of single gene disorders and patients with complex disorders such as rheumatoid arthritis have also been successfully treated using a gene therapy approach (Ginn, S. L., et al. 2013 J Gene Med 15: 65-77). Use of gene therapy has been found to be uniquely efficacious in mobilizing soluble versions of otherwise membrane-associated inhibitors of complement. For example, CD59 (protectin) is a naturally occurring inhibitor of MAC found tethered to the membranes of cells via a glycosylphosphatidylinositol (GPI) anchor. Membrane-associated CD59 is a potent inhibitor of MAC and soluble membrane-independent CD59 has been reported to be efficacious in vivo only when delivered via a gene therapy vector such as adeno-associated virus (AAV) (Cashman, S. M., et al. 2011 PLoS One 6: e19078).

CD55 (decay accelerating factor) is a GPI anchored protein that regulates complement activity by accelerating the decay of the classical as well as the alternative C3 convertase (Walport, M. J. 2001 N Engl J Med 344: 1058-1066). CD46 (membrane cofactor protein), is a ubiquitously expressed type 1 transmembrane glycoprotein which acts as a cofactor for factor I mediated cleavage of C3b and C4b and prevents formation of the classical and alternative C3 convertase (Riley-Vargas, R. C., et al. 2004 Immunol 25: 496-503). CD46 regulates amplification loop of the alternative pathway of activation of complement. CD55 and CD46 have different properties and each contain a series of 60 amino acid repeat motifs called short consensus repeats (SCR) that act as complement regulatory modules (Coyne, K. E., et al. 1992 J Immunol 149: 2906-2913). Species specificity between human and mouse complement proteins limits the testing of human complement inhibitors in murine tissues in vivo (Kim, D. D., et al. 2006 Clin Immunol 118: 127-136). The methods and compositions provided herein relate to engineering a novel non-membrane associated recombinant protein for optimal inhibition of complement activation. This is achieved by simultaneous targeting of both the classical and alternative pathways of complement and at different points of the complement cascade. The classical and alternative pathways of complement are targeted by combining the properties of CD55, CD46 and CD59. The examples herein describe the synthesis of the novel engineered recombinant protein and measure merits of its ability to inhibit human complement in cell culture and human complement in murine tissues in vivo by gene therapy. The examples herein also describe a recombinant protein that combines the complement inhibitory properties of CD55 and CD59.

A non-membrane associated recombinant molecule, SACT is provided herein that exhibits the combinatorial properties of CD46, CD55 and CD59. SACT is a secreted protein that can act as a co-factor for Factor I mediated cleavage of C3b, accelerate the degradation of C3 convertase, attenuate recruitment of C9 into the MAC, protect cells from human complement mediated lysis and inhibit deposition of human MAC on mouse cells in vitro and in vivo. Also provided herein is a composition DTAC which was observed to have the combined properties of CD55 and CD59, and which does not act as a co-factor for Factor I mediated cleavage of C3b.

Complement is a critical first line of immune defense in vertebrates, affording protection against both foreign organisms and the threat of damaged self-cells (Walport, M. J. 2001 N Engl J Med 344: 1058-1066). Over-expression of complement regulators for the treatment of complement-mediated pathologies poses risks as well as benefits. Therefore, the complement pathway at the combined points of C3 convertase formation and decay and the formation of MAC was inhibited, which allows C1q to interact with modified self and non-self surfaces, permitting C3b-mediated phagocytosis of offending cells and organisms (Trouw, et al. 2008 Mol Immunol 45: 1199-1207). The functions of CD55, CD46 and CD59 were combined into a single engineered protein, SACT. Further, because CD46 functions at the level of C3b degradation and CD55 prevents formation or accelerates the decay of convertases without altering C3b, it is here envisioned that CD46 interferes with C3b-mediated elimination of target cells. This may be especially important for the treatment of lupus-like diseases where reduced clearance of apoptotic cells can result in an autoimmune response to the dying cells (Trouw, et al. 2008 Mol Immunol 45: 1199-1207). Studies of the diversity of genetic factors involved in SLE, provide a comprehensive illustration of the importance of maintaining the potential for activation of upstream components of the cascade and blocking downstream events (Karp, D. R. 2005 Curr Opin Rheumatol 17: 538-542). Therefore a second recombinant molecule that includes only CD55 and CD59 functions, DTAC was generated and tested.

A gene therapy approach was used to deliver SACT or DTAC to cells in culture or to murine livers in vivo. Significant progress in the field of gene therapy indicates that this is a viable approach for the treatment of inherited or acquired diseases. Activation of complement plays a significant role in many disorders including rheumatoid arthritis, a chronic disease of the complement system. Elevated levels of C3 and MAC and reduced levels of CD59 have been documented in the synovial tissue of rheumatoid arthritis patients (Kemp, P. A., et al. 1992 J Clin Lab Immunol 37: 147-162, Konttinen, Y. T., et al. 1996 Ann Rheum Dis 55: 888-894). These studies are further supported by the observation that injection of rat knee joints with monoclonal antibody against CD59 results in spontaneous and acute arthritis and an increase in joint pathology in CD59 −/− mice, a phenotype that can be corrected by use of a membrane-targeted recombinant CD59 (Kemp, P. A., et al. 1992 J Clin Lab Immunol 37: 147-162). Attenuation of complement activation by targeting C5 was found to be effective in a murine model of rheumatoid arthritis, indicating that there are multiple points of the complement cascade that may serve as targets for complement based therapeutics (Kemp, P. A., et al. 1992 J Clin Lab Immunol 37: 147-162). Therefore, SACT and DTAC each are particularly effective inhibitors of complement activation because they concomitantly target and attenuate various points of the complement cascade. Even though repeat injections of inhibitors of complement activation into patients with rheumatoid arthritis is feasible, a long-lasting single injection via gene therapy is potentially preferred for efficiency and for convenience of the patient. Adeno-associated virus (AAV) has been shown to persist in humans for years and for over a decade in large animals (Colella, P., et al. 2009 Trends Mol Med 15: 23-31, Jiang, H., et al. 2006 Mol Ther 14: 452-455). Furthermore, AAV is not associated with any known human disease.

A strong case for delivery of inhibitors of complement via a gene therapy approach may be made for diseases such as AMD. Approximately 50% of patients that suffer from AMD have polymorphisms in the complement regulator Factor H (Klein, R. J., et al. 2005 Science 308: 385-389). Individuals that are homozygous for a Y402H polymorphism in Factor H have approximately 70% more MAC in their choroidal blood vessels and retinal pigment epithelium (RPE) (Mullins, R. F., et al. 2011 Exp Eye Res 93: 565-567). Individuals with an advanced form of AMD known as geographic atrophy have reduced levels of complement inhibitors on their RPE (Ebrahimi, K. B., et al. 2013 J Pathol 229: 729-742). A commonly occurring polymorphism in C9 in the Japanese population that prevents those individuals from efficiently assembling MAC is protective against the progression of AMD, suggesting that inactivation of complement via a gene therapy approach may be a viable avenue for treatment of this disease (Nishiguchi, K. M., et al. 2012 Invest Ophthalmol Vis Sci 53: 508-512).

However, all of the inhibitors of complement activation currently in clinical trials are small molecules, aptamers or antibodies that would need to be re-injected on a frequent basis into the eye of AMD patients (Keane, P. A., et al. 2012 J Ophthalmol 2012: 483034). These inhibitors have significant side effects such as increased intraocular pressure, endophthalmitis and retinal detachment (Wu, L., et al. 2008 Graefes Arch Clin Exp Ophthalmol 246: 81-87, Shima, C., et al. 2008 Acta Ophthalmol 86: 372-376). A single injection that may produce a therapeutic protein locally for an extended time such as an AAV vector, which mediates expression of SACT or DTAC, may be particularly attractive for treatment of diseases such as AMD. Species restriction between complement proteins limits the testing of human CD55 and human CD46 with respect to murine complement and thus in murine models of AMD (Kim, D. D., et al. 2006 Clin Immunol 118: 127-136). Inventors of the present application have shown that human CD55 or human CD46 efficiently inhibited human complement deposited on murine retinal tissues in ex vivo murine models of MAC deposition (Sweigard, J. H., et al. 2011 Gene Ther 18: 613-621).

At present, there are more than 25 small molecules, antibodies or proteins under clinical and preclinical development for attenuation of activation of complement. These molecules are aimed at a wide variety of indications including acute kidney injury, COPD, paroxysmal nocturnal hemoglobinuria, rheumatoid arthritis, sepsis, AMD and transplantation. The majority of these therapeutics target complement at the level of C3 or C5 (Ricklin, D., et al. 2013 J Immunol 190: 3839-3847). Mutations in CD46 have been shown to predispose individuals to familial hemolytic uremic syndrome (Kavanagh, D., et al. 2008 Annu Rev Med 59: 293-309). Deficiency of CD55 has been associated with primary autoimmune hemolytic anemia, SLE and in paroxysmal nocturnal hemoglobinuria (Richaud-Patin, Y., et al. 2003 Immunol Lett 88: 95-99, Iwamoto, N., et al. 1995 Blood 85: 2228-2232). CD55 has also been shown to attenuate ischemic reperfusion organ damage (Weeks, C., et al. 2007 Clin Immunol 124: 311-327). Mutations or deficiencies in CD59 have been shown to result in chronic hemolysis and relapsing peripheral demyelinating disease in infancy, paroxysmal nocturnal hemoglobinuria, autoimmune hemolytic anemia or SLE (Iwamoto, N., et al. 1995 Blood 85: 2228-2232, Nevo, Y., et al. 2013 Blood 121: 129-135). It is here envisioned that complement inhibitors such as SACT and DTAC will be useful for the treatment of these disorders.

Fodor et al. have described a membrane-associated recombinant molecule containing the combinatorial properties of CD55 and CD59 (Fodor, W. L., et al. 1995 J Immunol 155: 4135-4138). Similarly, Kroshus et al. have described a soluble molecule combining the properties of CD46 and CD55 and demonstrated that this molecule could reduce acute cardiac tissue injury in a pig-to-human transplant model (Kroshus, T. J., et al. 2000 Transplantation 69: 2282-2289). A recombinant protein comprised of select domains from CR2 and factor H demonstrated increased survival, reduced autoantibody production and improved kidney function in a murine model of lupus (Sekine, H., et al. 2011 Arthritis Rheum 63: 1076-1085). However, none of these studies delivered the recombinant protein via a gene therapy approach.

For in vivo examples herein an AAV2 pseudotyped with AAV8 capsid (AAV2/8) was used. This vector has been shown to have a very high efficiency of transduction of the liver of mice (Paneda, A., et al. 2009 Hum Gene Ther 20: 908-917). The in vivo examples were performed in the liver in part because large amounts of human MAC can readily form on murine liver (Gandhi, J., et al. 2011 PLoS One 6: e21621). Further, the liver was selected in part because hepatocytes are responsible for the biosynthesis of 80-90% of the plasma components of complement (Qin, X., et al. 2006 Cell Mol Immunol 3: 333-340). Finally, the liver receives 25% of total blood flow, allowing for a wide distribution of DTAC and SACT throughout the circulatory system, which would be relevant for the treatment of systemic disorders involving activation of complement (Myers, J. D., et al. 1948 J Clin Invest 27: 620-627). Expression of DTAC and SACT in vivo indicated that both are potent inhibitors of human complement in an in vivo setting and the data shown in examples herein lends support to the therapeutic value of these molecules if secreted from the liver.

To investigate whether the order of the complement regulatory regions affects functional capability the proteins provided herein were assayed in comparison to soluble terminator of activated complement (STAC), U.S. Pat. No. 8,877,896 issued Nov. 4, 2014. STAC contains the following: N-terminus of STAC contains the human CD59 start codon, secretory signal peptide and SCR domain; a polyglycine linker attaches the four SCR domains and S/T-rich region of human CD46 to the C-terminus of CD59; and four SCR domains and S/T-rich region of human CD55 are linked to the C-terminus of CD46 via a polyglycine sequence (FIG. 9). The c-DNA for STAC was prepared the protein was expressed between a CMV enhancer/chicken β-actin promoter (CAG) and a rabbit globin polyadenylation (pA) termination sequence. (Ibid.)

The functionality of each of the CD46, CD55 and CD59 components was individually measured in STAC as described in examples herein. It was observed that the CD59 portion in STAC was non-functional. CD59 is a potent inhibitor of the terminal pathway of the complement system (Rollins S A, et al., J Immunol. 1990; 144 (9):3478-83). CD59 functions by blocking C9 incorporation into the membrane attack complex (MAC), thereby blocking pore formation in cellular membranes (Rollins S A, et al., J Immunol. 1990; 144 (9):3478-83). The CD59 portion of STAC was observed to be unable to prevent C9 incorporation. Therefore, the CD59 portion of STAC is non-functional and hence this portion of STAC does not contribute function as an inhibitor of complement.

The invention herein provides a functional non-membrane associated recombinant protein, SACT, which exhibits the combinatorial properties of CD46, CD55 and CD59, and also provides a recombinant protein DTAC, which has the combinatorial properties of CD55 and CD59. Each of these proteins were observed to surprisingly exhibit properties and functions of their modular components and each of these proteins is a potent inhibitor of activation of complement in vitro and in vivo. Each of the components of the SACT protein and the DTAC protein were observed to exhibit their biological function in contrast to STAC.

SACT Protein

A membrane bound CD59 was previously observed to protect cells from complement-mediated disease, however the site of expression of the regulator, yielded only a "patch" of protection in the ocular tissue such as the RPE. Thus, a secreted regulator of CD59 (sCD59 or rmiCD59) is here engineered, which was capable of diffusing through the retina and offer protection to the entire affected region (Kumar-Singh et al., PCT application serial number PCT/US09/00947 filed Feb. 13, 2009 which is hereby incorporated by herein in its entirety).

Soluble sCD59 was previously considered an inefficient regulator of complement in vivo unless it was fused with a membrane targeting moiety (Mizuno et al. 2001 Arthritis Rheum 44: 2425-2434; Bora 2010 J Biol Chem 285: 33826-33833; Song et al. 2003 J Clin Invest 111: 1875-1885; and Zhang et al. 1999 J Clin Invest 103: 55-61). A membrane-independent sCD59 expressed in vivo in murine ocular tissue via an adenovirus or AAV vector significantly reduced MAC deposition and laser-induced choroidal neovascularization in a mouse model of neovascular AMD (Cashman et al. 2011 PLoS ONE 6(4): e19078, which is hereby incorporated by reference in its entirety). Adenovirus-delivered sCD59 was observed to inhibit human MAC deposition even on murine liver vasculature.

Without being limited by any particular theory or mechanism of action, it is here envisioned that a recombinant fusion protein containing at least two of CD59 protein, CD46 protein and CD55 protein is a potent regulator of a number of complement pathways and proteins. Examples herein provide methods for engineering a novel Soluble Active Complement Terminator (SACT) having small functional units of each of CD46 protein, CD55 protein, and CD59 protein that are effective for treating complement-related conditions by modulating the complement cascade, and provide the composition. The resulting SACT protein composition includes functional units of CD46 protein, CD55 protein, and CD59 protein that in certain embodiments are operably linked. For example, the functional units are connected by a linker, which is a sequence of amino acids that does not affect the function of the components or the structural stability of the protein. Furthermore, the protein in certain embodiments is mutated to remove or delete a sequence encoding a protein membrane anchor. In a related embodiment, an exemplary SACT protein includes a secretory signal at the N-terminus. The SACT protein is approximately 130 KDa and was obtained retaining only the units/domains of each component protein that are involved in complement regulation. Other soluble complement regulators such as factor H (150 kDa) and sCR1 (200 kDa) are larger, and these have been used to regulate complement (Ripoche et al. 1984 Biochem J 221: 89-96; and Yoon et al. 1985 J Immunol 134: 3332-3338).

The recombinant SACT protein engineered herein is differs from naturally occurring regulators because it includes multiple complement regulatory domains from different combinations of CD59, CD46, and CD55 proteins and is membrane independent. Hence SACT protein is capable of diffusing and blanketing a large group of affected cells or tissue for treatment after a single administration at one time. For example the SACT protein includes an amino acid sequence from at least two of a CD46 protein, a CD55 protein, and a CD59 protein. For example, the SACT protein includes at least one of: the CD46 protein and the CD59 protein, the CD46 protein and the CD55 protein, and the CD55 protein and the CD59 protein. Alternatively, the SACT protein includes each of CD59 protein, CD46 protein and CD55 protein, operably linked and expressed for example in a soluble form. In various embodiments, the CD46 protein, the CD55 protein, and the CD59 protein are derived from mammalian proteins (e.g., human, mouse, and rabbit). For example the SACT protein comprises a CD46 protein and a CD59 protein that are human proteins and a CD55 protein that is a murine protein, or comprises each of CD46, CD55, and CD59 that are human proteins. Thus in various embodiments the SACT protein comprises proteins that are from the same mammal type, or from different types of mammals.

Without being limited by any particular theory or mechanism of action, it is here envisioned that the SACT protein synergistically blocks complement activation at multiple steps in the complement pathway, including each of the complement pathways regulated by each of CD59 protein, CD46 protein, and CD55 protein. The SACT protein was observed in Examples herein to have inhibited MAC deposition in vivo when delivered by an adenovirus vector, and is therefore potentially effective as an anti-complement therapy for treating or even preventing complement-associated diseases or conditions.

In various embodiments, the SACT protein or composition includes a CD46 protein encoded by a full length nucleic acid of CD46 which was modified to remove the amino acid sequences for signal sequence and hydrophobic transmembrane spanning domains. Alternatively the nucleic acid sequence of CD46 protein is modified by point mutations, substitutions or deletions to obtain a nucleic acid sequence that encodes a modified amino acid sequence with the modification located in the hydrophobic transmembrane spanning domain, such that the resulting protein fails to attach to cell membranes.

The term "membrane independent CD46" as used herein refers to a CD46 amino acid sequence that lacks a hydrophobic transmembrane spanning domain or has a modified hydrophobic transmembrane spanning domain that lacks functional ability to bind to a cell membrane or a cell-membrane-associated structure such as a membrane-bound protein. The scope of the CD46 protein herein is envisioned to include conservative sequence modifications including deletions, substitutions, and additions as has been described herein.

As used herein, the term "conservative sequence modifications" refers to amino acid modifications that do not significantly affect or alter the characteristics of the CD46 protein containing the amino acid sequence, i.e., amino acid sequences of CD46 protein that present the side chains at the same relative positions in the amino acid sequence will function in a manner similar to human CD46 protein. Such conservative modifications include amino acid substitutions, additions and deletions. Modification of the amino acid sequence of CD46 protein is achieved using any known technique in the art e.g., site-directed mutagenesis or PCR based mutagenisis. Such techniques are described in Sambrook et al., Molecular Cloning: A Laboratory Manual, Cold Spring Harbor Press, Plainview, N.Y., 1989 and Ausubel et al., Current Protocols in Molecular Biology, John Wiley & Sons, New York, N.Y., 1989.

Conservative amino acid substitutions are ones in which the amino acid residue is replaced with an amino acid residue having a functionally similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine).

In certain embodiments, the CD46 amino acid sequence is an amino acid sequence that is substantially identical to that of the wild type sequence. The term "substantially identical" is used herein to refer to a first amino acid sequence that contains a sufficient or minimum number of amino acid residues that are identical to aligned amino acid residues in a second amino acid sequence such that the first and second amino acid sequences can have a common structural domain and/or common functional activity. For example, amino acid sequences that contain a common structural domain having at least about 60% identity, or at least 75%, 85%, 95%, 96%, 98%, or 99% identity are substantially identical.

Calculations of sequence identity between sequences are performed as follows. To determine the percent identity of two amino acid sequences, the sequences are aligned for optimal comparison purposes (e.g., gaps can be introduced in one or both of a first and a second amino acid sequence for optimal alignment). The amino acid residues at corresponding amino acid positions or nucleotide positions are then compared. When a position in the first sequence is occupied by the same amino acid residue or nucleotide as the corresponding position in the second sequence, then the proteins are identical at that position. The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences are accomplished using a mathematical algorithm. Percent identity between two amino acid sequences is determined using an alignment software program using the default parameters. Suitable programs include, for example, CLUSTAL W by Thompson et al., Nuc. Acids Research 22:4673, 1994, BL2SEQ by Tatusova and Madden, FEMS Microbiol. Lett. 174:247, 1999, SAGA by Notredame and Higgins, Nuc. Acids Research 24:1515, 1996, and DIALIGN by Morgenstern et al., Bioinformatics 14:290, 1998.

In various embodiments, the SACT protein or composition includes a CD55 protein and/or a CD59 protein. In various embodiments, the CD55 protein includes a full length nucleic acid of CD55. Alternatively, the CD55 protein is a portion or homologue of full length nucleic acid sequence or amino acid sequence as described herein. In certain embodiments, the CD55 protein includes conservative sequence modifications of the CD59 protein.

Mature human CD59 protein is composed of 77 amino acids and has a molecular weight of about 18 kD to about 21 kD. Precursor human CD59 protein includes an amino-terminal signal peptide of 25 amino acids and a carboxyl-terminal peptide of 26 amino acids which allows for attachment of a membrane anchor. Amino acid sequences of precursor human CD59 protein, a mature human CD59 protein, and CD59 protein of other mammals, e.g., baboon, African green monkey, owl monkey, marmoset, HVS-15, pig, rabbit, rat, and mouse, are shown in Sims et al. U.S. Pat. No. 7,166,568 issued Jan. 23, 2007 which is incorporated herein by reference in its entirety.

The protein structure of CD59 is characterized as a single cysteine-rich domain, having a hydrophobic core with three loops and a small fourth helical loop (Yu et al., Journal of Experimental Medicine, 185(4):745-753, 1997). Disulfide-bonded cysteine pairs connect each of these loops (Yu et al., 1997).

The structure of the gene encoding CD59 has been characterized (Fodor et al. U.S. Pat. No. 5,624,837, issued Apr. 29, 1997). The gene is located on the short arm of chromosome 11 in humans, specifically chromosome 11p13 and 11p14 (Online Mendelian Inheritance in Man accession number and 107271), and consists of four exons spanning 20 kb (Petranka et al. Proc. Nat. Acad. Sci. 89:7876-7879, 1992). An untranslated first exon is preceded by a G and C-rich promoter region that lacks a consensus TATA or CAAT motif. The second exon encodes the hydrophobic leader sequence of the protein, and the third exon encodes the N-terminal portion of the mature protein. The fourth exon encodes the remainder of the mature protein, including the hydrophobic sequence for glycophosphoinosital anchor attachment to a cell membrane.

CD59 is a glycosylphosphatidylinositol-anchored glycoprotein that is expressed on human peripheral blood leukocytes, erythrocytes, and many cell lines. The protein is expressed on both hematopoietic and non-hematopoietic cells, for example on endothelial cells, peripheral nerve fibers, neurons, microglia, oligodendrocytes, astrocytes, ependymal cells, epithelial cells, acinar cells of the salivary glands, bronchial epithelium, renal tubules and squamous epithelium. See Nose, M. et al. 1990 Immunology 70(2): 145-149; Vedeler, C. et al. 1994 Immunology 82(4): 542-547; and Hidestima, T. et al. 1990 Immunology 69(3): 396:401. A cDNA encoding CD59 was reported by Sawada, R. et al. 1989 Nucleic Acids Res 17(16) 6728. CDNA encoding CD59 has also been cloned from human T-cell leukemia (YT) and human erythroleukemia (K562) cell lines, and CD59 has been transiently expressed in COS cells (Walsh, L. A. et al. 1990 Eur J. Immol 21(3): 847-850). Human CD59 which is encoded by a nucleic acid sequence includes 26 amino acids located at the C terminus, which contains a signal sequence for attachment of a GPI anchor at amino acid asparagine at position 77. The amino acid sequence of full length cDNA of CD59 is shown in Fodor et al., U.S. Pat. No. 5,624,837 issued Apr. 29, 1997.

Analysis of the physical association of CD59 with components of MAC shows that separate binding sites for CD59 are contained within the a-chains of each of human C8 and human C9 (See Kimberley et al. 2007 Mol Immunol 44: 73-81). The binding site for interactions of human CD59 with human. C9 has been identified as amino acid residues 42 to 58 in the sequence of mature human CD59, that bind to the region of human C9 corresponding to human amino acid residues 334 to 418 of that protein, more particularly human C9 amino acid residues 359 to 384, immediately C-terminal to the predicted membrane-inserting domain of C9 (Sims et al. PCT/US96/17940 filed Nov. 8, 1996, which is incorporated herein by reference in its entirety).

The active surface exposed amino acid residue side chains that are available to bind C8/C9, identified from solution structure of mature human CD59 from published NMR data and the knowledge of the active portion of the CD59 molecule, are histidine at position 44, asparagine at position 48, aspartic acid at position 49, threonine at positions 51 and 52, arginine at position 55, and glutamic acid at position 58. NMR structures for CD59 are described in deposits by Kieffer et al., Human Complement Regulatory Protein CD59 (Extracellular Region, Residues 1 70; NMR, 10 Structures), MMDB Id: 891, PDB Id: 1ERH; Kieffer et al., Human Complement Regulatory Protein CD59 (Extracellular Region, Residues 1 70; NMR, Restrained), MMDB Id: 890, PDB Id: 1ERG; Fletcher et al., CD59 Complexed With Glcnac-Beta-1,4-(Fuc-Alpha-1,6)-Glcnac-Beta-1 (NMR, 10 Structures), MMDB Id: 498, PDB Id: 1CDS; Fletcher et al., CD59 Complexed With Glcnac-Beta-1,4-Glcnac-Beta-1 (NMR, 10 Structures), MMDB Id: 497, PDB Id: 1CDR. The 1CDS and 1CDR deposits by Fletcher et al. Amino acid sequences of CD59 that present these side chains at the same relative positions function in a manner similar to human CD59 (Sims et al.), and such variants are within the scope of the methods, kits and pharmaceutical compositions herein.

A CD59 protein in certain embodiments used in construction of the SACT protein herein lacks the primary amino acid sequence for a functional GPI anchor. An embodiment which is a functional equivalent protein includes a modified GPI anchor domain amino acid sequence that is functionally defective and lacks the ability to target a membrane. Additional methods of obtaining a SACT protein having a membrane-independent CD59 protein include non-recombinant methods such as providing an inhibitor of membrane association, for example, synthesizing CD59 in vivo or in vitro such that the GPI anchor is lacking. Methods of obtaining the membrane-independent CD59 are shown in examples herein. Additional recombinant techniques for altering the nucleic acid sequence and amino acid sequence of a molecule are well known in the art of genetics and molecular biology.

In various embodiments, the composition includes an amino acid sequence of a CD59 protein having a full length nucleic acid of CD59 protein that was modified to remove the signal sequence for attachment of the GPI anchor at the nucleotides encoding amino acid asparagine at position 77. Alternatively the nucleic acid sequence of CD59 is modified by one or more point mutations, substitutions or deletions to obtain a nucleic acid sequence that encodes an amino acid sequence that has a modified amino acid sequence at the GPI anchor location, such that the protein is unable to attach to a membrane of a cell. The term "membrane independent CD59" as used herein refers to a CD59 amino acid sequence that lacks a GPI anchor or has a modified GPI anchor that lacks function, viz., that lacks ability to bind to a cell membrane or a cell-membrane-associated structure such as a membrane-bound protein.

GPI anchoring involves a multi-step pathway in the endoplasmic reticulum including the interaction of numerous gene products. Many proteins including CD59 require GPI to be expressed at the cell surface and to function effectively. The mechanism by which structure in a protein signal encodes for attachment of GPI anchors is reviewed by Orlean, P. et al. 2007 JLR 48:993-1011. GPI attachment generally involves an amino acid sequence that contains: a hydrophobic N-terminal secretion signal that targets the protein to the ER, and a C-terminal GPI signal anchor sequence. The amino acid to which the GPI becomes linked is referred to as the omega (ω) residue, with amino acids N-terminal to the omega residue referred to as omega-minus (ω−) and with amino acids C-terminal to the omega residue referred to as omega-plus (ω+). The GPI anchor sequence includes a stretch of about ten polar amino acids (i.e., ω-10 to ω-1), for example arginine, lysine, aspartate, glutamate, asparagine, or glutamate, that form a flexible linker region. The ω residue has been observed to be one of: glycine, alanine, serine, asparagine, aspartic acid, or cysteine. Mutation including substitution and deletion of nucleic acids encoding amino acids at omega positions are used to reduce or eliminate the attachment of the GPI anchor or reduce or eliminate the effective functionality of the GPI anchor. For example, such a variation includes substituting the nucleic acids encoding hydrophobic leucine (e.g., nucleic acids CTG) and alanine (e.g., nucleic acids GCA) with nucleic acids encoding glycine (e.g., nucleic acids CAG) and glutamate (e.g., nucleic acids GAA), which are less hydrophobic (i.e., more hydrophilic) amino acids. Alternatively, a variation includes substituting the ω residue with another amino acid, for example substituting a glycine for a tyrosine.

In other portions of the protein not involved in GPI anchoring, the STAC protein herein includes amino acid sequences from a CD59 protein having conservative sequence modifications. As used herein, the term "conservative sequence modifications" refers to amino acid modifications that do not significantly affect or alter the characteristics of the CD59 protein or membrane-independent CD59 containing the amino acid sequence, i.e., amino acid sequences of CD59 that present these side chains at the same relative positions will function in a manner similar to human CD59. Such conservative modifications include amino acid substitutions, additions and deletions. Modification of the amino acid sequence of CD59 is achieved using any known technique in the art e.g., site-directed mutagenesis or PCR based mutagenesis. Such techniques are described in Sambrook et al., Molecular Cloning: A Laboratory Manual, Cold Spring Harbor Press, Plainview, N.Y., 1989 and Ausubel et al., Current Protocols in Molecular Biology, John Wiley & Sons, New York, N.Y., 1989. Conservative amino acid substitutions are ones in which the amino acid residue is replaced with an amino acid residue having a similar side chain such as replacing a small amino acid with a different small amino acid, a hydrophilic amino acid with a different hydrophilic amino acid, etc. . . .

Examples herein include methods, compositions and kits having a chimeric soluble terminator of activated complement (SACT) protein with amino acid sequences from each of a CD46 protein, a CD55 protein, and a CD59 protein, and a nucleic acid engineered for encoding and expressing the recombinant SACT protein, such that the SACT negatively modulates classical and alternative complement pathways and treats complement-related conditions. Alternatively, the SACT protein includes amino acid sequences from at least two of a CD46 protein, a CD55 protein, and a CD59 protein. The phrase "complement-related" as used herein and in the claims includes without limitation "complement-associated", and refers to any cell or tissue that is affected by a complement pathway. Examples of complement-related disorders or conditions include macular degeneration, lupus nephritis, Sjögren's syndrome, organ graft rejection, asthma, and chronic obstructive pulmonary disease.

Vectors

Methods herein for treating or preventing a complement-related disorder include contacting cells with a pharmaceutical composition including a C3 protein, a CD46 protein, a CD55 protein, a SACT protein, or a DTAC protein in which the protein is recombinantly produced. The term "recombinant" refers to proteins produced by manipulation of genetically modified organisms, for example micro-organisms.

An exemplary source of the protein includes a polynucleotide sequence that encodes the protein, for example, a nucleotide sequence encoding the protein, or functional equivalent, is inserted into an appropriate expression vector, i.e., a vector that contains the necessary nucleic acid encoding elements that regulate transcription and translation of the inserted coding sequence, operably linked to the nucleotide sequence encoding the amino acid sequence of the recombinant protein.

Methods that are well known to those skilled in the art are used to construct expression vectors containing a sequence encoding a protein operably linked to appropriate transcriptional and translational control elements. These methods include in vitro recombinant DNA techniques, synthetic techniques and in vivo recombination or genetic recombination. Such techniques are described in Sambrook et al., Molecular Cloning: A Laboratory Manual, Cold Spring Harbor Press, Plainview, N.Y., 1989.

A variety of commercially available expression vector/host systems are useful to carry and express a protein encoding sequence. These include but are not limited to microorganisms such as bacteria transformed with recombinant bacteriophage, plasmid or cosmid DNA expression vectors; yeast transformed with yeast expression vectors; insect cell systems contacted with virus expression vectors (e.g., baculovirus); plant cell systems transfected with virus expression vectors (e.g., cauliflower mosaic virus, CaMV; tobacco mosaic virus, TMV) or transformed with bacterial expression vectors (e.g., Ti, pBR322, or pET25b plasmid); or animal cell systems. See Ausubel et al., Current Protocols in Molecular Biology, John Wiley & Sons, New York, N.Y., 1989.

Virus vectors include, but are not limited to, adenovirus vectors, lentivirus vectors, adeno-associated virus (AAV) vectors, and helper-dependent adenovirus vectors. For example, virus vectors deliver a nucleic acid sequence that encodes a SACT protein or a DTAC protein that as shown herein treat complement-related conditions. Adenovirus packaging vectors are commercially available from American Type Tissue Culture Collection (Manassas, Va.). Methods of constructing adenovirus vectors and using adenovirus vectors are shown in Klein et al., Ophthalmology, 114:253-262, 2007 and van Leeuwen et al., Eur. J. Epidemiol., 18:845-854, 2003.

Adenovirus vectors have been used in eukaryotic gene expression (Levrero et al., Gene, 101:195-202, 1991) and vaccine development (Graham et al., Methods in Molecular Biology: Gene Transfer and Expression Protocols 7, (Murray, Ed.), Humana Press, Clifton, N.J., 109-128, 1991). Further, recombinant adenovirus vectors are used for gene therapy (Wu et al., U.S. Pat. No. 7,235,391).

Recombinant adenovirus vectors are generated, for example, from homologous recombination between a shuttle vector and a provirus vector (Wu et al., U.S. Pat. No. 7,235,391). The adenovirus vectors herein are replication defective, for example, are conditionally defective, lacking an adenovirus region, and a polynucleotide encoding a peptide or protein is introduced at the position from which the coding sequences have been removed. The polynucleotide encoding the gene of interest alternatively is inserted in another region.

Helper cell lines may be derived from human cells, such as 293 human embryonic kidney cells, muscle cells, hematopoietic cells or other human embryonic mesenchymal or epithelial cells. Alternatively, the helper cells may be derived from the cells of other mammalian species that are permissive for human adenovirus, e.g., Vero cells or other monkey embryonic mesenchymal or epithelial cells. Generation and propagation of these replication defective adenovirus vectors using a helper cell line is described in Graham et al, J. Gen. Virol., 36:59-72, 1977.

Lentiviral vector packaging vectors are commercially available from Invitrogen Corporation (Carlsbad, Calif.). An HIV-based packaging system for the production of lentiviral vectors is prepared using constructs in Naldini et al., Science 272: 263-267, 1996; Zufferey et al., Nature Biotechnol., 15: 871-875, 1997; and Dull et al., J. Virol. 72: 8463-8471, 1998.

A number of vector constructs are available to be packaged using a system based on third-generation lentiviral SIN vector backbone (Dull et al., J. Virol. 72: 8463-8471, 1998). For example the vector construct pRRLsinCMVGFPpre contains a 5' LTR in which the HIV promoter sequence has been replaced with that of Rous sarcoma virus (RSV), a self-inactivating 3' LTR containing a deletion in the U3 promoter region, the HIV packaging signal, RRE sequences linked to a marker gene cassette consisting of the Aequora jellyfish GFP driven by the CMV promoter, and the woodchuck hepatitis virus PRE element, which appears to enhance nuclear export. The GFP marker gene allows quantitation of transfection or transduction efficiency by direct observation of UV fluorescence microscopy or flow cytometry (Kafri et al., Nature Genet., 17: 314-317, 1997 and Sakoda et al., J. Mol. Cell. Cardiol., 31: 2037-2047, 1999).

Manipulation of retroviral nucleic acids to construct a retroviral vector containing the gene that encodes for a peptide or protein and packaging cells is accomplished using techniques known in the art. See Ausubel, et al., 1992, Volume 1, Section III (units 9.10.1-9.14.3); Sambrook, et al., 1989. Molecular Cloning: A Laboratory Manual. Second Edition. Cold Spring Harbor Laboratory Press, Cold Spring Harbor, N.Y.; Miller, et al., Biotechniques. 7:981-990, 1989; Eglitis, et al., Biotechniques. 6:608-614, 1988; U.S. Pat. Nos. 4,650,764, 4,861,719, 4,980,289, 5,122,767, and 5,124,263; and PCT patent publications numbers WO 85/05629, WO 89/07150, WO 90/02797, WO 90/02806, WO 90/13641, WO 92/05266, WO 92/07943, WO 92/14829, and WO 93/14188.

A retroviral vector is constructed and packaged into non-infectious transducing viral particles (virions) using an amphotropic packaging system. Examples of such packaging systems are found in, for example, Miller, et al., Mol. Cell Biol. 6:2895-2902, 1986; Markowitz, et al., J. Virol. 62:1120-1124, 1988; Cosset, et al., J. Virol. 64:1070-1078, 1990; U.S. Pat. Nos. 4,650,764, 4,861,719, 4,980,289, 5,122,767, and 5,124,263, and PCT patent publications numbers WO 85/05629, WO 89/07150, WO 90/02797, WO 90/02806, WO 90/13641, WO 92/05266, WO 92/07943, WO 92/14829, and WO 93/14188.

Generation of "producer cells" is accomplished by introducing retroviral vectors into the packaging cells, a process of contacting referred to herein as "transducing", "transfecting", or "infecting". Examples of such retroviral vectors are found in, for example, Korman, et al., Proc. Natl. Acad. Sci. USA. 84:2150-2154, 1987; Morgenstern, et al., Nucleic Acids Res. 18:3587-3596, 1990; U.S. Pat. Nos. 4,405,712, 4,980,289, and 5,112,767; and PCT patent publications numbers WO 85/05629, WO 90/02797, and WO 92/07943.

Herpesvirus packaging vectors are commercially available from Invitrogen Corporation, (Carlsbad, Calif.). Exemplary herpesviruses are an α-herpesvirus, such as Varicella-Zoster virus or pseudorabies virus; a herpes simplex virus such as HSV-1 or HSV-2; and a herpesvirus such as Epstein-Barr virus. A method for preparing empty herpesvirus particles that can be packaged with a desired nucleotide segment, for example a nucleotide or polynucleotide sequence, in the absence of a helper virus that is capable to most herpesviruses is shown in Fraefel et al. (U.S. Pat. No. 5,998,208, issued Dec. 7, 1999).

The herpesvirus DNA vector can be constructed using techniques familiar to the skilled artisan. For example, DNA segments encoding the entire genome of a herpesvirus is divided among a number of vectors capable of carrying large DNA segments, e.g., cosmids (Evans, et al., Gene 79, 9-20, 1989), yeast artificial chromosomes (YACS) (Sambrook, J. et al., MOLECULAR CLONING: A LABORATORY MANUAL, 2nd Edition, Cold Spring Harbor Press, Cold Spring Harbor, N.Y., 1989) or *E. coli* F element plasmids (O'Conner, et al., Science 244:1307-1313, 1989).

For example, sets of cosmids have been isolated which contain overlapping clones that represent the entire genomes of a variety of herpesviruses including Epstein-Barr virus, Varicella-Zoster virus, pseudorabies virus and HSV-1. See M. van Zijl et al., J. Virol. 62, 2191, 1988; Cohen, et al., Proc. Nat'l Acad. Sci. U.S.A. 90, 7376, 1993; Tomkinson, et al., J. Virol. 67, 7298, 1993; and Cunningham et al., Virology 197, 116, 1993.

AAV is a dependent parvovirus in that it depends on co-infection with another virus (either adenovirus or a member of the herpes virus family) to undergo a productive infection in cultured cells (Muzyczka, Curr Top Microbiol Immunol, 158:97 129, 1992). For example, recombinant AAV (rAAV) virus is made by co-transfecting a plasmid containing the gene of interest, for example, the a gene of interest, flanked by the two AAV terminal repeats (McLaughlin et al., J. Virol., 62(6):1963 1973, 1988; Samulski et al., J. Virol, 63:3822 3828, 1989) and an expression plasmid containing the wild-type AAV coding sequences without the terminal repeats. Cells are also contacted or transfected with adenovirus or plasmids carrying the adenovirus genes required for AAV helper function. Recombinant AAV virus stocks made in such fashion include with adenovirus which must be physically separated from the recombinant AAV particles (for example, by cesium chloride density centrifugation).

Adeno-associated virus (AAV) packaging vectors are commercially available from GeneDetect (Auckland, New Zealand). AAV has been shown to have a high frequency of integration and infects non-dividing cells, thus making it useful for delivery of genes into mammalian cells in tissue culture (Muzyczka, Curr Top Microbiol Immunol, 158:97 129, 1992). AAV has a broad host range for infectivity (Tratschin et al., Mol. Cell. Biol., 4:2072 2081, 1984; Laughlin et al., J. Virol., 60(2):515 524, 1986; Lebkowski et al., Mol. Cell. Biol., 8(10):3988 3996, 1988; McLaughlin et al., J. Virol., 62(6):1963 1973, 1988).

Methods of constructing AAV vectors and using AAV vectors are described, for example in U.S. Pat. Nos. 5,139, 941 and 4,797,368. Use of AAV in gene delivery is further described in LaFace et al., Virology, 162(2):483 486, 1988; Zhou et al., Exp. Hematol, 21:928 933, 1993; Flotte et al., Am. J. Respir. Cell Mol. Biol., 7(3):349 356, 1992; and Walsh et al., J. Clin. Invest, 94:1440 1448, 1994.

Recombinant AAV vectors have been used successfully for in vitro and in vivo transduction of marker genes (Kaplitt et al., Nat Genet., 8(2):148 54, 1994; Lebkowski et al., Mol. Cell. Biol., 8(10):3988 3996, 1988; Samulski et al., EMBO J., 10:3941 3950, 1991; Shelling and Smith, Gene Therapy, 1: 165 169, 1994; Yoder et al., Blood, 82 (Supp.): 1:347A, 1994; Zhou et al., Exp. Hematol, 21:928 933, 1993; Tratschin et al., Mol. Cell. Biol., 5:3258 3260, 1985; McLaughlin et al., J. Virol., 62(6):1963 1973, 1988) and transduction of genes involved in human diseases (Flotte et al., Am. J. Respir. Cell Mol. Biol., 7(3):349 356, 1992; Ohi et al., Gene, 89(2):279 282, 1990; Walsh et al., J. Clin. Invest, 94:1440 1448, 1994; and Wei et al., Gene Therapy, 1:261 268, 1994).

In certain embodiments, the vectors herein are non-viral vectors for example synthetic gene delivery vehicles or vectors that are not related to a virus particle and that specifically deliver the gene material to the target cells or tissue. Examples of non-viral vectors include liposomes, peptides, nanoparticles, emulsions, or encapsulated two or more phase systems or other suitable preparation. Thus, in certain embodiments a method, kit, or composition involves a non-viral vector with nucleic acid that is loaded and contacted to a tissue or cell. For example a liposome containing naked DNA encoding a protein is encapsulated in the liposome and the liposome is contacted to the tissue or cell such that the nucleic acid is effectively delivered to the tissue or cell for treatment of a complement-related disease.

Pharmaceutical Compositions

An aspect of the present invention provides pharmaceutical compositions that include at least one of CD46 protein, a CD55 protein, a DTAC protein, and a SACT protein or a nucleic acid encoding and expressing the protein, for treating a complement-related disorder by negatively modulating complement proteins or pathways. In certain embodiments, the pharmaceutical composition is compounded for systemic delivery to a subject, for example the composition is formulated as an injection. The composition in another embodiment is formulated as an ophthalmologic formulation for administration to the eye and may be compounded for delivery to the fundus, or for release locally at the retina or otherwise formulated to provide effective treatment of the vessels and/or tissue involved in complement disorders negatively affecting the ocular tissues. In related embodiments, the pharmaceutical composition is formulated sufficiently pure for administration to a human subject, e.g., to the vascular system or endothelial system of a human subject. In certain embodiments, these compositions optionally further include one or more additional therapeutic agents. In certain embodiments, the additional therapeutic agent or agents are selected from the group consisting of growth factors, anti-inflammatory agents, vasopressor agents including but not limited to nitric oxide and calcium channel blockers, collagenase inhibitors, topical steroids, matrix metalloproteinase inhibitors, ascorbates, angiotensin II, angiotensin III, calreticulin, tetracyclines, fibronectin, collagen, thrombospondin, transforming growth factors (TGF), keratinocyte growth factor (KGF), fibroblast growth factor (FGF), insulin-like growth factors (IGFs), IGF binding proteins (IGFBPs), epidermal growth factor (EGF), platelet derived growth factor (PDGF), neu differentiation factor (NDF), hepatocyte growth factor (HGF), vascular endothelial growth factor (VEGF), heparin-binding EGF (HBEGF), thrombospondins, von Willebrand Factor-C, heparin and heparin sulfates, and hyaluronic acid.

In certain embodiments, a plurality of therapeutic agents are included in the pharmaceutical composition to treat the same, a concurrent or a related symptom, condition or disease. In some embodiments, the therapeutic agent is a drug that may include without limitation anti-coagulant, anti-tumor, anti-viral, anti-bacterial, anti-mycobacterial, anti-fungal, anti-proliferative or anti-apoptotic agents. Drugs that are included in the compositions of the invention are well known in the art. See for example, Goodman & Gilman's The Pharmacological Basis of Therapeutics, 9th Ed., Hardman, et al., eds., McGraw-Hill, 1996, the contents of which are herein incorporated by reference herein in their entireties.

As used herein, the term "pharmaceutically acceptable carrier" includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences Ed. by Gennaro, Mack Publishing, Easton, Pa., 1995 provides various carriers used in formulating pharmaceutical compositions and known techniques for the preparation thereof. Some examples of materials which can serve as pharmaceutically acceptable carriers include, but are not limited to, sugars such as glucose and sucrose; excipients such as cocoa butter and suppository waxes; oils such as peanut oil, cottonseed oil, safflower oil, sesame oil, olive oil, corn oil, and soybean oil; glycols such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol; and phosphate buffer solutions, as well as other non-toxic compatible lubricants such as sodium lauryl sulfate and magnesium stearate, as well as coloring agents, releasing agents, coating agents, preservatives and antioxidants can also be present in the composition, the choice of agents and non-irritating concentrations to be determined according to the judgment of the formulator.

Therapeutically Effective Dose

Methods provided herein involve contacting cells or tissues with a pharmaceutical composition, for example, administering a therapeutically effective amount of a pharmaceutical composition having as an active agent at least one of CD46 protein, CD55 protein, a DTAC protein, and a SACT protein, a nucleic acid encoding a protein or a source of expression of the protein, to a subject in need thereof, in such amounts and for such time as is necessary to achieve the desired result including reduction or preventing of indicia of the complement-related condition.

The compositions, according to the method of the present invention, may be administered using any amount and any route of administration effective for treating the complement-related disorder. Thus, the expression "amount effective for treating a complement-related disease or condition", as used herein, refers to a sufficient amount of composition to beneficially prevent or ameliorate the symptoms of the disease or condition.

The exact dosage is chosen by the individual physician in view of the patient to be treated. Dosage and administration are adjusted to provide sufficient levels of the active agent(s) or to maintain the desired effect. Additional factors which may be taken into account include the severity of the disease state, e.g., intermediate or advanced stage of macular degeneration; age, weight and gender of the patient; diet, time and frequency of administration; route of administration; drug combinations; reaction sensitivities; and tolerance/response to therapy. Long acting pharmaceutical compositions might be administered hourly, twice hourly, every three to four hours, daily, twice daily, every three to four days, every week, or once every two weeks depending on half-life and clearance rate of the particular composition.

The active agents of the invention are preferably formulated in dosage unit form for ease of administration and uniformity of dosage. The expression "dosage unit form" as used herein refers to a physically discrete unit of active agent appropriate for the patient to be treated. It will be understood, however, that the total daily usage of the compositions of the present invention will be decided by the attending physician within the scope of sound medical judgment. For any active agent, the therapeutically effective dose can be estimated initially either in cell culture assays or in animal models, as provided herein, usually mice, but also potentially from rats, rabbits, dogs, or pigs. The animal cell model and in vivo model provided herein are also used to achieve a desirable concentration and total dosing range and route of administration. Such information can then be used to determine useful doses and routes for administration in humans.

A therapeutically effective dose refers to that amount of active agent that ameliorates the symptoms or condition or prevents progression of the disease or condition. Therapeutic efficacy and toxicity of active agents can be determined by standard pharmaceutical procedures in cell cultures or experimental animals, e.g., ED50 (the dose is therapeutically effective in 50% of the population) and LD50 (the dose is lethal to 50% of the population). The dose ratio of toxic to therapeutic effects is the therapeutic index, and it can be expressed as the ratio, LD50/ED50. Pharmaceutical compositions which exhibit large therapeutic indices are preferred. The data obtained from cell culture assays and animal studies are used in formulating a range of dosage for human use.

The daily dosage of the products may be varied over a wide range, such as from 0.001 to 1000 mg (1 gram) per adult human per day. For ocular administration, the compositions are provided for example in the form of a solution containing 0.001, 0.01, 0.05, 0.1, 0.5, 1.0, 2.5, 5.0, 10.0, 15.0, 25.0, 50.0, 100.0, 250.0, or 500.0 micrograms of the active ingredient for the symptomatic adjustment of the dosage to the patient to be treated.

A unit dose typically contains from about 0.001 micrograms to about 500 micrograms of the active ingredient, preferably from about 0.1 micrograms to about 100 micrograms of active ingredient, more preferably from about 1.0 micrograms to about 10 micrograms of active ingredient. An effective amount of the drug is ordinarily supplied at a dosage level of from about 0.0001 mg/kg to about 25 mg/kg of body weight per day. For example, the range is from about 0.001 to 10 mg/kg of body weight per day, or from about 0.001 mg/kg to 1 mg/kg of body weight per day. The compositions may be administered on a regimen of, for example, one to four or more times per day. A unit dose may be divided for example, administered in two or more divided doses.

Administration of a source of expression of a protein is administration of a dose of a viral vector or a nucleic acid vector, for example the dose contains at least about 50, 100, 500, 1000, or at least about 5000 particles per cell to be treated. Alternatively, the dose of a viral vector or a nucleic acid vector is at least about $10^4$ to about $10^5$; about $10^5$ to about $10^6$; $10^6$ to about $10^7$; $10^7$ to about $10^8$; about $10^8$ to about $10^9$; about $10^9$ to about $10^{10}$; or at least about $10^{10}$ to about $10^{11}$. The dose effective for treating a cell number can be calculated from the area in need of treatment by methods known to one of skill in the art.

Administration of Pharmaceutical Compositions

As formulated with an appropriate pharmaceutically acceptable carrier in a desired dosage, the pharmaceutical composition provided herein is administered to humans and other mammals for example topically (as by powders, ointments, or drops), orally, rectally, mucosally, sublingually, parenterally, intracisternally, intravaginally, intraperitoneally, bucally, sublingually, ocularly, or intranasally, depending on preventive or therapeutic objectives and the severity and nature of a complement-related disorder or condition.

Injections include intravenous injection or intra-ocular injection into the aqueous or the vitreous humor, or injection into the external layers of the eye, such by subconjunctival injection or subtenon injection.

Liquid dosage forms for example for intravenous, ocular, mucosal, or other administration include, but are not limited to, pharmaceutically acceptable emulsions, microemulsions, solutions, suspensions, syrups and elixirs. In addition to the active agent(s), the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the ocular, oral, or other systemically-delivered compositions can also include adjuvants such as wetting agents, and emulsifying and suspending agents.

Dosage forms for topical or transdermal administration of an inventive pharmaceutical composition include ointments, pastes, creams, lotions, gels, powders, solutions, sprays, inhalants, or patches. The active agent is admixed under sterile conditions with a pharmaceutically acceptable carrier and any needed preservatives or buffers as may be required. For example, ocular or cutaneous routes of administration are achieved with aqueous drops, a mist, an emulsion, or a cream. Administration may be therapeutic or it may be prophylactic. The invention includes ophthalmological devices, surgical devices, audiological devices or products which contain disclosed compositions (e.g., gauze bandages or strips), and methods of making or using such devices or products. These devices may be coated with, impregnated with, bonded to or otherwise treated with a composition as described herein.

Transdermal patches have the added advantage of providing controlled delivery of the active ingredients to the eye and body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use. In order to prolong the effect of an active agent, it is often desirable to slow the absorption of the agent from subcutaneous or intramuscular injection. Delayed absorption of a parenterally administered active agent may be accomplished by dissolving or suspending the agent in an oil vehicle. Injectable depot forms are made by forming microencapsule matrices of the agent in biodegradable polymers such as polylactide-polyglycolide. Depending upon the ratio of active agent to polymer and the nature of the particular polymer employed, the rate of active agent release can be controlled. Examples of other biodegradable polymers include poly(orthoesters) and poly(anhydrides). Depot injectable formulations are also prepared by entrapping the agent in liposomes or microemulsions which are compatible with body tissues.

Compositions for rectal or vaginal administration are preferably suppositories which can be prepared by mixing the active agent(s) of this invention with suitable non-irritating excipients or carriers such as cocoa butter, polyethylene glycol or a suppository wax which are solid at ambient temperature but liquid at body temperature and therefore melt in the rectum or vaginal cavity and release the active agent(s).

Solid dosage forms for oral administration include capsules, tablets, pills, powders, and granules. In such solid dosage forms, the active agent is mixed with at least one inert, pharmaceutically acceptable excipient or carrier such as sodium citrate or dicalcium phosphate and/or a) fillers or extenders such as starches, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof.

Solid compositions of a similar type may also be employed as fillers in soft and hard-filled gelatin capsules using such excipients as milk sugar as well as high molecular weight polyethylene glycols and the like. The solid dosage forms of tablets, dragees, capsules, pills, and granules can be prepared with coatings and shells such as enteric coatings, release controlling coatings and other coatings well known in the pharmaceutical formulating art. In such solid dosage forms the active agent(s) may be admixed with at least one inert diluent such as sucrose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active agent(s) only, or preferentially, in a certain part of the intestinal tract, optionally, in a delayed manner. Examples of embedding compositions which can be used include polymeric substances and waxes.

The following examples and claims are illustrative only and not intended to be further limiting. Those skilled in the art will recognize or be able to ascertain using no more than routine experimentation, numerous equivalents to the specific procedures described herein. Such equivalents are within the scope of the present invention and claims. The contents of all references including issued patents and published patent applications cited in this application are hereby incorporated by reference.

A portion of the embodiments herein was published in J Gene Med. 2015 June; 17(6-7):101-15 as "Adeno-associated virus mediated delivery of an engineered protein that combines the complement inhibitory properties of CD46, CD55 and CD59 with co-authors Rajendra Kumar-Singh, Derek Leaderer and Siobhan M. Cashman which is hereby incorporated in its entirety herein in its entirety.

The invention now having been fully described, it is further exemplified by the following examples and claims.

EXAMPLES

Example 1

Cell Lines

Hepa1c1c7 and HEK293 cell lines were obtained from ATCC and maintained in αMEM and DMEM, respectively, supplemented with 10% FBS. The human embryonic retinoblast, 911, cell line was maintained in DMEM supplemented with 10% FBS (Fallaux, F. J., 1996 Hum Gene Ther 7: 215-222). Cell culture reagents were purchased from Invitrogen Life Technologies and cells were maintained in a humidified incubator at 37° C. with 5% CO2.

Example 2

Structure and Synthesis of SACT and DTAC

A cDNA was synthesized by GenScript (Piscataway, N.J.) to encode the Soluble Active Complement Terminator (SACT) which contains the sequence encoding the human CD59 (ATCC cat. 10658204) secretory peptide followed by the coding sequence for amino acids 34-296 of human CD46 (ATCC cat. 7491463) encoding the four SCR domains of CD46 (Lublin, D. M., et al. 1988 J Exp Med 168: 181-194). The human CD46 sequence is attached via a sequence encoding a five glycine linker to a sequence encoding amino acids 33-356 of human CD55 (ATCC cat. 5830488) which comprise the SCR domains and STP region of CD55 (Coyne, K. E., et al. 1992 J Immunol 149: 2906-2913). An additional sequence encoding a five glycine linker attaches the STP region of CD55 to a sequence encoding the 76 amino acid functional domain of human CD59. A cDNA encoding the Dual Terminator of Active Complement (DTAC) was also synthesized by GenScript to contain the sequence encoding the human CD59 secretory peptide followed by the coding sequence for amino acids 33-356 of human CD55 (as described above). The sequence encoding the STP region of CD55 sequence was attached via a sequence encoding a five glycine linker to a sequence encoding the 76 amino acid functional domain of human CD59. The cDNAs encoding SACT and DTAC were cloned into the XhoI and EcoRV sites of pAAVCAG, a modified version of pAAV-MCS (Stratagene) containing a chicken β-actin promoter/CMV enhancer (CAG) and a rabbit globin polyadenylation signal (generously provided by C. Cepko and Matsuda), to generate pAAV2CAGSACT and pAAV2CAGDTAC, respectively.

The nucleotide sequence of SACT (SEQ ID NO: 1) is shown below:

```
ATGGGAATCCAAGGAGGGTCTGTCCTGTTCGGGCTGCTGCTCGTCCTG
GCTGTCTTCTGCCATTCAGGTCATAGCGGATGTGAGGAGCCACCAACA
TTTGAAGCTATGGAGCTCATTGGTAAACCAAAACCCTACTATGAGATT
GGTGAACGAGTAGATTATAAGTGTAAAAAAGGATACTTCTATATACCT
CCTCTTGCCACCCATACTATTTGTGATCGGAATCATACATGGCTACCT
GTCTCAGATGACGCCTGTTATAGAGAAACATGTCCATATATACGGGAT
CCTTTAAATGGCCAAGCAGTCCCTGCAAATGGGACTTACGAGTTTGGT
TATCAGATGCACTTTATTTGTAATGAGGGTTATTACTTAATTGGTGAA
GAAATTCTATATTGTGAACTTAAAGGATCAGTAGCAATTTGGAGCGGT
AAGCCCCCAATATGTGAAAAGGTTTTGTGTACACCACCTCCAAAAATA
AAAAATGGAAAACACACCTTTAGTGAAGTAGAAGTATTTGAGTATCTT
GATGCAGTAACTTATAGTTGTGATCCTGCACCTGGACCAGATCCATTT
TCACTTATTGGAGAGAGCACGATTTATTGTGGTGACAATTCAGTGTGG
AGTCGTGCTGCTCCAGAGTGTAAAGTGGTCAAATGTCGATTTCCAGTA
GTCGAAAATGGAAAACAGATATCAGGATTTGGAAAAAAATTTTACTAC
AAAGCAACAGTTATGTTTGAATGCGATAAGGGTTTTTACCTCGATGGC
AGCGACACAATTGTCTGTGACAGTAACAGTACTTGGGATCCCCCAGTT
CCAAAGTGTCTTAAAGTGGGAGGCGGAGGTGGAGGTGACTGTGGCCTT
CCCCCAGATGTACCTAATGCCCAGCCAGCTTTGGAAGGCCGTACAAGT
TTTCCCGAGGATACTGTAATAACGTACAAATGTGAAGAAAGCTTTGTG
AAAATTCCTGGCGAGAAGGACTCAGTGATCTGCCTTAAGGGCAGTCAA
TGGTCAGATATTGAAGAGTTCTGCAATCGTAGCTGCGAGGTGCCAACA
AGGCTAAATTCTGCATCCCTCAAACAGCCTTATATCACTCAGAATTAT
TTTCCAGTCGGTACTGTTGTGGAATATGAGTGCCGTCCAGGTTACAGA
AGAGAACCTTCTCTATCACCAAAACTAACTTGCCTTCAGAATTTAAAA
TGGTCCACAGCAGTCGAATTTTGTAAAAAGAAATCATGCCCTAATCCG
GGAGAAATACGAAATGGTCAGATTGATGTACCAGGTGGCATATTATTT
GGTGCAACCATCTCCTTCTCATGTAACACAGGGTACAAATTATTTGGC
TCGACTTCTAGTTTTTGTCTTATTTCAGGCAGCTCTGTCCAGTGGAGT
GACCCGTTGCCAGAGTGCAGAGAAATTTATTGTCCAGCACCACCACAA
ATTGACAATGGAATAATTCAAGGGAACGTGACCATTATGGATATAGA
CAGTCTGTAACGTATGCATGTAATAAAGGATTCACCATGATTGGAGAG
CACTCTATTTATTGTACTGTGAATAATGATGAAGGAGAGTGGAGTGGC
CCACCACCTGAATGCAGAGGAAATCTCTAACTTCCAAGGTCCCACCA
ACAGTTCAGAAACCTACCACAGTAAATGTTCCAACTACAGAAGTCTCA
CCAACTTCTCAGAAAACCACCACAAAAACCACCACACCCAAATGCTCAA
GCAACACGGAGTACACCTGTTTCCAGGACAACCAAGCATTTTCATGAA
ACAACCCCAAATAAAGGAAGTGGAACCACTTCAGGTACTACCGGCGGA
GGTGGAGGTCTGCAGTGCTACAACTGTCCTAACCCAACTGCTGACTGC
AAAACAGCCGTCAATTGTTCATCTGATTTTGATGCGTGTCTCATTACC
AAAGCTGGGTTACAAGTGTATAACAAGTGTTGGAAGTTTGAGCATTGC
```
```
AATTTCAACGACGTCACAACCCGCTTGAGGGAAAATGAGCTAACGTAC
TACTGCTGCAAGAAGGACCTGTGTAACTTTAACGAACAGCTTGAATGA
TGA
```

The amino acid sequence of SACT (SEQ ID NO: 2) is shown below:

```
MGIQGGSVLFGLLLVLAVFCHSGHSGCEEPPTFEAMELIGKPKPYYEI
GERVDYKCKKGYFYIPPLATHTICDRNHTWLPVSDDACYRETCPYIRD
PLNGQAVPANGTYEFGYQMHFICNEGYYLIGEEILYCELKGSVAIWSG
KPPICEKVLCTPPPKIKNGKHTFSEVEVFEYLDAVTYSCDPAPGPDPF
SLIGESTIYCGDNSVWSRAAPECKVVKCRFPVVENGKQISGFGKKFYY
KATVMFECDKGFYLDGSDTIVCDSNSTWDPPVPKCLKVGGGGGDCGL
PPDVPNAQPALEGRTSFPEDTVITYKCEEESFVKIPGEKDSVICLKGSQ
WSDIEEFCNRSCEVPTRLNSASLKQPYITQNYFPVGTVVEYECRPGYR
REPSLSPKLTCLQNLKWSTAVEFCKKKSCPNPGEIRNGQIDVPGGILF
GATISFSCNTGYKLFGSTSSFCLISGSSVQWSDPLPECREIYCPAPPQ
IDNGIIQGERDHYGYRQSVTYACNKGFTMIGEHSIYCTVNNDEGEWSG
PPPECRGKSLTSKVPPTVQKPTTVNVPTTEVSPTSQKTTTKTTTPNAQ
ATRSTPVSRTTKHFHETTPNKGSGTTSGTTGGGGLQCYNCPNPTADC
KTAVNCSSDFDACLITKAGLQVYNKCWKFEHCNFNDVTTRLRENELTY
YCCKKDLCNFNEQLE
```

The nucleotide sequence of DTAC (SEQ ID NO: 3) is shown below:

```
ATGGGAATCCAAGGAGGGTCTGTCCTGTTCGGGCTGCTGCTCGTCCTG
GCTGTCTTCTGCCATTCAGGTCATAGCGGAGGTGACTGTGGCCTTCCC
CCAGATGTACCTAATGCCCAGCCAGCTTTGGAAGGCCGTACAAGTTTT
CCCGAGGATACTGTAATAACGTACAAATGTGAAGAAAGCTTTGTGAAA
ATTCCTGGCGAGAAGGACTCAGTGATCTGCCTTAAGGGCAGTCAATGG
TCAGATATTGAAGAGTTCTGCAATCGTAGCTGCGAGGTGCCAACAAGG
CTAAATTCTGCATCCCTCAAACAGCCTTATATCACTCAGAATTATTTT
CCAGTCGGTACTGTTGTGGAATATGAGTGCCGTCCAGGTTACAGAAGA
GAACCTTCTCTATCACCAAAACTAACTTGCCTTCAGAATTTAAAATGG
TCCACAGCAGTCGAATTTTGTAAAAAGAAATCATGCCCTAATCCGGGA
GAAATACGAAATGGTCAGATTGATGTACCAGGTGGCATATTATTTGGT
GCAACCATCTCCTTCTCATGTAACACAGGGTACAAATTATTTGGCTCG
ACTTCTAGTTTTTGTCTTATTTCAGGCAGCTCTGTCCAGTGGAGTGAC
CCGTTGCCAGAGTGCAGAGAAATTTATTGTCCAGCACCACCACAAATT
GACAATGGAATAATTCAAGGGAACGTGACCATTATGGATATAGACAG
TCTGTAACGTATGCATGTAATAAAGGATTCACCATGATTGGAGAGCAC
TCTATTTATTGTACTGTGAATAATGATGAAGGAGAGTGGAGTGGCCCA
```

-continued
```
CCACCTGAATGCAGAGGAAAATCTCTAACTTCCAAGGTCCCACCAACA

GTTCAGAAACCTACCACAGTAAATGTTCCAACTACAGAAGTCTCACCA

ACTTCTCAGAAAACCACCACAAAAACCACCACACCAAATGCTCAAGCA

ACACGGAGTACACCTGTTTCCAGGACAACCAAGCATTTTCATGAAACA

ACCCCAAATAAAGGAAGTGGAACCACTTCAGGTACTACCGGCGGAGGT

GGAGGTCTGCAGTGCTACAACTGTCCTAACCCAACTGCTGACTGCAAA

ACAGCCGTCAATTGTTCATCTGATTTTGATGCGTGTCTCATTACCAAA

GCTGGGTTACAAGTGTATAACAAGTGTTGGAAGTTTGAGCATTGCAAT

TTCAACGACGTCACAACCCGCTTGAGGGAAAATGAGCTAACGTACTAC

TGCTGCAAGAAGGACCTGTGTAACTTTAACGAACAGCTTGAATGATGA
```

The amino acid sequence of DTAC (SEQ ID NO: 4) is shown below:

```
MGIQGGSVLFGLLLVLAVFCHSGHSGGDCGLPPDVPNAQPALEGRTSF

PEDTVITYKCEESFVKIPGEKDSVICLKGSQWSDIEEFCNRSCEVPTR

LNSASLKQPYITQNYFPVGTVVEYECRPGYRREPSLSPKLTCLQNLKW

STAVEFCKKKSCPNPGEIRNGQIDVPGGILFGATISFSCNTGYKLFGS

TSSFCLISGSSVQWSDPLPECREIYCPAPPQIDNGIIQGERDHYGYRQ

SVTYACNKGFTMIGEHSIYCTVNNDEGEWSGPPPECRGKSLTSKVPPT

VQKPTTVNVPTTEVSPTSQKTTTKTTTPNAQATRSTPVSRTTKHFHET

TPNKGSGTTSGTTGGGGLQCYNCPNPTADCKTAVNCSSDFDACLITK

AGLQVYNKCWKFEHCNFNDVTTRLRENELTYYCCKKDLCNFNEQLE
```

The sequence listing material in computer readable form ASCII text file (21 kilobytes) created Feb. 22, 2017 entitled "34724-174_SequListing_02282017", containing sequence listing numbers 1-5, has been electronically filed herewith and is incorporated by reference herein in its entirety.

Example 3

Construction of Adeno-Associated Virus (AAV) Constructs

Recombinant AAV was generated via triple transfection of 293 cells with each of pAAV2CAGSACT, pAAV2CAGDTAC and pAAV2CAGGFP, pHelper (Stratagene) and pAAV2/8Rep/Cap (Cashman, S. M., et al. 2011 PLoS One 6: e19078). The resulting AAV vectors, AAV2/8SACT, AAV2/8DTAC and AAV2/8GFP were purified by iodixanol gradient and dialyzed in Ringer's lactate buffer (Zolotukhin, S. 2005 Hum Gene Ther 16: 551-557). Viral genomes were titered by real-time quantitative PCR using primers targeting AAV2 inverted terminal repeats (ITRs) as described in (Fagone, P., et al. 2012 Hum Gene Ther Methods 23: 1-7).

Example 4

Western Blot Analyses

The human embryonic retinoblast, 911, cell line was transfected with pAAV2CAGDTAC, pAAV2CAGSACT or pAAV2CAGGFP using Lipofectamine 2000 as per manufacture's protocol (Invitrogen). 72 hours post-transfection, media was collected, centrifuged and electrophoresed on a 10% Tris-HCl gel and proteins were subsequently transferred to a nitrocellulose membrane, probed with a mouse anti-human CD46 antibody (MEM258, Serotec) at a dilution of 1:10,000; a goat anti-human CD55 antibody (AF2009, R&D systems, Minneapolis, Minn.) at a dilution of 1:20,000 or a rabbit anti-human CD59 antibody (ab124396, Abcam) at a dilution of 1:5,000. An IRDye linked secondary antibody was used followed by detection with the Odyssey Li-Cor System (Li-Cor Biosciences, Lincoln, Nebr.).

Example 5

Complement Assays with Hepa1c1c7 Cells

For FACS analyses, hepa1c1c7 cells were plated in αMEM/2% FBS without phenol red at 50% confluency. After three days, the hepa1c1c7 cells were collected by trypsinization (0.25% EDTA) and resuspended in 1× phosphate-buffered saline (PBS) containing 0.5% FBS. $5 \times 10^5$ cells were centrifuged at 1200 RPM/4° C. and resuspended in 500 μl of media from 911 cells transfected with pDTAC, pSACT or pGFP. Normal human serum (NHS; Complement Technology, Tyler, Tex.) or heat-inactivated (hi; 56° C. for one hour) NHS was added to each sample to a final concentration of 1% and samples were incubated with constant rotary motion at 37° C. for one hour. Cell lysis was determined using the propidium iodide (PI) exclusion method in which 1 μl of PI (2 mg/ml) was added to each sample and 25,000 cells were counted by FACS (FACS Calibur) for PI uptake (CellQuest Pro software, Becton Dickinson).

For in vitro MAC deposition, 35,000 hepa1c1c7 cells were seeded per well in an eight well chamber slide (Becton Dickinson) in αMEM/2% FBS. 24 hours later, media was removed and the cells were washed three times with 1×PBS and the cells were incubated with 10% NHS or hiNHS resuspended in media from 911 cells transfected with pDTAC, pSACT or pGFP for 10 minutes at 37° C. Cells were then washed twice with cold 1×PBS and fixed for 15 minutes with 3.7% formaldehyde. Cells were stained for MAC deposition as described in examples herein.

Example 6

Hemolytic Assays

Sensitized sheep erythrocytes (Complement Technology) were washed twice with Gelatin Veronal Buffer (GVB2+) and suspended to a concentration of $5 \times 10^8$ cells/ml then 25 μl of erythrocyte suspension was used per reaction. 125 μl of media from either pGFP-, pDTAC- or pSACT-transfected 911 cells containing NHS to a final concentration of 0.3% was added to the erythrocyte suspension. The erythrocytes were incubated for one hour at 37° C., centrifuged at 500×g for four minutes at 4° C. and absorbance of the resultant supernatant was read at 405 nm (Filter Max F5 multi-mode microplate reader, Molecular Devices; Sunnyvale, Calif.).

For CD55 blocking assays, media from pGFP-, pDTAC- or pSACT-transfected 911 cells that had been incubated with or without anti-CD55 antibody (ab33111, Abcam; Boston, Mass.) at room temperature for 30 min was added to the erythrocytes along with 0.3% NHS. After a one hour incubation at 37° C., supernatant was collected and absorbance was read as described in examples herein.

For C9-incorporation assays, suspended erythrocytes were incubated with 0.1% C9-depleted serum (Complement Technology) for one hour at 37° C. to permit formation of the C5b-8 complex. After washing twice with GVB2+, media from pGFP-, pDTAC- or pSACT-transfected 911 cells that had been pre-incubated on ice for 30 minutes in the presence or absence of 0.04 μg/ml C9 (Complement Technology) was added. Following a 30-minute incubation at 37° C., samples were centrifuged and absorbance was determined, as described in 49). Data from hemolytic assays were normalized to the amount of lysis of erythrocytes in media from pGFP-transfected cells (set at 100% lysis).

Example 7

Factor I Cofactor Activity

In vitro cofactor activity was assayed as described in (Johnson, J. B., et al. 2009 J Virol 83: 7602-7611). Media from pGFP-, pDTAC- or pSACT-transfected 911 cells was incubated with 3 μg of C3b, plus 100 ng of factor I in a total volume of 20 μl at 37° C. for four hours. Reactions were terminated by adding 5 μl of SDS-PAGE sample buffer containing β-mercaptoethanol and boiling. C3b reaction products were analyzed by western blot using a 10% SDS-PAGE gel. The gel was transferred to a membrane and the membrane was probed with polyclonal goat anti-human C3 (A213, Complement Technology) at a dilution of 1:1,000. Data were normalized using the signal intensity of the uncleaved β chain of C3b.

Example 8

Degradation of Alternative Pathway C3 Convertase

Microtiter plates were coated with 0.1% agarose in water and dried for 36 hours at 37° C., then the wells were blocked with 1% bovine serum albumin in PBS for two hours at room temperature as described in (Happonen, K. E., et al. 2012 J Biol Chem 287: 8092-8100). NHS diluted in $Mg^{2+}$ EGTA was added to the agarose-coated plate and incubated at 37° C. for one hour. Following washing, media from pGFP-, pDTAC- or pSACT-transfected 911 cells were added to the plate and the plates were incubated at 37° C. for one hour. Factor B remaining bound to the plate was detected using a factor B (A235, Complement Technologies) specific antibody followed by HRP-conjugated secondary antibody.

Example 9

In Vivo Liver MAC Deposition Assay

The method was a protocol described in Gandhi, J., et al. 2011 PLoS One 6: e21621. Subjects were 6-10 week old C57BL/6J mice and were injected intraperitoneally with $3.3 \times 10^{11}$ genome copies of AAV2/8DTAC, AAV2/8 SACT, or AAV2/8polyA. After three weeks, the mice were injected intracardially with 200 μg of anti-mouse PECAM antibody (clone 2H8, 1.4 mg/mL, prepared as described in examples herein). After 4-6 hour incubation, the mice underwent a cardiac perfusion of 1 ml of gelatin veronal buffer (GVB2+) followed by 1.5 ml of 90% NHS (Complement Technology Inc., Tyler, Tex.) in GVB2+. Following a 15 minute incubation at 37° C., the median lobe of the liver was harvested and fixed overnight in 4% paraformaldehyde at 4° C. Cryosections of 8 μm were obtained and stained for MAC as described in examples herein. Imaging was performed using an Olympus IX51 microscope equipped with a Retiga 2000r camera. Intensity of MAC staining over the entire section and around the vessels was quantified using ImageJ software (National Institutes of Health; Bethesda, Md., USA). Large blood vessels were defined as those with a diameter larger than two cell widths and include arteries, arterioles, veins and venules and exclude capillaries and sinusoids. The outer and inner boundaries of the large blood vessels were traced using the free-hand selection tool and total intensity and total area was calculated for each using the measure function. To calculate the average vessel intensity, the following equation was utilized: $X = [I_{outer} - I_{inner}] / [A_{outer} - A_{inner}]$.

Example 10

Immunohistochemistry

To detect MAC deposition on hepa1c1c7 cells, cells were incubated for 2.5 hours at room temperature with mouse anti-human C5b-9 (1:100) (ab66768, Abcam, Cambridge, Mass.) in 0.05% triton containing 6% normal goat serum (NGS). Cy3 conjugated goat anti mouse (1:200) in 0.05% triton containing 3% NGS for one hour at room temperature was used for secondary detection. For detection of MAC deposition on liver vasculature, liver sections were incubated for 2.5 hours at room temperature with rabbit anti-human C5b-9 (Complement Technology, Tyler, Tex.) (1:400) in 0.5% triton, following a one hour blocking with 6% normal goat serum (NGS) and 0.5% triton. Cy3-conjugated goat anti-rabbit (1:200) was used for one hour at room temperature for secondary detection.

Images were captured using an Olympus IX51 microscope and ImageJ software was used to quantify fluorescence. Raw fluorescence units were measure and background for each image was subtracted. All statistical analyses were performed using Prism Software 5.0a (GraphPad Software Inc., La Jolla, Calif., USA).

Example 11

Design and Synthesis of SACT and DTAC

A plasmid containing an expression cassette for Soluble Active Complement Terminator (SACT) was generated. SACT includes an engineered DNA sequence designed to express a protein composed of the four short consensus repeat (SCR) domains of human CD46 separated by a polyglycine linker from the four SCR domains and serine/threonine (S/T)-rich region of human CD55. An additional polyglycine linker separates the S/T-rich region of CD55 from the functional domain (amino acids 1-76) of human CD59 (FIG. 1A). The N terminus of SACT contains a secretory signal derived from the native human CD59. The membrane-spanning domain of CD46 and the signals for attachment of a GPI-anchor to each of CD55 and CD59 are not included in the recombinant protein therefore, SACT does not anchor to the plasma membrane (FIG. 1A).

A smaller recombinant protein Dual Terminator of Active Complement (DTAC) was also generated which is a protein engineered to contain the four SCR domains and S/T-rich region of human CD55 separated by a poly glycine linker from the functional domain (as described in examples herein) of human CD59. DTAC contains the secretory peptide of human CD59 (FIG. 1A). DTAC is rendered membrane-independent by engineering the protein to omit the CD55 and CD59 signal peptides for attachment of a GPI-anchor.

To express SACT in vivo using a gene therapy approach, a cDNA encoding SACT was inserted into the plasmid, pAAVCAG, containing adeno-associated virus serotype 2

(AAV2) inverted terminal repeats to generate pSACT (Cashman, S. M., et al. 2011 PLoS One 6: e19078). As a negative control, the same construct devoid of the SACT cDNA was used and referred to as pAAVCAG. A cDNA encoding DTAC was inserted into pAAVCAG for expression from an AAV2 virus, generating pDTAC.

Example 12

SACT and DTAC are Secreted Proteins

The predicted molecular weight of SACT and DTAC proteins are 76 kDa and 47 kDa respectively (Serial Cloner 2.6.1; Serial Basic Software). Both CD46 and CD55 contain N- and O-linked glycosylation sites (Coyne, K. E., et al. 1992 J Immunol 149: 2906-2913, Ballard, L. L., et al. 1988 J Immunol 141: 3923-3929). These modifications increase the molecular weight of CD46 and CD55 by ~8 kDa (Ballard, L. L., et al. 1988 J Immunol 141: 3923-3929) and ~29 kDa respectively (Coyne, K. E., et al. 1992 J Immunol 149: 2906-2913). Given the number of glycosylation sites retained by SACT and DTAC, the expected molecular weight of SACT and DTAC was determined to be approximately 105-113 kDa and 76 kDa, respectively. For western blot analyses of media from pSACT-transfected human embryonic 911 retinoblasts (HER) were probed with antibodies for CD46, CD55 or CD59 and a protein band of approximately 110 kDa, which is consistent with the predicted molecular weight of glycosylated SACT was observed. This 110 kDa band was absent in media from pGFP or pDTAC transfected cells (FIG. 1B) (Fallaux, F. J., 1996 Hum Gene Ther 7: 215-222). For western blot analyses of pDTAC-transfected cells were probed with the above antibodies and data indicated the presence of a ~76 kDa band, consistent with the predicted molecular weight of glycosylated DTAC. This band was absent in media from cells transfected with pGFP or pSACT (FIG. 1B). This 76 kDa protein was observed only for membrane probed with antibodies against CD55 and CD59 and showed no reactivity to antibody for CD46 (FIG. 1B). Therefore, SACT and DTAC are secreted, and these protein each contain the expected combination of complement regulatory domains and glycosylation sites.

Example 13

SACT Acts as a Co-Factor for Factor I Mediated Cleavage of C3b

Figure 2A:
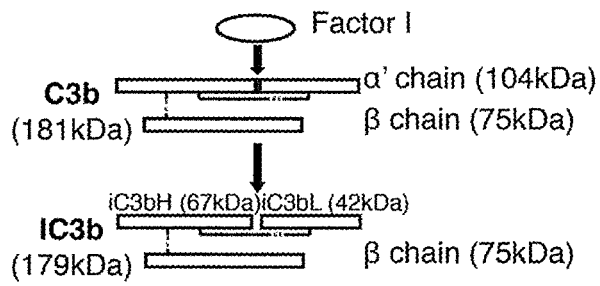
FIG. 2A, FIG. 2B, FIG. 2C and FIG. 2D are schematic drawings, a photograph and a bar graph showing that SACT acts as a co-factor for Factor I mediated cleavage of C3b.
Figure 2B:
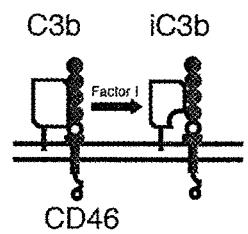
Figure 2B:
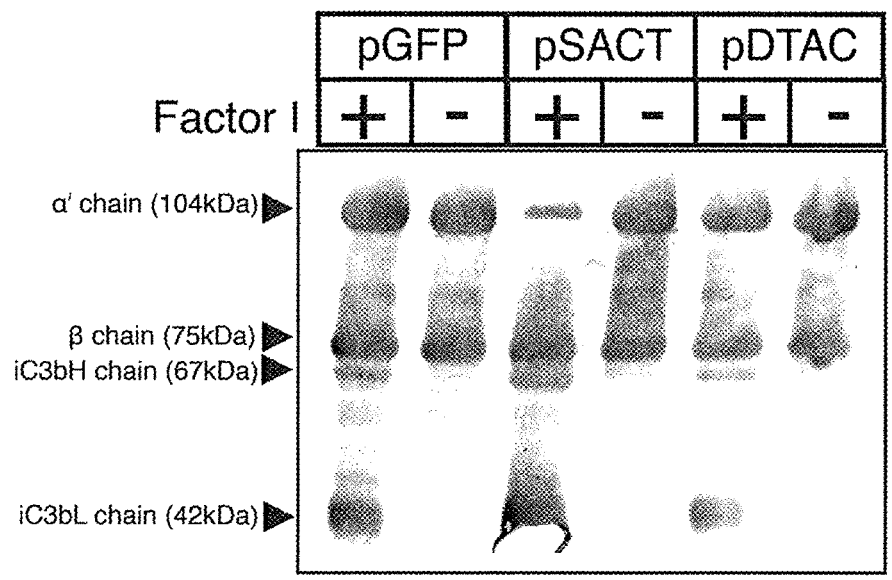

Spontaneous 'tickover' of the alternative pathway of the complement system results in the formation of C3b on cell surfaces (Walport, M. J. 2001 N Engl J Med 344: 1058-1066). The amount of C3b present is regulated by proteolytic cleavage of C3b by the serine protease Factor I. Factor I cleaves the 104 kDa α' chain of C3b into inactivated 67 kDa iC3bH and 42 kDa iC3bL chains respectively (FIG. 2A) (Riley-Vargas, R. C., et al. 2004 Immunol 25: 496-503). CD46 functions as a co-factor for Factor I, and accelerates the formation of iC3bH and iC3bL (FIG. 2B).

Figure 2C:
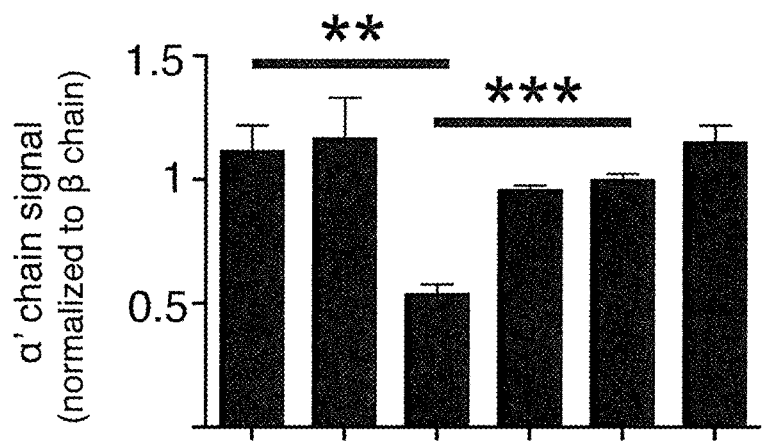

To examine whether SACT exhibits cofactor properties similar to CD46, 3 μg of C3b were incubated in media prepared from 911 cells transfected with pSACT, pDTAC or pGFP. Incubations were performed in the presence or absence of 100 ng Factor I (Cashman, S. M., et al. 2011 PLoS One 6: e19078). The relative amount of 104 kDa α' chain of C3b remaining after four hours of incubation was measured by quantitative western blot using a polyclonal anti-C3 antibody (FIG. 2C). The uncleaved β chain of C3b was used to normalize the data.

Figure 2D:
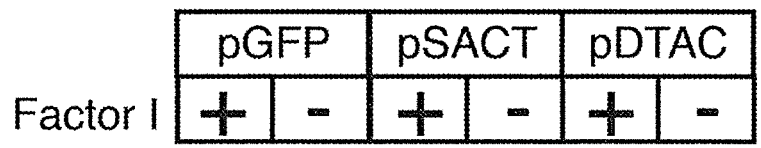

Media from pSACT-transfected cells containing C3b and Factor I was observed to have had a 51.8±10.5% (p=0.007) reduction in the amount of the 104 kDa α' chain of C3b relative to media from pGFP-transfected cells containing C3b and Factor I, and a 46.2±4.8% (p=0.0007) reduction relative to media from pDTAC-transfected cells containing C3b and Factor I (FIG. 2D). There was no significant difference (p=0.34) between the amount of 104 kDa α' chain of C3b exposed to the media of pGFP and pDTAC transfected cells containing C3b and Factor I (FIG. 2D). Therefore, SACT can act as a cofactor for Factor I mediated cleavage of C3b.

Example 14

SACT and DTAC Accelerate Degradation of the C3-Convertase

Binding of Factor B to membrane associated C3b results in the formation of the C3 convertase (Walport, M. J. 2001 N Engl J Med 344: 1058-1066). CD55 can prevent binding of Factor B to C3b, and cause dissociation of Factor B from C3b, thereby reducing the amount of C3 convertase available for further activation of complement (FIG. 3A) (Walport, M. J. 2001 N Engl J Med 344: 1058-1066). To determine whether SACT or DTAC could dissociate Factor B from C3b and reduce C3 convertase activity, the amount of Factor B remaining in association with C3b immobilized on agarose on incubation in the presence of SACT or DTAC was quantified. Agarose-coated microtiter plates were incubated with normal human serum (NHS) in the presence of Mg2+EGTA to allow formation of the alternative pathway C3 convertase. The wells were subsequently incubated with media from pSACT-, pDTAC- or pGFP-transfected 911 cells. The amount of Factor B associated with the agarose-bound C3b after one hour at 37° C. was determined by antibody staining for Factor B following numerous washes to remove unbound Factor B. Quantification of Factor B staining indicated that relative to media from pGFP-transfected 911 cells, media from pDTAC- or pSACT-transfected cells resulted in a 16.1±6.4% (p=0.0214) and 16.8±6.1% (p=0.0127) reduction in C3b-bound Factor B, respectively (FIG. 3B). Therefore, DTAC and SACT accelerate the decay of the C3 convertase.

Example 15

A CD55 Blocking Antibody Reduces the Ability of SACT and DTAC to Protect Against Complement-Mediated Cell Lysis To analyze the function of the CD55-derived SCRs in SACT and DTAC, human complement-mediated lysis of sensitized sheep erythrocytes in the presence of media from either pSACT- or pDTAC-transfected 911 cells in the presence of CD55 blocking antibody was quantified. At an antibody concentration of 1 mg/ml, the ability of media from pDTAC- and pSACT-transfected cells to protect sheep erythrocytes from human complement was observed to be reduced by 40.4%±1.84% (p<0.0001) and 14.2%±2.88% (p=0.0006) respectively relative to media from transfected 911 cells without blocking antibody (FIG. 3C). At lower concentrations (250 ng/ml) of blocking antibody, the ability of media from pDTAC- and pSACT-transfected cells to protect sheep erythrocytes from lysis was observed to be reduced by 7.33%±2.66% (p=0.02) and 11.2%±3.09% (p=0.0046) respectively relative to media from transfected cells without blocking antibody (FIG. 3C). Therefore, the CD55-derived SCRs in SACT and DTAC are functionally active.

Example 16

SACT and DTAC Attenuate Recruitment of C9 into the Membrane Attack Complex

Figure 4A:
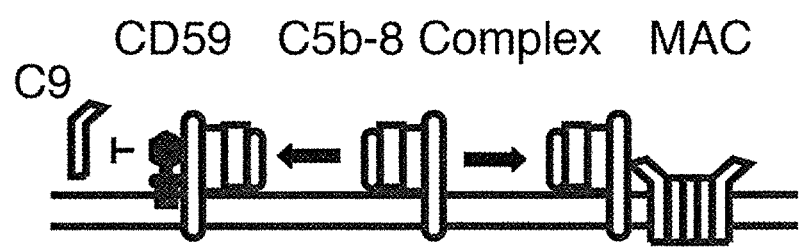
FIG. 4A and FIG. 4B are a schematic drawing and a bar graph showing that SACT and DTAC inhibit incorporation of C9 into the membrane attack complex.

Formation of the membrane attack complex (MAC) begins with the assembly of the C5b-8 complex on the cell membrane, followed by the recruitment and polymerization of multiple units of C9 to form the lytic pore known as MAC (Walport, M. J. 2001 N Engl J Med 344: 1058-1066). CD59 acts as an inhibitor of MAC formation by preventing the recruitment and polymerization of C9 (FIG. 4A) (Zipfel, P. F., et al. 2009 Nat Rev Immunol 9: 729-740).

Figure 4B:
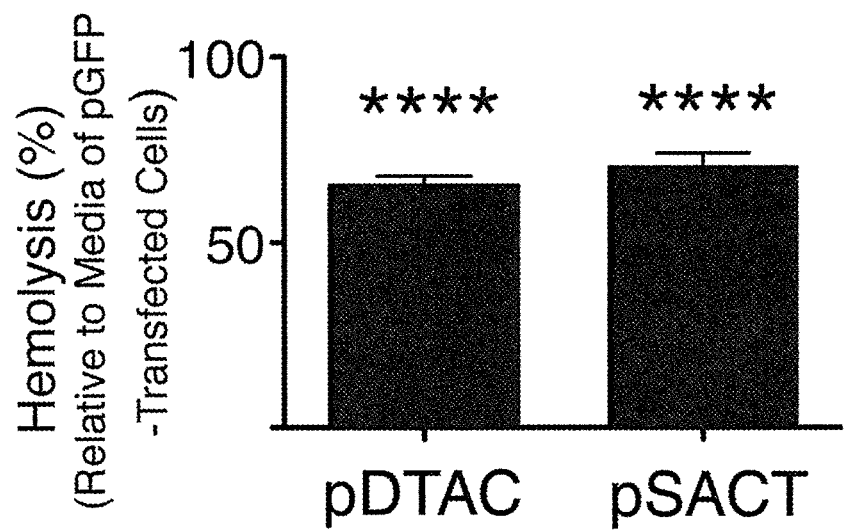

To determine whether the CD59 module of SACT or DTAC can attenuate recruitment of C9 into MAC, antibody-sensitized sheep erythrocytes were incubated with C9-depleted NHS to permit assembly of the C5b-8 complex on the cell surface. Purified C9 protein was subsequently added with media from pDTAC- or pSACT-transfected 911 cells and formation of the MAC was measured by quantification of hemoglobin released due to lysis of the sheep erythrocytes. It was observed that media from pDTAC- and pSACT-transfected 911 cells reduced the release of hemoglobin from sheep erythrocytes by 34.8±3.6% (p<0.0001) and 29.9±4.6% (p<0.0001) respectively relative to erythrocytes incubated with NHS in the presence of media from pGFP-transfected cells (FIG. 4B). Therefore, DTAC and SACT attenuate the recruitment of C9 into the MAC, a property which is consistent with the presence of functional CD59.

Example 17

Figure 5A:
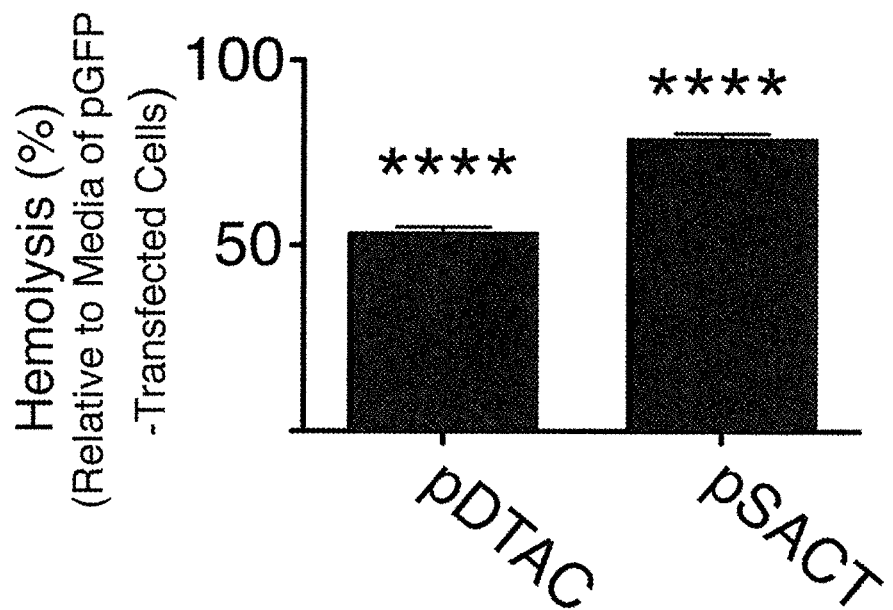
FIG. 5A and FIG. 5B are bar graphs showing that SACT and DTAC protect both sheep erythrocytes and murine hepatocytes from human complement-mediated lysis in vitro.

SACT and DTAC Attenuate Human Complement-Mediated Lysis of Hepatocytes In Vitro To determine whether DTAC or SACT protects sheep erythrocytes from NHS mediated cell lysis, IgG-sensitized sheep erythrocytes were incubated in NHS pre-conditioned with media from pDTAC, pSACT or pGFP transfected 911 cells. pDTAC and pSACT transfected media were observed to have reduced NHS mediated lysis of sheep erythrocytes by 47±2.9% (p<0.0001) and 21.5±2.8% (p<0.0001) respectively (FIG. 5A), compared to pGFP transfected media. These data indicate that DTAC and SACT attenuates NHS mediated cell lysis.

Figure 5B:
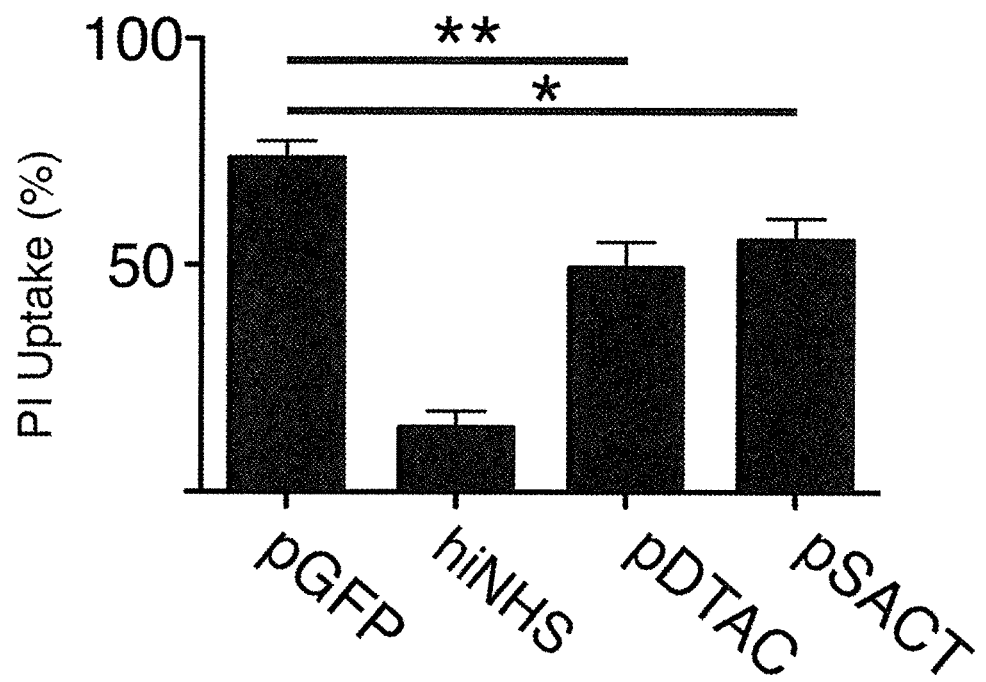

Complement mediated attack of transplanted organs, such as liver and kidney, is considered a primary cause of transplant rejection (Satoh, S., 1997 Transplantation 64: 1117-1123). To determine whether SACT and DTAC can protect hepatocytes from human complement attack, murine hepa-1c1c7 cells were incubated in media from pDTAC-, pSACT- or pGFP-transfected 911 cells containing NHS or heat inactivated NHS (hiNHS) to a final concentration of 1%. Cell lysis was quantified by FACS analysis of propidium iodide uptake. A total of 73.5±3.79% of cells were observed to be lysed in hepa-1c1c7 cells incubated with NHS pre-conditioned with media from pGFP-transfected cells (FIG. 5B). On the contrary, 49.3±5.7% and 55.5±4.8% of cells were observed to be lysed in the NHS that was pre-conditioned with media from DTAC or SACT respectively, resulting in a 28.7%±10.2% (p=0.014) or 20.8±9.0% (p=0.037) reduction in NHS mediated cell lysis attributable to DTAC and SACT, respectively (FIG. 5B). This result indicates that DTAC and SACT protects murine hepatocytes from human complement mediated attack.

Example 18

DTAC and SACT Reduce Formation of the Membrane Attack Complex In Vitro

Figure 6A:
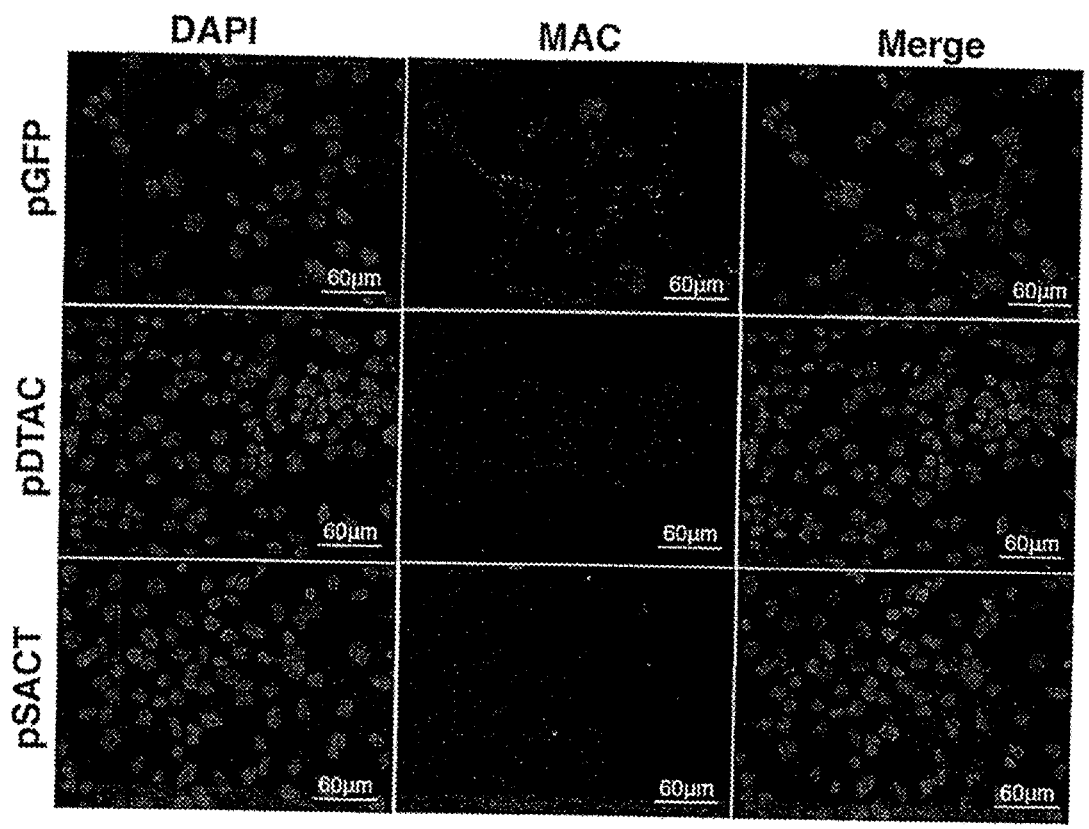
FIG. 6A and FIG. 6B are micrographs and a bar graph showing that DTAC and SACT reduce deposition of the Membrane Attack Complex in vitro.
Figure 6B:
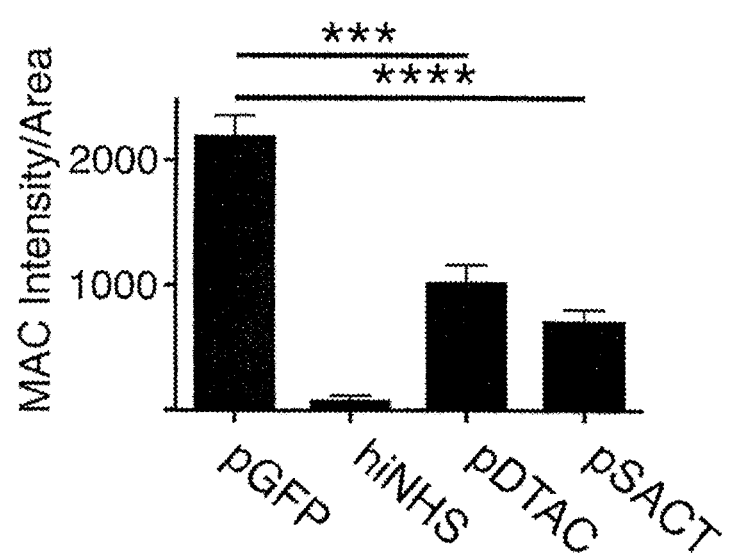

To determine whether DTAC or SACT-mediated reduction in lysis of hepatocytes was consistent with a reduction in formation of the MAC on the cell membrane, murine hepa1c1c7 cells were incubated in media from pGFP-, pDTAC- or pSACT-transfected 911 cells containing 10% NHS. Cells were subsequently fixed and stained with antibody against human C5b-9 and staining intensity was quantified using Image J (FIG. 6A). The media from pDTAC- and pSACT-transfected cells were observed to have a 53.8±10.37% (p=0.0004) and 67.8±9.15% (p<0.0001) reduction in MAC deposition on murine hepatocytes, respectively compared to media from pGFP-transfected cells (FIG. 6B). Therefore, DTAC and SACT-mediated reduction of cell lysis causes a reduced formation of the MAC on the surface of cells.

Example 19

SACT and DTAC Protect Murine Liver from Human MAC Deposition In Vivo

A number of complement-mediated pathologies, including organ transplant rejection, have been shown to involve endothelial cells (Zipfel, P. F., et al. 2009 Nat Rev Immunol 9: 729-740, Satoh, S., 1997 Transplantation 64: 1117-1123, Anderson, D. H., et al. 2010 Prog Retin Eye Res 29: 95-112). To overcome the limitation of testing the ability of human complement regulators to protect murine endothelium from complement attack in vivo, an in vivo model was developed for human MAC deposition on murine liver vascular endothelium (Gandhi, J., et al. 2011 PLoS One 6: e21621). In this model, murine vascular endothelium is primed for complement attack by intracardial injection of an antibody against murine platelet/cell adhesion molecule (mPECAM-1). The injection is followed by perfusion with PBS to replace the blood and a subsequent perfusion with 90% NHS. Using this model, it has been shown that adenovirus mediated expression of human soluble CD59 can inhibit deposition of human MAC on murine liver (Gandhi, J., et al. 2011 PLoS One 6: e21621).

To examine whether SACT or DTAC can protect murine liver vasculature from human MAC deposition, each of the pSACT, pDTAC, and pGFP plasmids were used to generate a recombinant adeno-associated virus (AAV) serotype 2 pseudotyped with AAV serotype 8 capsid for each recombinant protein. An AAV2/8 construct devoid of a transgene was described in Cashman, S. M., et al. 2011 PLoS One 6: e19078. These vectors are referred to as AAV2/8SACT, AAV2/8DTAC, AAV2/8GFP and AAV2/8polyA, respectively.

To examine the tropism of AAV2/8 in murine liver, $3.3 \times 10^{11}$ genome copies of AAV2/8GFP were injected into the peritoneum of 6 to 8 week old C57BL/6J mice. After 3 weeks, mice were sacrificed, livers harvested and cryosections examined for GFP expression. GFP expression from AAV2/8GFP was observed to be throughout the liver, including cells proximal to blood vessels and sinusoids (FIG. 7A). These results contrast with previous studies utilizing an adenovirus vector expressing GFP from the same CAG promoter, in which it was observed that GFP expression was almost exclusively in the capsule of the liver following intraperitoneal delivery of the vector (Gandhi, J., et al. 2011 PLoS One 6: e21621).

Having observed efficient transduction of murine liver with AAV2/8GFP, mice were injected intraperitoneally with a similar titer of AAV2/8DTAC, AAV2/8SACT or AAV2/8polyA. Three weeks post-injection with AAV, the mice were administered an intracardial injection of mPECAM-1 and followed by perfusion with 90% NHS after about 4-6 hours. After about 15 minutes, the livers were harvested for cryosectioning and stained for human MAC using antibody against C5b-9 (FIG. 7B; 8A). MAC staining was observed in the blood vessels and sinusoids of the livers of mice injected with AAV2/8polyA (FIGS. 7B; 8A). Mice injected with either AAV2/8DTAC or AAV2/8SACT had significantly less MAC deposition on both liver blood vessels and sinusoids relative to control (AAV2/8polyA)-injected mice (FIGS. 7C; 8B). Quantification of MAC staining intensity using ImageJ indicated a 56.7±16.4% (p=0.0061) reduction in human MAC deposition on the liver vasculature of AAV2/8DTAC-injected relative to AAV2/8polyA-injected mice (FIG. 7C). Similarly, AAV2/8SACT-injected animals showed a 63.2%±20.5% (p=0.0075) reduction in human MAC deposition in their liver vasculature relative to AAV2/8polyA-injected mice (FIG. 8B). Endothelial cells of both the sinusoids and blood vessels indicated deposition of MAC. Quantification of larger (non-capillary) blood vessels of the liver indicated a significant reduction of 56.0±11.3% (p=0.0006) and 61.1±18.9% (p=0.0056) in human MAC deposition for AAV2/8DTAC- and AAV2/8SACT-injected animals, respectively, relative to AAV2/8polyA-injected animals (FIGS. 7D; 8C). Therefore, DTAC and SACT provide significant protection to murine liver vasculature from activated human complement in vivo.

Example 20

Synthesis of STAC

To compare the functionality of recombinant molecules having different order of the complement regulatory regions, soluble terminator of activated complement (STAC), described in U.S. Pat. No. 8,877,896 was utilized. The N-terminus of STAC contains the human CD59 start codon, secretory signal peptide and SCR domain. A polyglycine linker attaches the four SCR domains and S/T-rich region of human CD46 to the C-terminus of CD59. The four SCR domains and S/T-rich region of human CD55 are then linked to the C-terminus of CD46 via a polyglycine sequence (FIG. 9). The c-DNA for STAC was inserted into pShuttle between a CMV enhancer/chicken β-actin promoter (CAG) and a rabbit globin polyadenylation (pA) termination sequence.

The amino acid sequence of STAC (SEQ ID NO: 5) is shown below:

```
MGIQGGSVLFGLLLVLAVFCHSGHSLQCYNCPNPTADCKTAVNCSSDF

DACLITKAGLQVYNKCWKFEHCNFNDVTTRLRENELTYYCCKKDLCNF

NEQLEGGGGGCEEPPTFEAMELIGKPKPYYEIGERVDYKCKKGYFYIP

PLATHTICDRNHTWLPVSDDACYRETCPYIRDPLNGQAVPANGTYEFG
```

-continued
```
YQMHFICNEGYYLIGEEILYCELKGSVAIWSGKPPICEKVLCTPPPKI

KNGKHTFSEVEVFEYLDAVTYSCDPAPGPDPFSLIGESTIYCGDNSVW

SRAAPECKVVKCRFPVVENGKQISGFGKKFYYKATVMFECDKGFYLDG

SDTIVCDSNSTWDPPVPKCLKVGGGGGDCGLPPDVPNAQPALEGRTS

FPEDTVITYKCEESFVKIPGEKDSVICLKGSQWSDIEEFCNRSCEVPT

RLNSASLKQPYITQNYFPVGTVVEYECRPGYRREPSLSPKLTCLQNLK

WSTAVEFCKKKSCPNPGEIRNGQIDVPGGILFGATISFSCNTGYKLFG

STSSFCLISGSSVQWSDPLPECREIYCPAPPQIDNGIIQGERDHYGYR

QSVTYACNKGFTMIGEHSIYCTVNNDEGEWSGPPPECRGKSLTSKVPP

TVQKPTTVNVPTTEVSPTSQKTTTKTTTPNAQATRSTPVSRTTKHFHE

TTPNKGSGTTSGTT
```

Example 21

STAC Functions as a Co-Factor for Factor I Mediated Degradation of C3b

CD46 functions as a co-factor for Factor I mediated proteolytic cleavage of C3b and C4b (Seya T, et al., J Exp Med. 1986; 163(4):837-55). C3b is a component of C3-convertase and thereby promotes its own formation. By enhancing the cleavage of C3b to its inactive form, CD46 acts as a negative regulator of C3-convertase formation and the complement system (Seya T, et al., J Exp Med. 1986; 163(4):837-55). To test whether STAC retains CD46 functionality, 3 μg of C3b was incubated in pAdCAGGFP or pAdCAGSTAC transfected media in the presence or absence of 100 ng of Factor I. Following a 4-hour incubation, samples were examined by quantitative western blot using a polyclonal anti-C3 antibody to assess the amount of C3b α' chain present relative to C3b β chain (FIG. 10A). Samples incubated in media containing STAC were observed to have a 34.3%±3.9% reduction in C3b α' chain signal intensity (p=0.0001) in the presence of Factor I relative to media from pGFP transfected cells containing C3b and Factor I (FIG. 10B). This enhancement of Factor I degradation of C3b indicates that STAC exhibits CD46 functionality.

Example 22

STAC Displays CD55 Functionality

To assess functionality of CD55, a hemolytic assay was performed using GFP and STAC transfected media that had been pre-incubated in the presence or absence of an antibody against CD55's functional site. Erythrocytes suspended in STAC transfected media were observed to have a 32.1%±10.4% (n=6; p=0.0115) reduction in cell lysis compared to the GFP media control (FIG. 11). Pre-incubation with 1000 ng/ml of antibody resulted in a non-statistically significant reduction in cell lysis of 13.4%±9.4% compared to control (n=6; p=0.183) (FIG. 11). The addition of antibody to GFP transfected media resulted in no statistically significant change in cell lysis, indicating that the antibody has no inherent toxic effect. Taken together, these data indicate that the CD55 portion of STAC is functionally active.

Example 23

STAC does not Inhibit the Incorporation of C9 into Membrane Attack Complex

CD59 is a potent inhibitor of the terminal pathway of the complement system (Rollins S A, et al., J Immunol. 1990; 144 (9):3478-83). CD59 functions by blocking C9 incorporation into the membrane attack complex (MAC), thereby blocking pore formation in cellular membranes (Rollins S A, et al., J Immunol. 1990; 144 (9):3478-83). To test whether STAC retained CD59 function, sensitized sheep erythrocytes were incubated in 0.2% C9-depleted normal human serum to allow formation of C5b-8 complex. The cells were then treated with pAdCAGGFP, pAdCAGSTAC or pAdCAGsCD59 media that had been pre-incubated with or without C9. The positive control of sCD59 was observed to have a 21%±9.2% (n=8; p=0.033) reduction in cell lysis compared to GFP media containing C9 (FIG. 12). STAC media containing C9, was observed to have no reduction in cell lysis (n=14; p=0.428), indicating that the CD59 portion of STAC was unable to prevent C9 incorporation and therefore is non-functional (FIG. 12).

The comparison of functionalities of STAC with SACT and DTAC the recombinant proteins provided herein indicate that the order of protein components CD59, CD46 and CD55 in this order as in SACT permits the individual functions of these three components.

---

What is claimed is:

1. A pharmaceutical composition for treating a complement-related condition in a subject, the composition comprising a nucleic acid comprising a nucleotide sequence encoding a recombinant chimeric protein having amino acid sequences from: a CD55, and a CD59 protein; wherein the amino acid sequences from the CD59 protein are C-terminal to the amino acid sequences of the CD55 protein, and wherein the recombinant chimeric protein prevents C9 incorporation in a Membrane Attack Complex and negatively modulates classical and alternative complement pathways.

2. The composition according to claim 1, wherein the nucleotide sequence encoding the recombinant chimeric protein having amino acid sequences from the CD55 protein and the CD59 protein comprises at least one mutation conferring loss of function of a glycosyl phosphatidyl inositol (GPI) anchoring domain, wherein the mutation is at least one of a substitution, a deletion, and an addition.

3. The composition according to claim 1, formulated in a dose effective to treat the subject for the complement-related condition and further optionally comprising a delivery vehicle engineered to target a cell or a tissue, the delivery vehicle selected from the group of: a liposome, a lipid, a polycation, a peptide, a nanoparticle, a gold particle, and a polymer.

4. The composition according to claim 1, wherein the recombinant chimeric protein further comprises a linker connecting the amino acid sequences of the CD55 protein and the CD59 protein.

5. The composition according to claim 1, wherein the nucleotide sequence further encodes a linker comprising at least one amino acid.

6. The composition according to claim 1, wherein the nucleotide sequence encoding the CD55 protein amino acid sequence comprises at least one mutation resulting in loss of function of a glycosyl phosphatidyl inositol (GPI) anchoring domain of the CD55 protein, the mutation comprising a substitution, a deletion, or an addition, or wherein the CD55 protein amino acid sequence comprises at least one of: a short consensus repeat domain and a serine/threonine/proline rich domain.

7. The composition according to claim 1, wherein the nucleotide sequence encoding the recombinant chimeric protein is encoded by a plasmid or a viral vector and wherein the viral vector is at least one selected from the group of: an adenovirus, an adeno-associated virus, a herpesvirus, a poxvirus, and a lentivirus.

8. The composition according to claim 1, wherein the nucleotide sequence comprises a promoter from a gene selected from the group consisting of: a beta actin, a chicken beta actin, a peripherin/RDS, cGMP phosphodiesterase, and a rhodopsin.

9. The composition according to claim 1, further comprising an agent selected from the group consisting of: anti-tumor, anti-coagulant, anti-viral, antibacterial, anti-mycobacterial, anti-fungal, anti-proliferative and anti-apoptotic agents.

10. A kit for regulating or of treating a complement-related condition in a subject, the kit comprising:
a composition comprising a nucleic acid comprising a nucleotide sequence encoding a recombinant chimeric protein comprising amino acid sequences from a CD55 protein, and a CD59 protein, wherein the amino acid sequences from the CD59 protein are C-terminal to the amino acid sequences of the CD55 protein, and wherein the composition negatively modulates classical and alternative complement pathways and is formulated in a dose effective to treat the subject for the complement-related condition;
instructions for treating the subject; and,
a container.

11. A pharmaceutical composition for treating a complement-related condition in a subject, comprising a nucleic acid comprising a nucleotide sequence encoding a recombinant chimeric protein having amino acid sequences from a CD55 protein, and a CD59 protein, or a nucleotide sequence expressing the recombinant chimeric protein, wherein the amino acid sequences from the CD59 protein are C-terminal to the amino acid sequences of the CD55 protein, and wherein the recombinant chimeric protein negatively modulates classical and alternative complement pathways.

* * * * *